US011994521B2

(12) United States Patent
Baaske et al.

(10) Patent No.: US 11,994,521 B2
(45) Date of Patent: May 28, 2024

(54) METHODS FOR MEASURING INTER- AND/OR INTRA-MOLECULAR INTERACTIONS

(71) Applicant: NanoTemper Technologies GmbH, Munich (DE)

(72) Inventors: Philipp Baaske, Munich (DE); Stefan Duhr, Munich (DE); Dennis Breitsprecher, Munich (DE); Christian Osseforth, Munich (DE); Axel Rohde, Munich (DE); Amin Jean Gupta, Munich (DE); Nuska Tschammer, Munich (DE)

(73) Assignee: Nanotemper Technologies GMBH, Munich (DE)

( * ) Notice: Subject to any disclaimer, the term of this patent is extended or adjusted under 35 U.S.C. 154(b) by 343 days.

(21) Appl. No.: 16/625,551

(22) PCT Filed: Jun. 22, 2018

(86) PCT No.: PCT/EP2018/066804
§ 371 (c)(1),
(2) Date: Dec. 20, 2019

(87) PCT Pub. No.: WO2018/234557
PCT Pub. Date: Dec. 27, 2018

(65) Prior Publication Data
US 2020/0278351 A1 Sep. 3, 2020

(30) Foreign Application Priority Data

Jun. 23, 2017 (EP) ..................................... 17177746
Jun. 23, 2017 (EP) ..................................... 17177747

(51) Int. Cl.
G01N 33/58 (2006.01)
G01N 33/543 (2006.01)

(52) U.S. Cl.
CPC ..... G01N 33/582 (2013.01); G01N 33/54313 (2013.01)

(58) Field of Classification Search
CPC ....................... G01N 33/54313; G01N 33/582
See application file for complete search history.

(56) References Cited

U.S. PATENT DOCUMENTS

| | | | |
|---|---|---|---|
| 5,268,486 | A | 12/1993 | Waggoner et al. |
| 6,924,372 | B2 | 8/2005 | Czerney et al. |
| 9,676,787 | B2 | 6/2017 | Hermanson et al. |
| 2003/0059811 | A1 | 3/2003 | Djaballah et al. |
| 2004/0214258 | A1 | 10/2004 | Wood et al. |
| 2007/0009960 | A1 | 1/2007 | Schafer et al. |
| 2009/0305410 | A1* | 12/2009 | Mao ...................... G01N 33/582 435/375 |
| 2013/0251637 | A9 | 9/2013 | Hermanson et al. |
| 2015/0322078 | A1 | 11/2015 | Hermanson et al. |

FOREIGN PATENT DOCUMENTS

| | | |
|---|---|---|
| CA | 2945040 A1 | 10/2015 |
| CN | 101946171 | 1/2011 |
| CN | 104540819 | 4/2015 |
| EP | 2 515 110 A1 | 10/2012 |
| JP | 6104039 B2 | 3/2017 |
| WO | WO-2005/088308 A2 | 9/2005 |
| WO | WO-2008/057437 A2 | 5/2008 |
| WO | WO-2008/061706 A1 | 5/2008 |
| WO | WO-2010/141888 A1 | 12/2010 |
| WO | WO-2011/061944 A1 | 5/2011 |
| WO | WO-2012/164268 A1 | 12/2012 |
| WO | WO-2016/090169 A1 | 6/2016 |
| WO | WO-2016/187580 A1 | 11/2016 |
| WO | WO-2017/055583 A1 | 4/2017 |

OTHER PUBLICATIONS

Duhr et al., "Thermophoresis of DNA determined by microfluidic fluorescence", The European Physical Journal E, Nov. 2004, pp. 277-286, vol. 15, No. 3, EDP Sciences, Springer-Verlag 2004.
Oba et al., Visualization of Cellular Signaling by Florescent Proteins, Japanese Pharmacology Journal, 2011, pp. 13-17, vol. 138, Issue 1, English Abstract Only.
Anonymous, Vybrant™ Cell-Labeling Solutions, Revised: Feb. 8, 2011, Molecular Probes, Retrieved from the Internet: URL:https://assets.thermofisher.com/TFSAssets/LSG/manuals/mp22885.pdf, pp. 1-3.
Extended European Search Report issued in European Application No. 17177747.7-1111 dated Jan. 19, 2018.
International Search Report & Written Opinion issued in International Application No. PCT/EP2018/066804 dated Jul. 27, 2018.
Hwang et al., "Protein induced fluorescence enhancement as a single molecule assay with short distance sensitivity", Proceedings of the National Academy of Sciences of the United States of America, May 3, 2011, pp. 7414-7418, vol. 108, No. 18.
Levitus et al., "Cyanine dyes in biophysical research: the photophysics of polymethine fluorescent dyes in biomolecular environments", Quarterly Review of Biophysics, 2011, pp. 123-151, vol. 44, No. 1, Cambridge University Press 2010.

(Continued)

Primary Examiner — Shafiqul Haq
(74) Attorney, Agent, or Firm — Foley & Lardner LLP

(57) ABSTRACT

A method for measuring interactions between labeled particles and ligands comprising the steps: a) providing a sample comprising labeled particles and ligands in a solution, wherein the labeled particles are dissolved or dispersed in the solution or are immobilized on a solid support; b) exciting fluorescently the labeled particles and detecting the fluorescence of the excited particles at a predetermined temperature; c) repeating steps (a) and (b) multiple times at different concentrations of the ligands in the solution; and d) determining the interaction between the labeled particles and the ligands based on the ligand concentration dependent change of the fluorescence of the labeled particles, wherein the labeled particles are labeled with one or more dyes.

11 Claims, 22 Drawing Sheets

(56) References Cited

OTHER PUBLICATIONS

Sletten et al., "Bioorthogonal Chemistry: Fishing for Selectivity in a Sea of Functionality", Author Manuscript of Angewandte Chemie International Edition in English, 2009, pp. 1-54, vol. 48, No. 38.
Stennett et al., "Demystifying PIFE: The Photophysics Behind the Protein-Induced Fluorescence Enhancement Phenomenon in Cy3", The Journal of Physical Chemistry Letters, 2015, pp. 1819-1823, vol. 6, American Chemical Society.
Tatikolov, "Polymethine dyes as spectral-fluorescent probes for biomacromolecules", Journal of Photochemistry and Photobiology C: Photochemistry Reviews, 2012, pp. 55-90, vol. 13, Elsevier B.V.
Toutchkine et al., "Solvent-Sensitive Dyes to Report Protein Conformational Changes in Living Cells", Journal of the American Chemical Society, 2003, pp. 4132-4145, vol. 125, No. 14, American Chemical Society.

* cited by examiner

TAMRA

TAMRA X

Cy3

MonosulfoCy3

DY547P1

DY495

Oregon Green 488

Cyanine2

DY630

DY631

DY650

DyLight655 B1 to B4

Cy5

Cy5.5

Z-Cy5

MonosulfoCy5, version 1

MonosulfoCy5, version 2

DisulfoCy5

DY647P1

Alexa647SE

IR650

CF640R

ATTO 647N ATTO 655

SeTau647 (not exact structure) BodipyFL

Monosulfo-Z-Cy5 TAMRA

Bodipy 630/650 trisNTA

DY647P1

TrisNTA647 trisNTA

Oregon Green 488 trisNTA Oregon Green 488

US 11,994,521 B2

METHODS FOR MEASURING INTER- AND/OR INTRA-MOLECULAR INTERACTIONS

RELATED APPLICATIONS

The present application claims priority under 37 U.S.C. § 371 to International Patent Application No. PCT/EP2018/066804, filed Jun. 22, 2018, which claims priority to and the benefit of European Patent Application Nos. 17177747.7, filed on Jun. 23, 2017, and 17177746.9, filed on Jun. 23, 2017. The contents of these applications are hereby incorporated by reference in their entireties.

The present invention relates to improved methods for measuring inter- and/or intra-molecular interactions of particles and/or modifications of particles.

BACKGROUND OF THE INVENTION

Solvent-sensitive fluorescent dyes, namely merocyanine dyes, have been reported to be suitable for imaging in vivo by covalent attachment to proteins. These dyes can be used to study conformational changes of proteins (Hahn et al. in J. Am. Chem. Soc. 2003, 125, 4132-4145).

Polymethine dyes have been reported to be useful as spectral-fluorescent probes for studying noncovalent interactions of these dyes with biomacromolecules such as nucleic acids and proteins (Tatikolov in Journal of Photochemistry and Photobiology C: Photochemistry Reviews 2012, 13, 55-90).

Further, it has been reported, that the photophysical properties of cyanine dyes are affected by the molecular environment within a biomolecule, thus making these dyes suitable as fluorescent probes in biophysical research (Levitus et al. in Quaterly Reviews of Biophysics 2010, 1-29).

Protein-induced fluorescent enhancement is an effect which has been reported to describe an increase in fluorescence intensity occurring when a protein binds to a nucleic acid in the proximity of a fluorescent probe. In particular, cyanine dyes being covalently attached to DNA experience a fluorescence intensity increase when a protein binds to DNA (Myong et al. in PNAS 2011, 108, 7414-7418; Levitus et al. in J. Phys. Chem. Lett. 2015, 6, 1819-1823).

Merocyanine dyes have been reported to be useful as dyes to detect and quantify protein activities such as conformational changes and ligand binding. In addition, biosensor molecules which can bind to selected targets and methods for detecting target biomolecules and protein activities are disclosed in WO 2005/088308 A2.

A method for measuring interactions of particles, especially interactions between biomolecules and ligands, by thermo-optical characterization is disclosed in WO 2008/061706 A1. This thermo-optical characterization is based on thermophoresis resulting from the creation of strong temperature gradients.

SUMMARY OF THE INVENTION

The present invention relates to improved methods for measuring inter- and/or intra-molecular interactions of particles and/or modifications of particles. In particular, the methods of the present invention provide an improved sensitivity. Furthermore, the methods of the present invention employ dyes which allow the detection of interactions which could not have been measured with sufficient sensitivity by previously known methods. Further, the method is independent of the method/source of heating and also independent of the geometry of the reaction vessel (i.e., the experiment can be done in a well plate and not only in capillaries).

In the methods of the present invention, labeled particles are employed which are labeled with one or more temperature-sensitive dyes.

In a first aspect, the present invention relates to a method for measuring interactions between labeled particles and ligands. The method of the first aspect comprises the following steps:
  a) providing a sample comprising labeled particles and ligands in a solution, wherein the labeled particles are dissolved or dispersed in the solution or are immobilized on a solid support;
  b) exciting fluorescently the labeled particles and detecting the fluorescence of the excited particles at a predetermined temperature;
  c) repeating steps (a) and (b) multiple times at different concentrations of the ligands in the solution; and
  d) determining the interaction between the labeled particles and the ligands based on the ligand concentration dependent change of the fluorescence of the labeled particles.

In a second aspect, the present invention relates to a method for measuring inter- and/or intra-molecular interactions. The method of the second aspect comprises the following steps:
  a) providing a sample comprising labeled particles;
  b) exciting fluorescently the labeled particles and detecting a first fluorescence of the excited particles at a first temperature;
  c) heating or cooling the sample to a second temperature;
  d) exciting fluorescently the labeled particles and detecting a second fluorescence of the excited particles at the second temperature;
  e) characterizing inter- and/or intra-molecular interactions and/or modifications/alterations of the particles based on the first and second fluorescence.

In a third aspect, the present invention relates to a method for measuring time dependent changes. The method of the third aspect comprises the following steps:
  a) providing a sample comprising labeled particles;
  b) exciting fluorescently the labeled particles and detecting a first fluorescence of the excited particles;
  c) waiting for a predetermined time;
  d) exciting fluorescently the labeled particles and detecting a second fluorescence of the excited particles;
  e) characterizing the time dependent change of the particles based on the first and second fluorescence.

In a fourth aspect, the present invention relates to a method for measuring environmental dependent changes. The method of the fourth aspect comprises the following steps:
  a) providing a first sample comprising labeled particles;
  b) exciting fluorescently the labeled particles and detecting a first fluorescence of the excited particles in the first sample;
  c) providing a second sample comprising the labeled particles at substantially the same concentration, wherein the second sample differs from the first sample;
  d) exciting fluorescently the labeled particles and detecting a second fluorescence of the excited particles in the second sample;
  e) characterizing the environmental dependent change of the particles based on the first and second fluorescence.

In a fifth aspect, the present invention relates to a protein labeling kit comprising two reactive dyes, wherein the dyes have a spacer group, the spacer group having a reactive group that enables the conjugation of the dye to a protein.

DETAILED DESCRIPTION OF THE INVENTION

Figure 1:
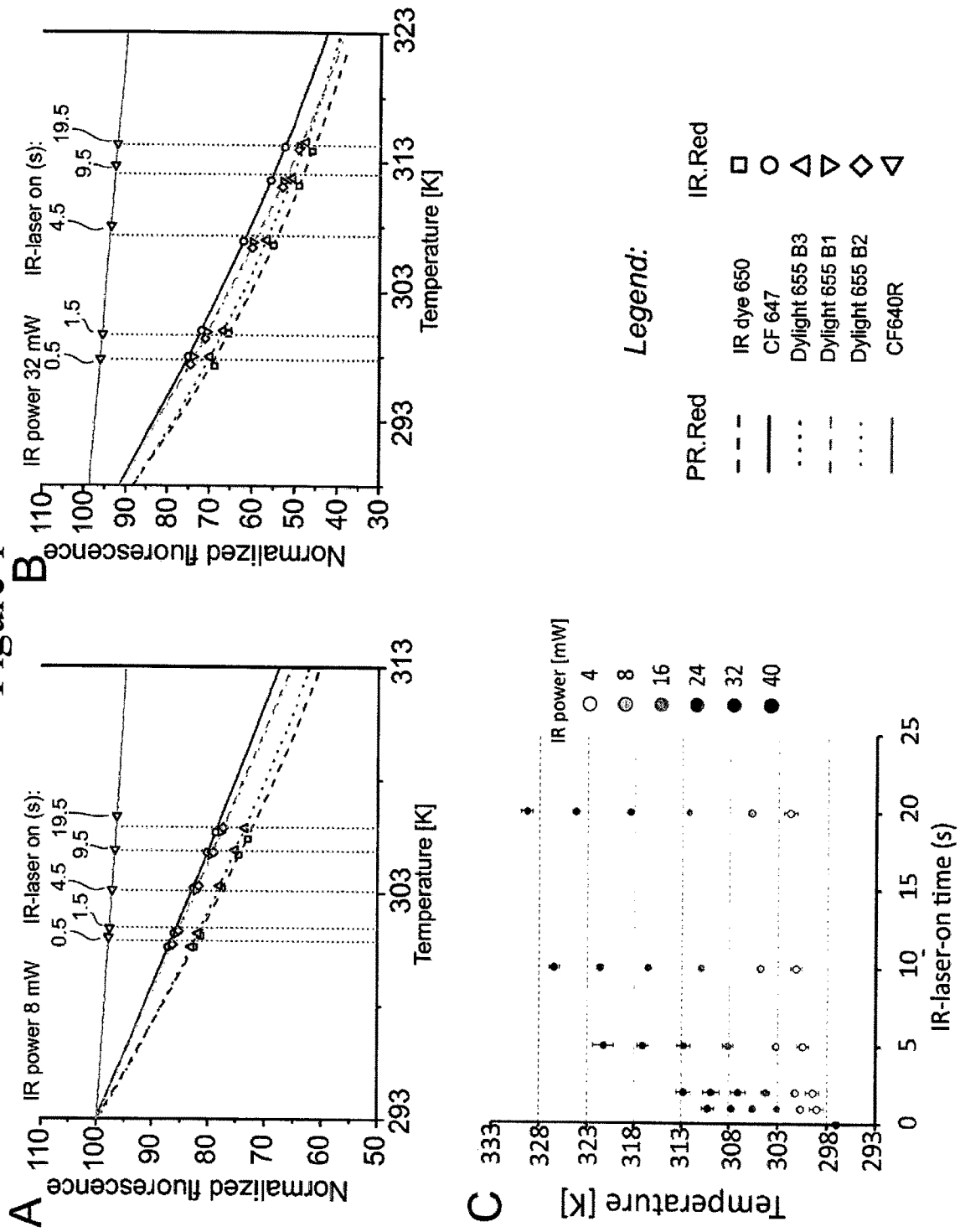
FIG. 1 shows a temperature induced fluorescence intensity change of chosen polymethine and xanthenes dyes using Peltier device or IR laser as heating source.

The present invention provides methods for measuring inter- and/or intra-molecular interactions of particles and/or modifications of particles. The methods of the present invention provide an improved sensitivity. Furthermore, the methods of the present invention employ dyes which allow the detection of interactions which could not have been detected with sufficient sensitivity by previously known methods.

According to the present invention, modification of particles includes, for example glycosylation, phosphorylation, lipidation, carbonylation, oxidation of particles and the like.

The term interaction comprises interaction between biomolecules (e.g., protein, DNA, RNA, hyaluronic acids etc.) but also between (modified) (nano)particles/(micro)beads and biomolecules.

In particular, the methods of the present invention allow to measure the stability of molecules, like biomolecules, or the interaction of molecules, particularly biomolecules with, e.g., further (bio)molecules, particularly modified biomolecules, particles, e.g., nanoparticles or microparticles, beads, e.g., microbeads. Also combinations of these characteristics may be determined with the means and methods of this invention. It is noted that the present invention is, however, not limited to the measurement/characterization of biomolecules. Therefore, also the characteristics of other compounds/particles can be measured and determined by the means and methods disclosed herein, for example kinetic events and interactions of molecules may be determined and/or measured. Accordingly, also chemical reactions (like inorganic or organic reactions) may be measured by the methods of the present invention. It is also envisaged to determine complex formations and/or their dissociation. This characterization comprises, inter alia, determination of biophysical characteristics, like melting points or melting curves, complex formations, protein-protein interactions, protein or peptide folding/unfolding, intra-molecular interactions, intermolecular interactions, the determination of interactions between particles or molecules, and the like.

Accordingly, with the methods provided herein it is, inter alia, possible to measure, detect and/or verify biological, chemical or biophysical processes and/or to investigate, study and/or verify samples, like biological or pharmaceutical samples. Also diagnostic tests are feasible and are embodiments of this invention. It is, inter alia, envisaged and feasible to measure the melting features of proteins or nucleic acid molecules, like, e.g., of double-stranded DNA or double-stranded RNA (dsDNA/dsRNA) or of hybrid nucleic acid molecules, like DNA/RNA hybrids, to measure and or analyze nucleic acid sequences, like the detection and/or measurement of Single Nucleotide Polymorphisms (SNPs) or to measure the stability of nucleic acid molecules in correspondence and as a function of their relative length; to measure and/or verify PCR end products, e.g., in general medical diagnostic, also in polar-body diagnostic, pre-implantation diagnostic, forensic analysis. Accordingly, it is evident for the skilled artisan that the means and methods provided in this invention are, particularly and non-limiting, useful in measurements and/or verifications wherein the affinities to other molecules/particles of a given particle/molecule is of interest. For example, the methods provided herein as well as the devices are useful in the detection and measurement of temperature stability as well as melting points of nucleic acid molecules and proteins. Therefore, it is within the scope of the present invention that, for example, (DNA-) primers and (DNA- or RNA-) probes are measured and or verified after or during their synthesis. Also the measurement of nucleic acid molecules on templates, like DNA-chips is envisaged. The term melting in the context of this invention refers to the thermal denaturation of biomolecules, like nucleic acids (e.g., RNAs, DNAs) or proteins.

Also envisaged in the context of the present invention is the measurement, detection and/or verification of mutations and genetic variations in nucleic acid molecules, for example in form of single-strand conformational polymorphisms (SSCPs) or in form of restriction fragment length polymorphisms (RFLPs) and the like. The present invention also provides for the possibility to analyze heteroduplexes. Heteroduplexes are generated by heat denaturation and reannealing of a mixture of, e.g., wild type and mutant DNA molecules. In particular it is also possible to measure the effect of protein binding to a DNA molecule on the stability of the latter. Furthermore it is possible to measure the thermal stability of proteins and the effect of molecules (e.g., small molecules, drugs, drug candidates) on the thermal denaturation.

Also within the scope of the present invention is, e.g., the measurement of protein-protein interactions, like complex formations of proteinaceous structures or of proteins or of fragments thereof. Such measurements comprise, but are not limited to, the measurement of antibody-antigen binding reactions (also in form of single chain antibodies, antibody fragments, chromobodies and the like). Yet, the embodiments of the present invention are also related to the detection and or measurement of dissociation events, like, e.g., the dissociation of protein complexes. Therefore, the invention is also useful in the measurement, determination and/or verification of dissociation events, like in the measurement of the dissociation of proteinaceous complexes, e.g., antibody-antigen complexes and the like.

The present invention is not-limited to the detection of short DNA or the determination of double- or single-stranded nucleic acid molecules. Also interactions between particles/molecules, conformations, hydrodynamic radii, binding kinetics and stabilities of particles/molecules, e.g., proteins, nucleic acids (e.g., DNA, RNA, PNA, LNA), nanoparticles, beads, particularly microbeads, lipids, liposomes, vesicles, cells, biopolymers (hyaluronic acid, alginate and alike), two-dimensional lipid sheets, inorganic substances (e.g., carbon-nanotubes, buckyballs, etc), Polyethyleneglycol (PEG) may be measured.

In the first aspect, the present invention relates to a method for measuring interactions between labeled particles and ligands. In this method, the interaction of labeled particles with ligands can be measured depending on the concentration of the ligand.

The method of the first aspect of the present invention comprises the following steps:
a) providing a sample comprising labeled particles and ligands in a solution, wherein the labeled particles are dissolved or dispersed in the solution or are immobilized on a solid support;
b) exciting fluorescently the labeled particles and detecting the fluorescence of the excited particles at a predetermined temperature;
c) repeating steps (a) and (b) multiple times at different concentrations of the ligands in the solution; and
d) determining the interaction between the labeled particles and the ligands based on the ligand concentration dependent change of the fluorescence of the labeled particles.

Preferably, the labeled particles and the ligands are provided in step a) in predetermined concentrations in the solution or, in case the labeled particles are immobilized on a solid support, the labeled particles are provided in a predetermined amount and the ligands are provided in a predetermined concentration. This means that the amount of labeled particles and ligands in each fluorescent measurement is predefined and not changed between steps a) and b), e.g. by a washing step. Further, the solution provided in step a) is used in step b) for exciting fluorescently the labeled particles and detecting the fluorescence of the excited particles at a predetermined temperature.

Using the method of the first aspect of the present invention, a binding curve showing the ligand concentration dependent change of the fluorescence of the labeled particles can be obtained. From the binding curve (also referred to as "thermo-optical profile"), the dissociation constant of the particle and the ligand can be determined. Thus, in a particularly preferred embodiment of the present invention, the method of measuring interactions between labeled particles and ligands is a method of measuring the dissociation constant of the particles and the ligands, such as the dissociation constant of a particle-ligand bond.

Preferably, interactions between biomolecule/ligand, protein/ligand, protein/protein or receptor/ligand can be determined by the method of the first aspect of the present invention.

In a preferred embodiment of the first aspect of the present invention, step (b) comprises the following steps:
ba) heating or cooling the solution to a predetermined temperature;
bb) exciting fluorescently the labeled particles and detecting the fluorescence of the excited particles at the predetermined temperature.

The additional heating or cooling step is advantageous for a specific regulation of the predetermined temperature. In order to measure relative differences in fluorescence of $1/1000$, it is preferable to control the predetermined temperature using a heating or cooling element such as a Peltier element or an IR laser. It is advantageous to control the predetermined temperature so that a temperature drift over time is avoided and temperature variations are smaller than $+/-1$ K, preferably smaller than $+/-0.5$ K.

Thus, in a preferred embodiment, the method of the first aspect of the present invention comprises the following steps:
a) providing a sample comprising labeled particles and ligands in a solution, wherein the labeled particles are dissolved or dispersed in the solution or are immobilized on a solid support;
ba) heating or cooling the solution to a predetermined temperature;
bb) exciting fluorescently the labeled particles and detecting the fluorescence of the excited particles at the predetermined temperature;
c) repeating steps (a) and (b) multiple times at different concentrations of the ligands in the solution; and
d) determining the interaction between the labeled particles and the ligands based on the ligand concentration dependent change of the fluorescence of the labeled particles.

Without wishing to be bound by theory, it is believed that the change in fluorescence of the labeled particle, i.e. the dye conjugated to the particle, when the ligand binds to the labeled particle, is based on the following theoretical principles:

One of the most important parameters of a thereto-optical measurement is the binding amplitude $\Delta F_{norm}$ defined as follows:

$$\left| \frac{F_{bound}(T_{end})}{F_{bound}(T_{start})} - \frac{F_{unbound}(T_{end})}{F_{unbound}(T_{start})} \right| = |F_{norm}^{bound} - F_{norm}^{unbound}| = \Delta F_{norm}$$

Figure 17:
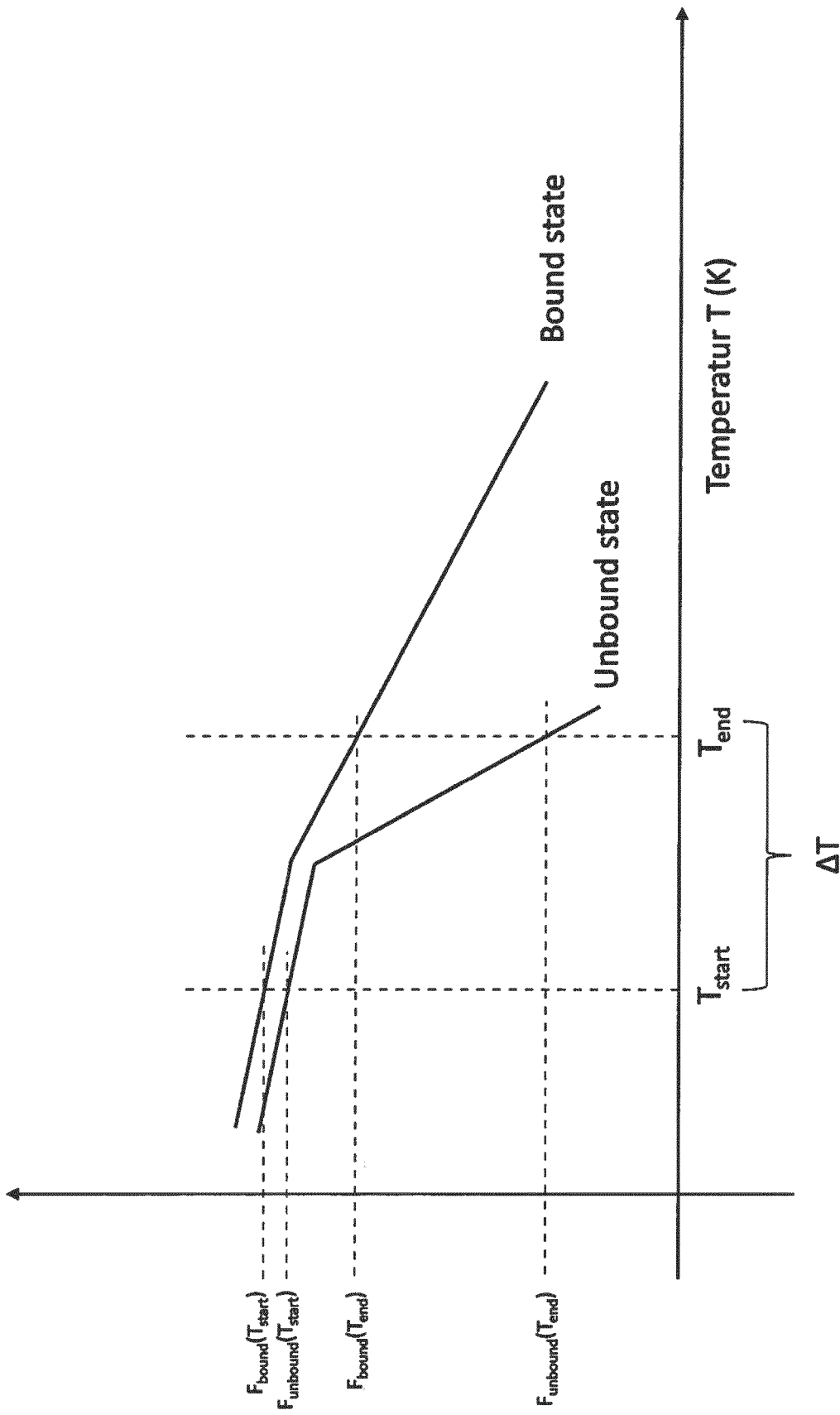
FIGS. 17 and 18 show exemplary schematic representations for the change of the fluorescence with the temperature for the bound and unbound state.

Here, F is the measured fluorescence value at a temperature T. Fluorescence values are compared at a starting temperature and at a different end temperature $T_{end}$. The ratio of the two fluorescence values gives the normalized fluorescence $F_{norm}$. The value of $\Delta F_{norm}$, i.e., the difference between the values for bound and unbound states, should be as large as possible in order to achieve optimum measurement results with an optimal signal to noise ratio. FIG. 17 shows an exemplary schematic representation for the change of the fluorescence with the temperature for the bound and unbound state. The fluorescence values used are indicated accordingly. The actual course of the curves can vary widely. Furthermore, it is quite conceivable to carry out the measurement in such a way that the solutions are cooled down, i.e., $T_{start}$ and $T_{end}$ are thus interchanged.

$\Delta F_{norm}$ is generally higher with increasing temperature difference between $T_{start}$ and $T_{end}$. However, $\Delta F_{norm}$ is always also dependent on the fluorophore used as well as the labeled molecule and the titrated ligand.

$$|T_{end} - T_{start}| = \Delta T$$

$$\Delta F_{norm} \sim \Delta T$$

In many interactions $$|F_{bound}(T_{start}) - F_{unbound}(T_{start})| = \Delta F_{start}$$

already shows a dependence on the concentration of the titrated ligand. In other words, a ligand dependency of the absolute fluorescence value can already be seen in the case of $T_{start}$ (i.e., the predetermined temperature) without a change in the temperature. The relative change in fluorescence between bound and unbound state $$\frac{F_{unbound}(T_{start})}{F_{bound}(T_{start})}$$

is, however, very small (in the range of a few percent) in most cases. During the production of the samples, random deviations of the target concentration (and thus the absolute fluorescence values) of several percent are generated by both manual and automated liquid handling processes, whereby the ligand dependence of the absolute fluorescence at $T_{start}$ is masked (i.e., unfavorable signal to noise ratio). It is therefore preferred to measure the fluorescence at two different temperatures and to calculate a quotient of the two values (measured at different temperatures), whereby liquid handling errors can be corrected.

However, the relative change of the fluorescence with changing temperature as a function of the ligand, i.e., the relative binding amplitude $A_r$, $$\frac{\left[ \frac{F_{bound}(T_{end})}{F_{bound}(T_{start})} \right]}{\left[ \frac{F_{unbound}(T_{end})}{F_{unbound}(T_{start})} \right]} = A_r$$

is also often small, again in the range of a few percent and dependent on $\Delta T$. Pipetting errors do not play any role since relative values are considered, but $A_r$ is about 1 for all temperatures smaller than an unknown temperature $T_X$ (FIG. 18).

Only for temperatures higher than $T_X$, $A_r$ begins to deviate from 1, and only in this case a bond can be measured with high precision. The measurement result is better, the larger or the smaller $A_r$ is, i.e., the more $A_r$ deviates from 1.

In summary, this means that the fluorescence should be measured at more than one temperature in order to eliminate pipetting errors. On the other hand, the temperature $T_X$ at which $A_r$ deviates from 1 at the beginning of the measurement depends on the fluorophore used, the labeled target molecule and the titrated ligand. This means that a broad temperature range should be scanned in order to determine $T_X$. The temperature $T_{end}$ is ideally higher than $T_X$. Depending on how much Ar differs from 1, a larger $\Delta T$ is also preferable in some cases in order to achieve sufficient signal to noise ratios. However, small values of $\Delta T$ are preferable, since for large values for $\Delta T$ the thermodynamic equilibrium of the bond can differ greatly from the thermodynamic equilibrium at $T_{start}$.

Figure 18:
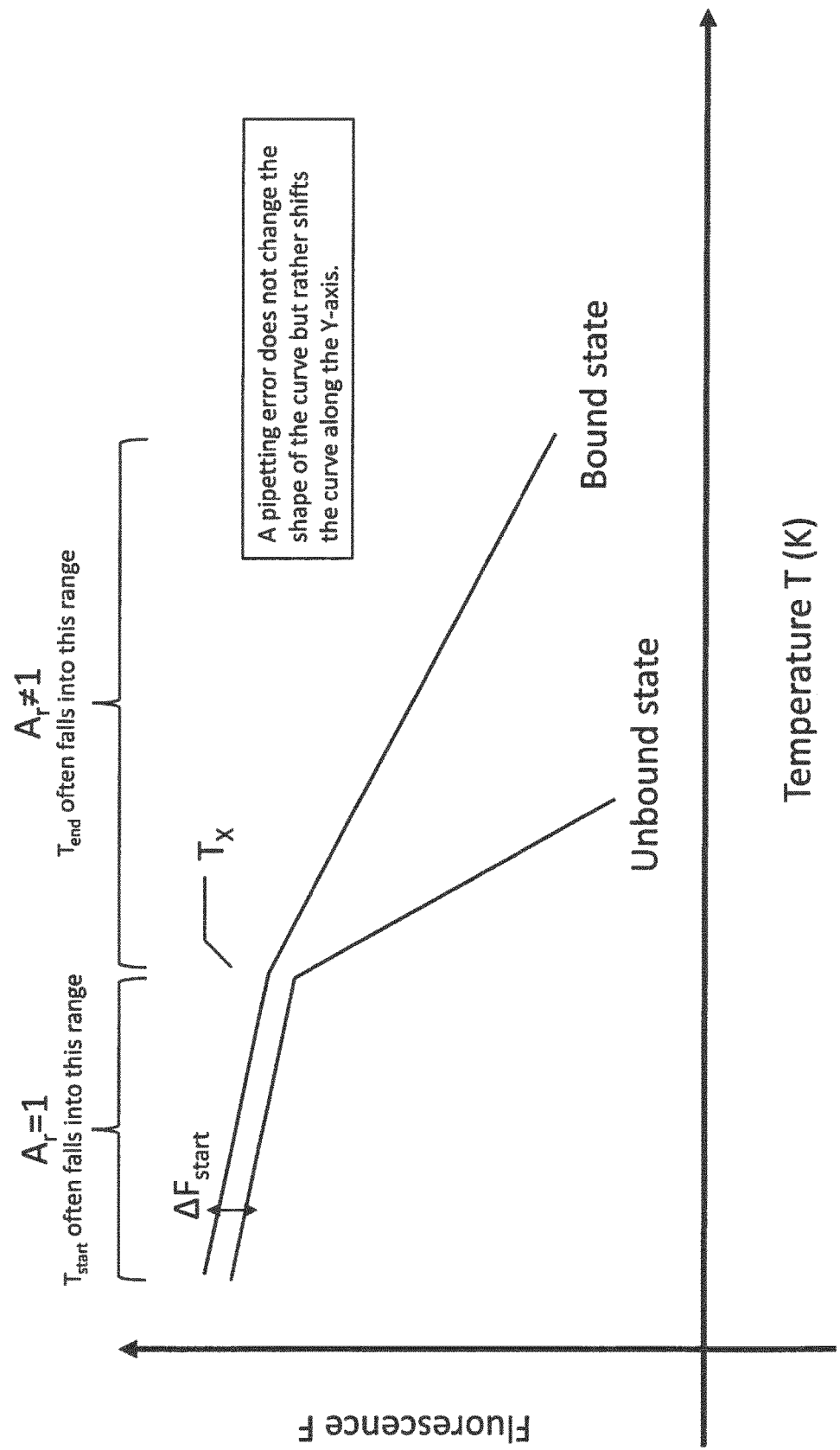
Figure 19A:
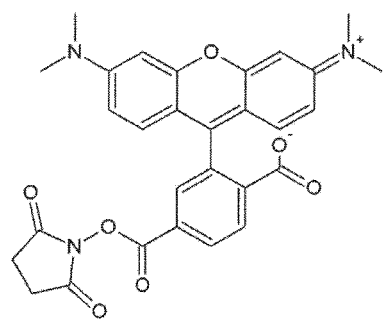
FIGS. 19a to 19e show structures of specific dyes
Figure 19A:
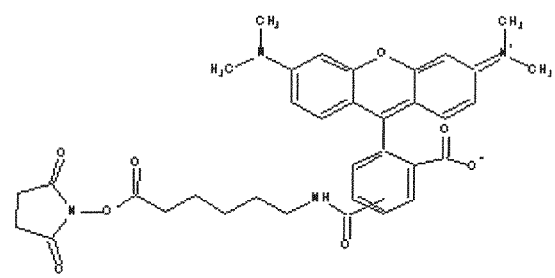
Figure 19A:
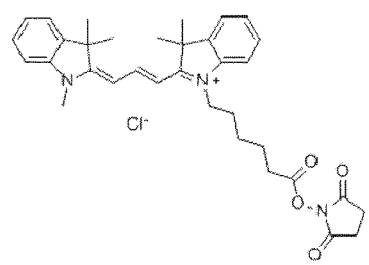
Figure 19A:
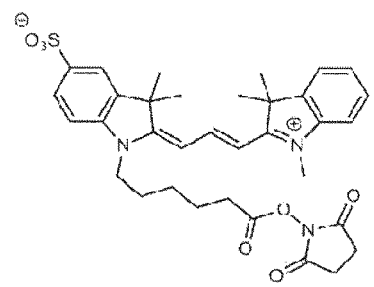
Figure 19A:
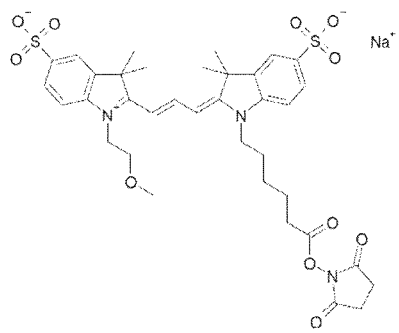
Figure 19A:
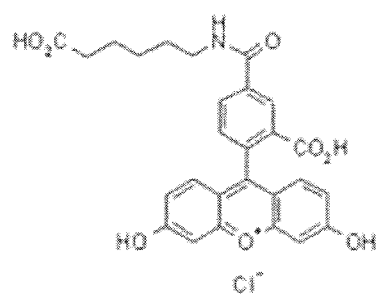
Figure 19B:
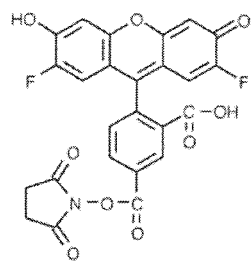
Figure 19B:
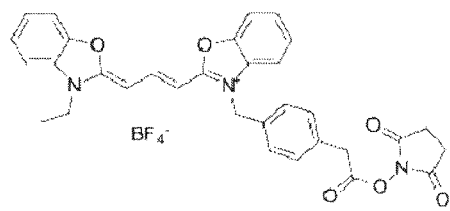
Figure 19B:
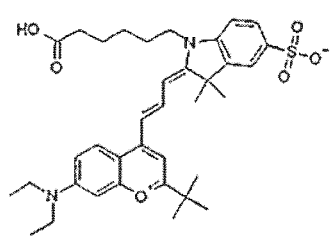
Figure 19B:
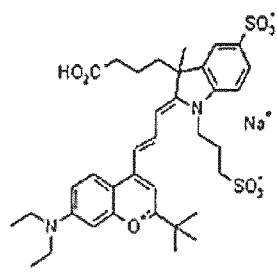
Figure 19B:
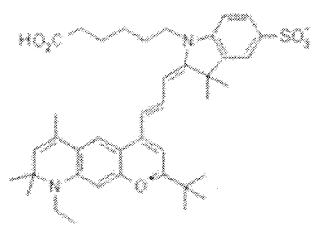
Figure 19B:
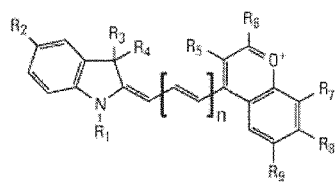
Figure 19B:
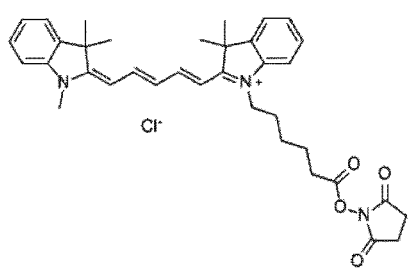
Figure 19B:
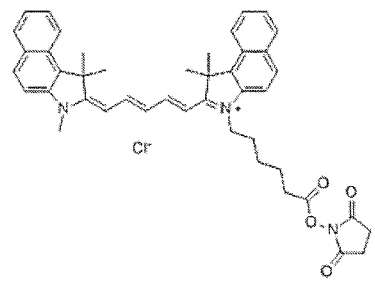
Figure 19C:
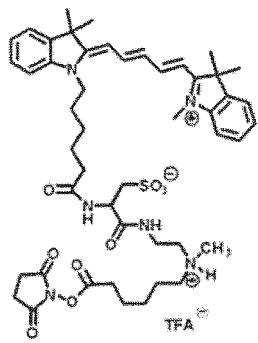
Figure 19C:
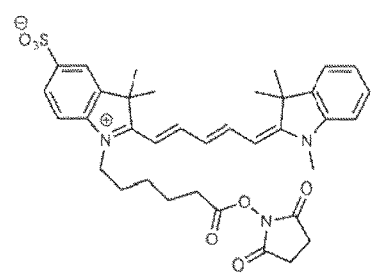
Figure 19C:
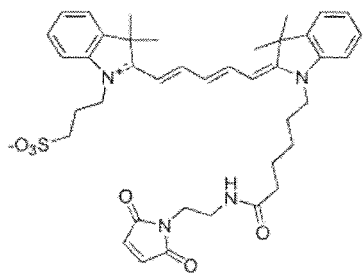
Figure 19C:
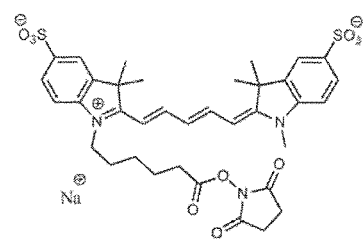
Figure 19C:
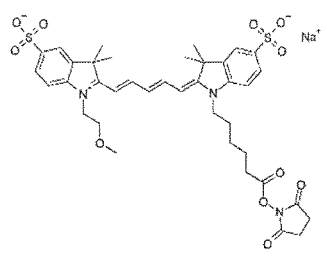
Figure 19C:
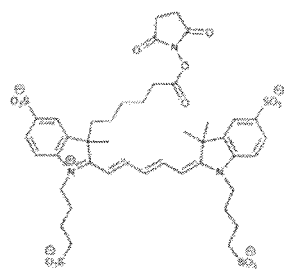
Figure 19C:
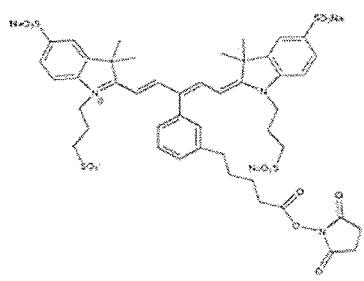
Figure 19C:
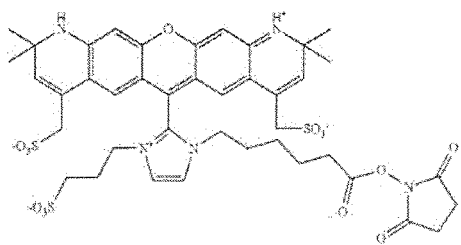
Figure 19D:
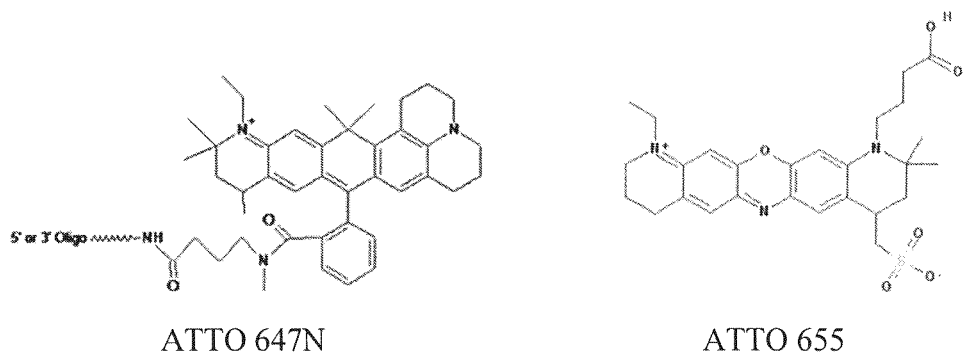
Figure 19D:
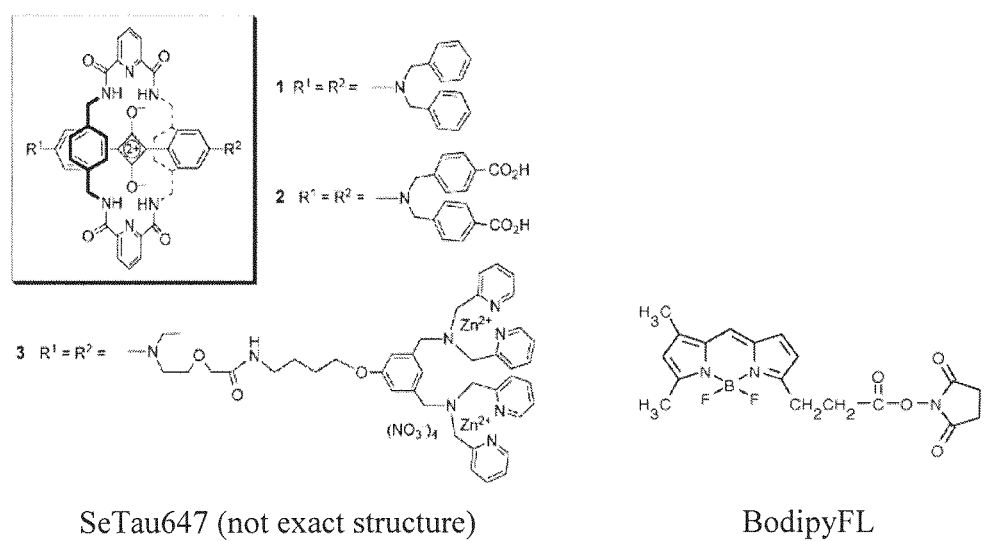
Figure 19D:
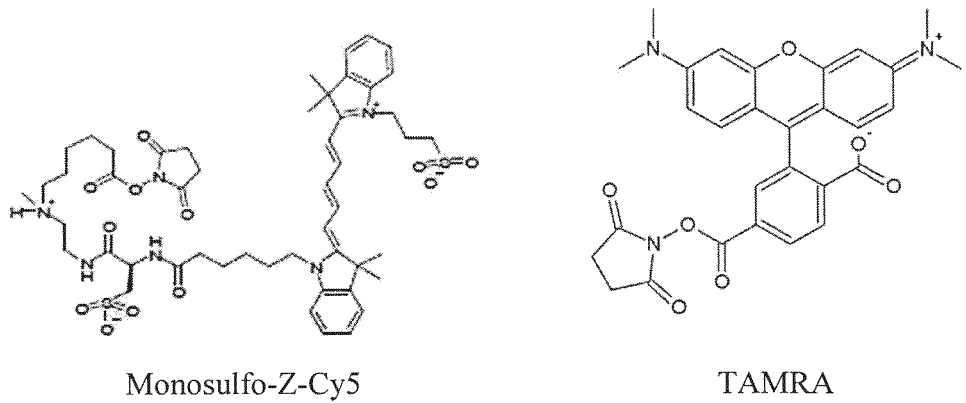
Figure 19E:
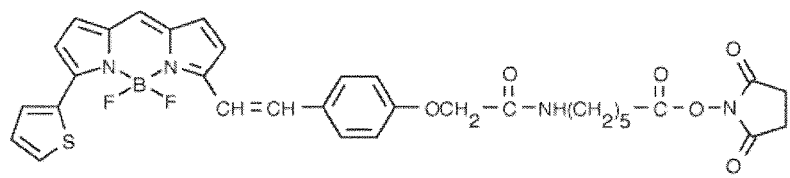
Figure 19E:
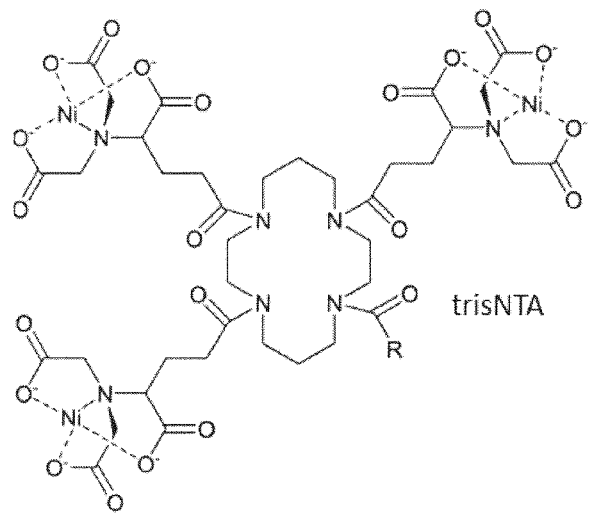
Figure 19E:
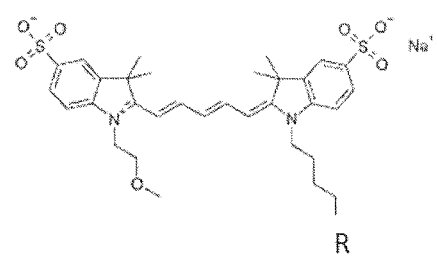
Figure 19E:
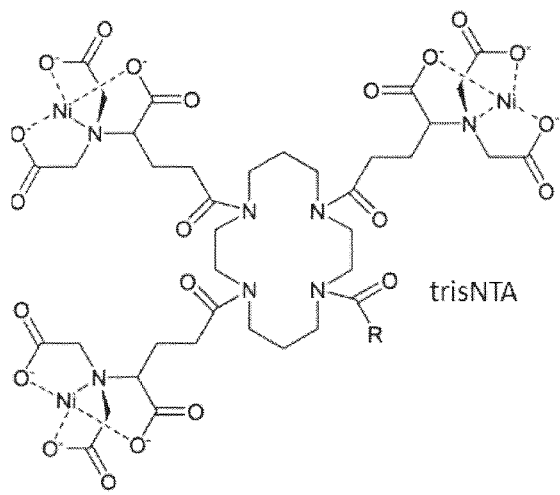
Figure 19E:
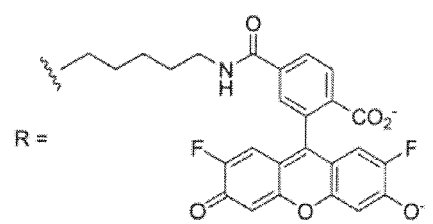

FIG. 18 shows an exemplary schematic representation for the change of the fluorescence with the temperature for the bound and unbound state. Further terms and values mentioned above are marked. From this figure, it is also apparent that $\Delta F_{start}$ becomes larger the larger $T_{start}$ but only if $T_{start} > T_X$. The displayed fluorescence change does not necessarily need to be linear, also exponential decays are likely. FIG. 18 shows a linear function for simplification.

It is noted that the methods of the present invention do not rely on thermo-optical characterization based on thermophoresis resulting from the creation of strong spatial temperature gradients.

Thus, in a more preferred embodiment of the first aspect of the present invention, step (b) comprises the following steps:
  b1) exciting fluorescently the labeled particles and detecting the fluorescence of the excited particles at a first predetermined temperature;
  b2) heating or cooling the solution to a second predetermined temperature;
  b3) exciting fluorescently the labeled particles and detecting the fluorescence of the excited particles at the second predetermined temperature.

In this preferred embodiment, the fluorescence of the labeled particles is determined in the presence of varying concentrations of the ligand at two different temperatures. As explained above, this procedure allows to eliminate pipetting errors.

In this preferred embodiment, the interaction between the labeled particles and the ligands can be determining based on the ligand concentration dependent change of the ratio of the fluorescence F2 at the second predetermined temperature divided by the fluorescence F1 at the first predetermined temperature F1, i.e., F2/F1.

In the first aspect of the present invention, the predetermined temperature is a temperature at which the ligand binds to the labeled particle. In other words, the predetermined temperature is a temperature at which a fraction of the dye which undergoes a conformational change in the fluorescence excitation changes due to binding of the ligand to the labeled particle. Further, the predetermined temperature is a temperature at which a photoisomerization rate or internal conversion rate of the dye changes due to binding of the ligand to the labeled particle.

In the context of the present invention, the term "binding" of the ligand to the labeled particle, refers to covalent binding or binding by intermolecular forces such as ionic bonds, hydrogen bonds and van der Waals forces.

When in the following reference is made to "the predetermined temperature", the same applies to the first predetermined temperature and the second predetermined temperature in the more preferred embodiment of the first aspect of the present invention.

It is advantageous to select the predetermined temperature depending on the nature of the respective particles. In this respect, the predetermined temperature should preferably be below the temperature, at which the particles dissolve, unfold and/or alter. Exemplarily for the case that the particles are proteins, the predetermined temperature may preferably be adjusted to be below the onset temperature of thermal denaturing of the protein. The onset temperature can be determined by conducting a thermal stability measurement as inter alia described in WO 2017/055583 A1.

The predetermined temperature in the first aspect of the present invention is preferably in the range of 20° C. to 115° C., preferably 0.1° C. to 100° C., more preferably in the range of 10° C. to 60° C., most preferably in the range of 10° C. to 40° C. It is preferable to generate a stable predetermined temperature, i.e., to control the predetermined temperature within a narrow range, preferably within +/−1 K, more preferably within +/−0.5 K.

Typically, room temperature fluctuates by more than +/−1 K, even if it is actively controlled by e.g. air conditioning. Therefore, if the predetermined temperature is room temperature, a further control of the predetermined temperature is necessary to achieve a stable predetermined temperature. More preferably, the predetermined temperature is different from room temperature. Room temperature means a temperature between 20° C. to 25° C., preferably 25° C.

Likewise, in the more preferred embodiment of the first aspect of the present invention, the first and second predetermined temperatures in the heating or cooling step are preferably in the range of −20° C. to 115° C., preferably 0.1° C. to 100° C., more preferably in the range of 5° C. to 60° C., even more preferably in the range of 10° C. to 60° C., most preferably in the range of 10° C. to 40° C. The first predetermined temperature is preferably in the range of −20° C. to 115° C., preferably 0.1° C. to 100° C., more preferably in the range of 5° C. to 60° C., even more preferably in the range of 10° C. to 60° C., most preferably in the range of 10° C. to 40° C. The second predetermined temperature is preferably in the range of −20° C. to 115° C., preferably 0.1° C. to 100° C., more preferably in the range of 5° C. to 60° C., even more preferably in the range of 10° C. to 60° C., most preferably in the range of 10° C. to 40° C. It is understood that in the case of heating, the first predetermined temperature is chosen sufficiently low so that the second predetermined temperature does not exceed the above described upper limit thereof. Likewise, in the case of cooling, the first predetermined temperature is chosen sufficiently high so that the second predetermined temperature does not exceed the above described lower limit thereof. As described above, also here it is advantageous that the first and second predetermined temperatures are stably controlled to low temperature fluctuations, preferably smaller than +/−1 K.

The difference between the first predetermined temperature and the second predetermined temperature is usually in the range from +/−0.1 K to +/−90 K. This means that the absolute value of the temperature difference $|T^{2nd}-T^{1st}|$ is between 0.1 K and 90 K, i.e., the temperature difference can be positive (heating) or negative (cooling). Preferably, the temperature difference is in the range from +/−1 K and +/−40 K, more preferably in the range from +/−1 K to +/−20 K. A low temperature difference is advantageous, because the system is disturbed as little as possible by the change in temperature. The person skilled in the art is aware that by cooling the overall sample, a higher amplitude of temperature increase (i.e., by laser heating) is possible without causing damage to temperature sensitive materials.

In the method of the preferred embodiments of the first aspect of the present invention, the heating or cooling can be carried out using a heating or cooling source selected from the group consisting of heating or cooling fluids or gases, heating elements (for example a heating resistor, or other elements based on joule heating like Metal heating elements, Ceramic heating elements, Polymer PTC heating elements, Composite heating elements, semiconductor heating elements), or a thermoelectric element, for example a Peltier element, or electromagnetic radiation (like an LED, e.g., an IR-LED, or a laser, e.g., an IR-Laser, or a microwave).

A Peltier element is preferably used because it can be used to heat the sample and/or to cool the sample (e.g., to cool the sample below the environmental temperature). In particular, it is possible to switch from heating to cooling by reversing the direction of the current through the Peltier element. A Peltier element is one of the few elements that can heat but also actively cool under room temperature.

A laser, preferably a laser whose electromagnetic radiation is directly absorbed by the sample, is preferably used because the temperature can be changed rapidly and directly in the sample without mechanical contact to the sample.

Laser radiation is directly absorbed by the sample and converted to heat, e.g., IR laser light of the wavelengths 980 nm+/−30 nm, 1480 nm+/−30 nm, 1550 nm+/−30 nm, 1940 nm+/−30 nm is very well absorbed by water and heats up very quickly. This heating method is contact-less, i.e., fast and without the risk of contamination. The sample chamber must only be transparent to the laser light but does not require a good thermal conductivity, in contrast to contact heating by means of a heating element.

The temperature induced fluorescence intensity change is solely dependent on the physicochemical properties of a dye (FIG. 1). Because the degree of the temperature induced fluorescence intensity change is solely dependent on the physicochemical properties of the dye, it is independent of the heating source used. Thus, based on the fluorescence intensity of the dye at a defined IR-laser on-time, the temperature of the probe can be estimated.

With the laser, only the nanoliter volume range is heated up, of which the fluorescence is measured by fluorescence optics (detection volume is often only 100 μm×100 μm×100 μm=1 nl volume). It is not necessary to heat a larger volume of which the fluorescence optics often cannot the detect fluorescence.

In the preferred embodiment of the first aspect of the present invention, steps (b2) and (b3) can be carried out consecutively or simultaneously.

According to the first aspect of the present invention the particles include biomolecules, nanoparticles, microparticles and vesicles. The particles also include biological cells (e.g., bacterial or eukaryotic cells) or sub-cellular fragments, viral particles or viruses and cellular organelles and the like. Nanoparticles also include nanodiscs. A nanodisc is a synthetic model membrane system composed of a lipid bilayer of phospholipids with the hydrophobic edge screened by two amphipathic proteins.

Biomolecules are preferably selected from the group consisting of amino acids, proteins, peptides, mono- and disaccharides, polysaccharides, lipids, glycolipids, fatty acids, sterols, vitamins, neurotransmitter, enzymes, nucleotides, metabolites, nucleic acids, and combinations thereof. More preferably, the biomolecules are selected from the group consisting of proteins, peptides, enzymes, nucleic acids, and combinations thereof.

Preferably, the particles (in the labeled particles) are biomolecules, most preferably proteins or nucleic acids.

The proteins are selected from the group consisting of enzymes (e.g., carbonic anhydrase, beta lactamase TEM1, or kinases such as MEK1 and p38), transporter proteins (e.g., MBP), inhibitory proteins (e.g., beta lactamase inhibitory protein BLIP, Anakinra), structural proteins, signaling proteins, ligand-binding proteins, chaperones (e.g., heat shock protein HSP90), antibodies (e.g., Trastuzumab), and receptors (e.g., interleukin 1 receptor).

Nucleic acids include DNA, RNA, LNA and PNA. Locked nucleic acid (LNA), often referred to as inaccessible RNA, is a modified RNA nucleotide. The ribose moiety of an LNA nucleotide is modified with an extra bridge connecting the 2' oxygen and 4' carbon. Peptide nucleic acid (PNA) is an artificially synthesized polymer similar to DNA or RNA. DNA and RNA have a deoxyribose and ribose sugar backbone, respectively, whereas PNA's backbone is composed of a peptide such as repeating N-(2-aminoethyl)-glycine units linked by peptide bonds. The various purine and pyrimidine bases are linked to the backbone by a methylene bridge ($—CH_2—$) and a carbonyl group ($—(C=O)—$).

In the context of the present invention, a nanoparticle is a particle having an average size of less than 100 nm. The term "average size" describes the mean effective diameter as measured by dynamic light scattering using, for example, Brookhaven Instruments' 90Plus or Malvern Zetasizer Z90 particle sizing instrument. Preferably, the particle size is in the range of 1 nm to 100 nm, preferably 1 to 70 nm. The nanoparticles can be organic or inorganic particles. The nanoparticles can also be present as composite particles, such as an inorganic core having organic molecules attached to its surface.

A microparticle is a microscopic particle which has a longest dimension of less than 1 mm but normally more than 100 nm. Sizing methods employing transmission electron microscopy (TEM), scanning electron microscopy (SEM), and quasi-elastic light scattering (QELS) may be used to characterize the microparticle. The microparticles can also be present in the form of microbeads.

The microparticles can be, e.g., coated or uncoated silica-/glass-/biodegradable particles, polystyrene-/coated-/flow cytometry-/PMMA-/melamine-/NIST particles, agarose particles, magnetic particles, coated or uncoated gold particles or silver particles or other metal particles, transition metal particles, biological materials, semiconductors, organic and inorganic particles, fluorescent polystyrene microspheres, non-fluorescent polystyrene microspheres, composite materials, liposomes, cells and the like.

Commercially available microparticles are available in a wide variety of materials, including ceramics, glass, polymers, and metals. Microparticles encountered in daily life include pollen, sand, dust, flour, and powdered sugar. In biological systems, microparticles are small membrane bound vesicles circulating in the blood derived from cells that are in contact with the bloodstream, such as platelets and endothelial cells.

Microbeads are preferably manufactured solid plastic particles of less than 5 millimeters in their largest dimension. Microbeads may also be uniform polymer particles, typically 0.5 to 500 micrometers in diameter.

The term "modified particle" or "modified bead" relates, in particular, to beads or particles which comprise or are linked to molecules, preferably biomolecules. This also comprises the coating of such beads or particles with these (bio)molecules.

Particles or beads according to this invention may be modified in such a way that, for example, biomolecules, e.g., DNA, RNA or proteins, may be able to bind (in some embodiments specifically and/or covalently) to the particles or beads. Therefore, within the scope of this invention is the analysis of characteristics of beads and/or particles and in particular of molecules attached to or linked to such beads or particles. In particular, such molecules are biomolecules. Accordingly, the term "modified (micro)beads/(nano- or micro)particles", in particular, relates to beads or particles which comprise additional molecules to be analyzed or characterized. Modified or non-modified microparticles/(nano- or micro)particles may be able to interact with other particles/molecules such as biomolecules (e.g., DNA, RNA or proteins) in solution.

In the methods of the present invention, labeled particles are employed which are labeled with one or more temperature-sensitive dyes. In the context of this invention, "labeled particles" refer to fluorescently labeled molecules/particles or other molecules/particles which can be detected by fluorescence means, e.g., molecules/particles comprising an intrinsic fluorophore, or particles/molecules with fluorophores attached. In particular, the labeled particles are preferably particles which are attached, e.g., covalently bonded to a dye, or reversibly bonded to a dye over a high affinity protein tag, like polyhistidine-tag, FLAG-tag or similar.

Protein tags are peptide sequences genetically grafted onto a recombinant protein. These include poly(His) tag, polyanionic amino acids, such as FLAG-tag, epitope tags like V5-tag, Myc-tag, HA-tag and NE-tag, tags that may allow specific enzymatic modification (such as biotinylation by biotin ligase) or chemical modification (such as reaction with FlAsH-EDT2 for fluorescence imaging).

Dyes useful in the present invention are dyes which show a temperature-dependent fluorescent intensity, i.e., the fluorescent intensity of the dye increases or decreases when the temperature is changed by cooling or heating. This phenomenon is called temperature-related fluorescence intensity change. In the context of the present invention, dyes which show this behavior are referred to as "temperature-sensitive dyes". Preferably the dyes used in the present invention show not only a temperature induced change in the fluorescence intensity but also a ligand binding induced change in the temperature dependency of their fluorescence intensity when bound to a particle, i.e., labeled particle.

The present inventors have found that the temperature dependency of a dye which is bound to a particle such as a biomolecule can be used to determine the interaction parameters between the ligand and the biomolecule.

Without wishing to be bound by theory, it is believed that this finding is based on the following theoretical principles:

The trans form of cyanine dyes such as Cy5 is fluorescent, whilst the cis form is non-fluorescent. The trans form of cyanine dyes is fluorescent due to resonance or mesomerism caused by delocalized electrons as illustrated below:

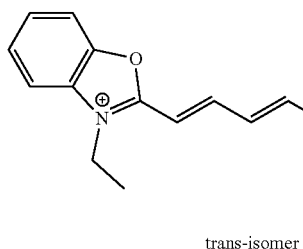

trans-isomer

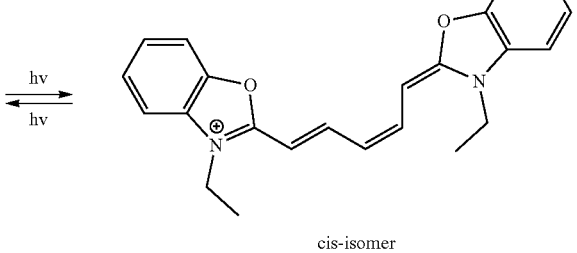

cis-isomer

The fluorescence quantum yield of polymethine dyes depends strongly on the molecular environment in which the probe is located, which determines the efficiency for cis-trans photoisomerization. The fluorescence lifetime depends strongly on the temperature and the solvent viscosity because isomerization is an activated process that involves a large molecular motion. The efficiency of the fluorescence increases significantly when bond rotation is sterically hindered as observed when the dyes are bound to particles such as biomolecules. Dye molecules bound on or within proteins are sterically hindered from the excited-state C=C rotation, and are less likely to convert to the cis isomer. At higher temperatures, the increased vibrational freedom of the dyes bound to the proteins allows for higher rates of conversion to the 'dark' cis state, which results in a decrease in measured fluorescence. As demonstrated by the experiments shown in the examples, the ligand-induced conformational change of a biomolecule modulates the fluorescence intensity of the dye (which is a consequence of changes in vibrational freedom of the dye bound to the protein). Because of this reason, the measurement of the binding affinity at a single temperature is possible. The approach in which solely the temperature dependency of the dye is used to determine the interaction parameters between the ligand and the biomolecule has not been reported before.

Once formed, the photoisomer undergoes a thermal back-isomerisation reaction to yield the thermodynamically stable all-trans isomer. The relative efficiency of photoisomerization with respect to the other two processes depends on the temperature, solvent viscosity and the presence of substituents that might create steric hindrance. Importantly, lower temperatures lead to lower rates of isomerization and higher yield of fluorescence.

Figure 2:
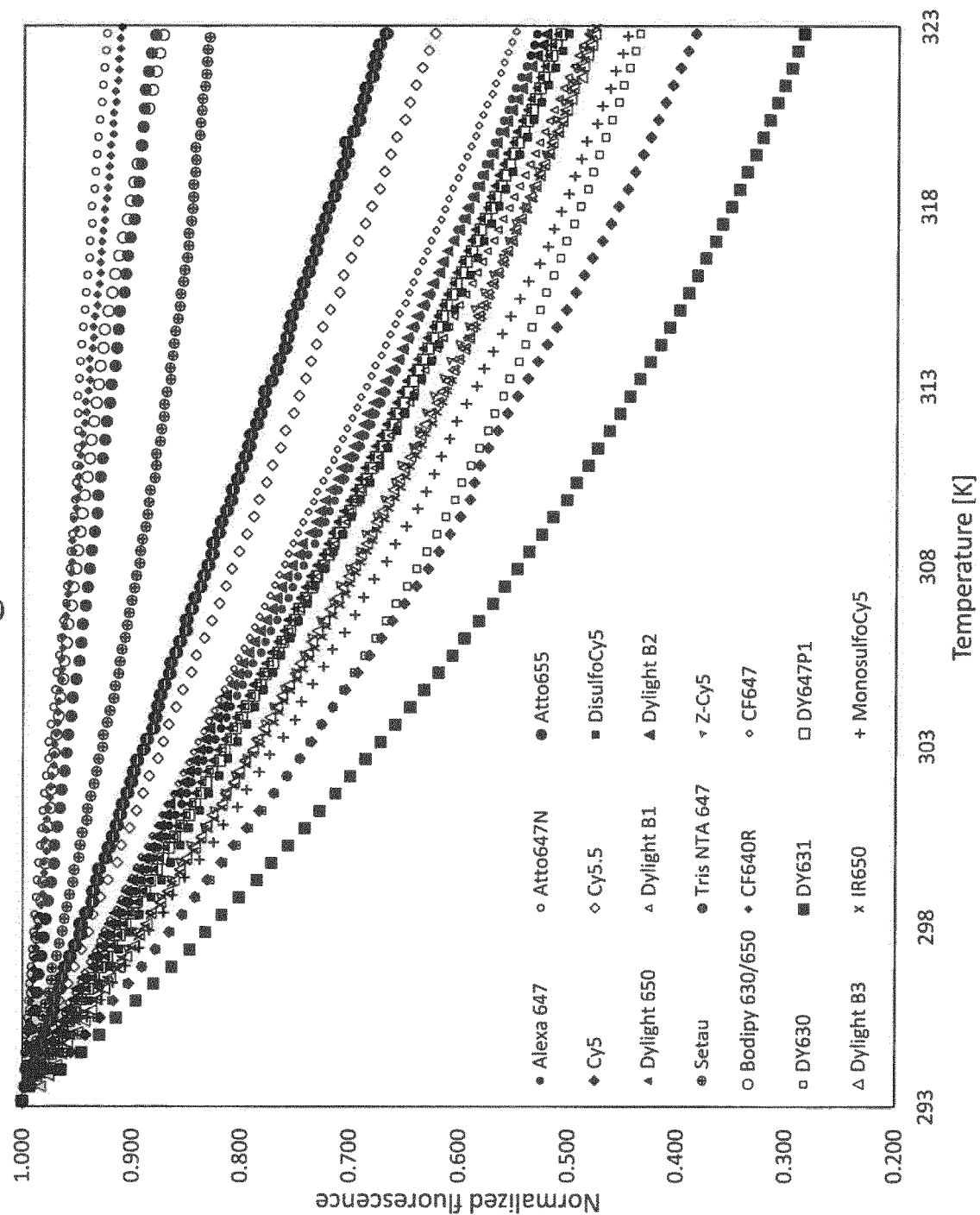
FIG. 2 shows a temperature induced fluorescence intensity change of various dyes using Peltier device as heating source.

The temperature dependency of a dye, i.e., an intrinsic property of the dye to react on the temperature changes with changes in the fluorescence intensity, is solely dependent on the chemical structure of the dye. The temperature dependency of a fluorescent molecule is affected by rotational freedom of its substituent groups. Dyes having a strongly rigidized structure like, but not limited to, ATTO647N, ATTO655 and CF640R respond to an increasing temperature with negligible changes in the fluorescence intensity (FIG. 2). Thus, these dyes are not suitable for the purposes of the present invention. Dyes having a less rigid structure (like, but not limited to, fluorescein, Oregon Green 488, DY495, rhodamine, TAMRA, IR640) show significant decrease in fluorescence intensity upon temperature increase. The most sensitive dyes belong to the family of polymethine dyes (like, but not limited to, Cy3, monosulfoCy3, DY567, Cy5, monosulfoCy5, DY630, DY647P1, DY650, Alexa 647, and DyLight 655 B1-B4). The fluorescence of these dyes is strongly temperature-dependent (FIG. 2).

Figure 15:
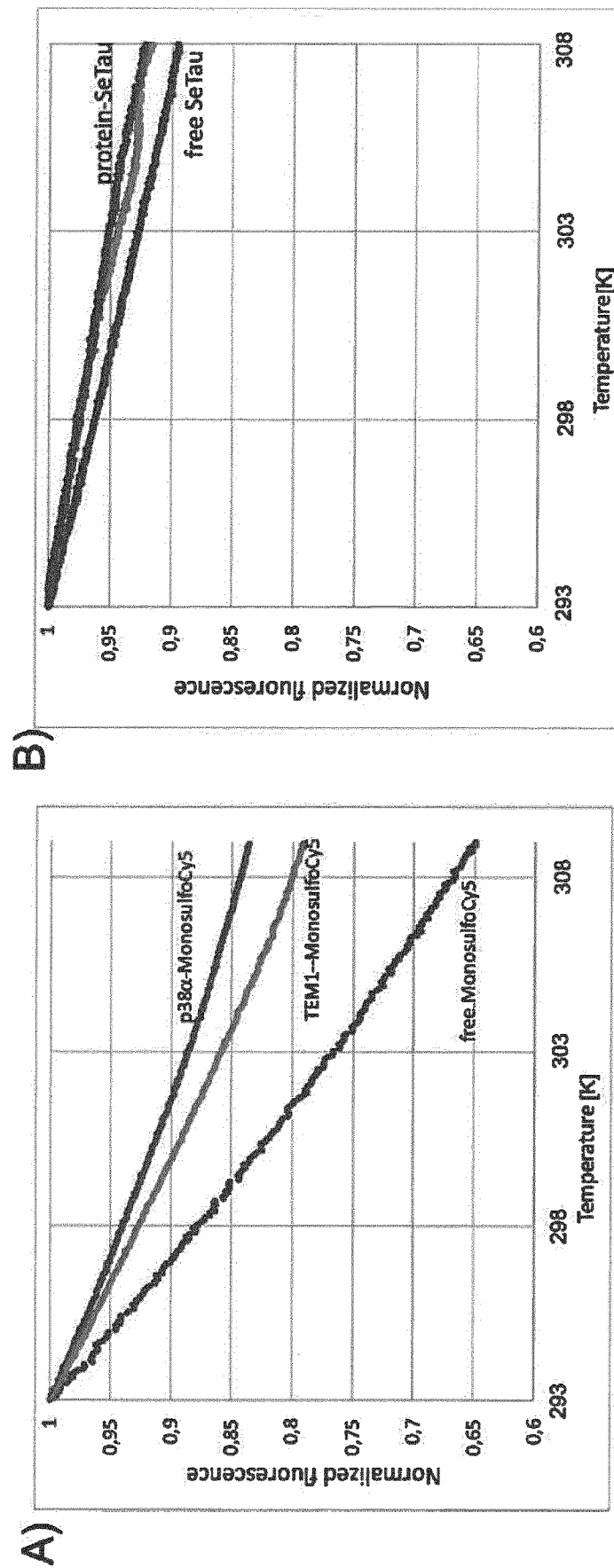
FIG. 15 shows the temperature induced fluorescence intensity change of the dyes MonosulfoCy5 and SeTau alone and conjugated to p38α protein and TEM1 using a Peltier device.

The temperature dependency of dyes is modulated by the conjugation to a particle (biomolecule) resulting in a unique thermo-optical profile (FIG. 15). The temperature-induced fluorescence intensity change is strongly reduced in the presence of a biomolecule as shown for monosulfoCy5 as a representative of polymethine dyes, and it significantly depends on the properties of the biomolecule conjugated to the dye (FIG. 15A). The fluorescence intensity of squaraine rotaxanes like SeTau is much less sensitive to temperature changes. The sensitivity to temperature does not significantly change upon conjugation of SeTau to the biomolecule (FIG. 15B).

Dyes with moderate to strong temperature dependency (like, but not limited to, xanthene dyes (e.g., fluorescein, rhodamine, TAMRA, and DY495) and polymethine dyes (e.g., Cy3, monosulfoCy3, DY547, Cy5, monosulfoCy5, DY630, DY631, and DY647P1) are well suitable for thermo-optical investigations. Their temperature dependency is significantly influenced by the conjugation to the biomolecule.

Dyes having a significant temperature dependency (like, but not limited to, DyLight 655 B3, IR650) may not be suitable for thermo-optical investigations since their temperature sensitivity is not influenced by the conjugation to a biomolecule.

Figure 5:
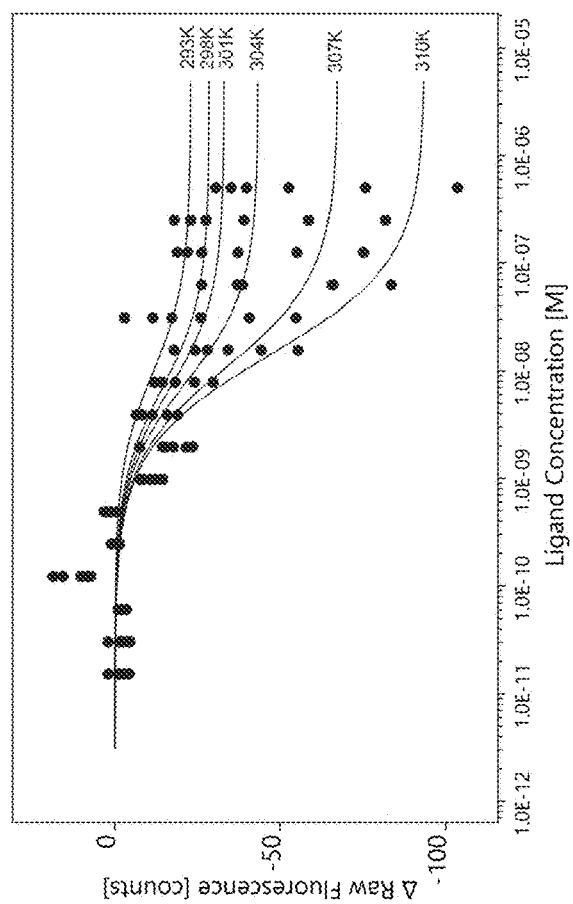
FIG. 5 shows a ligand induced fluorescence intensity change of labeled particles at single elevated temperatures to determine the binding affinity of the ligand BLIP for MonosulfoCy5-TEM1.
Figure 13:
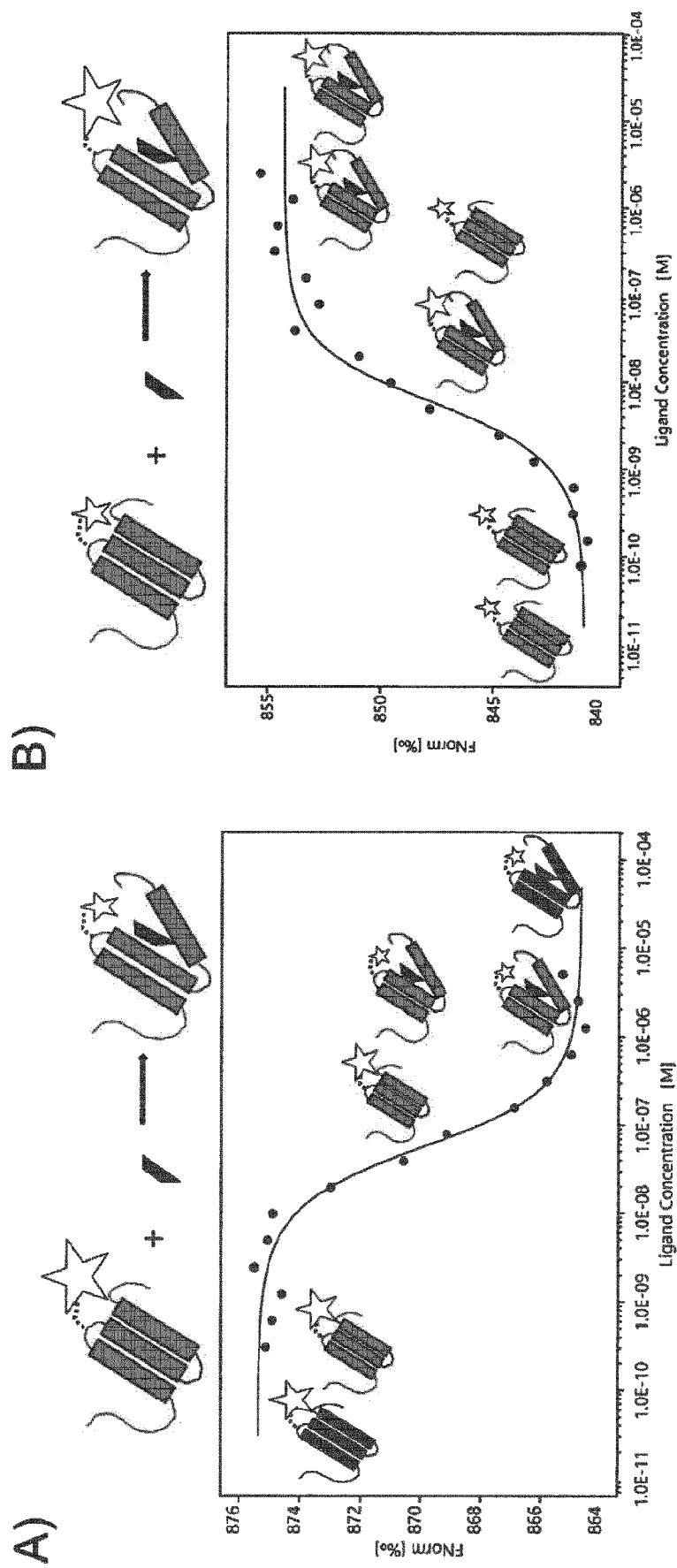
FIG. 13 shows a ligand induced fluorescence intensity change of labeled particles at a single given temperature resulting in a unique thermo-optical profile.

The temperature dependency of a dye that results in a temperature induced fluorescence intensity change is thus required but not sufficient for the optimal dye for thermo-optical studies. The interplay between the dye and the biomolecule uniquely determines the effectiveness and sensitivity of the dye's thermo-optical profile (FIGS. 5 and 13). The present approach in which solely the temperature dependency of the dye is used to determine the interaction parameters between the ligand and the biomolecule has not been described before.

Dyes which can be used in the present invention should demonstrate a temperature dependency in a free form that is preferably >0.3%/K, more preferably >0.5%, and most preferably >1%/K.

The dye's temperature dependency must be modulated by conjugation to a labeled particle. The dye should demonstrate a temperature dependency in a conjugated form that is preferably >0.3%/K, more preferably >0.5%/K, and most preferably >1%/K.

The dye should preferably have low tendency to cause aggregation of labeled particles upon labeling.

Although the incorporation of sulfonate or similar groups into the dyes results in reduced aggregation of labeled biomolecules, a low net charge (preferably ≥−2) of the dye upon conjugation with the biomolecule is preferable for the optimal thermo-optical profile of the dye.

The optimal dye for thermo-optical measurements of ligand↔labeled particle interactions or thermal unfolding of a biomolecule is a member of polymethine dyes (defined as organic compounds containing a chain composed of methine groups (=CH—) with conjugated double bonds), preferably, but not limited to, symmetric and asymmetric cyanine dyes, i.e., a synthetic dye with the general formula $R_2N[CH=CH]_nCH=N^+R_2 \leftrightarrow R_2N^+=CH[CH=CH]_nNR_2$ (wherein n is a small number) in which the nitrogen and optionally a part of the conjugated chain is usually a part of a heterocyclic system such as, but not limited to, imidazole, pyridine, pyrrole, quinoline and thiazole.

The optimal dye for thermo-optical measurements of ligand↔labeled particle interactions or thermal unfolding of the biomolecule may also be a member of xanthene dyes, i.e., an organic compound, which is a derivative of xanthene that includes but is not limited to fluorescein and rhodamine-based dyes, and which is characterized by a rotational freedom of its substituent groups.

Figure 10:
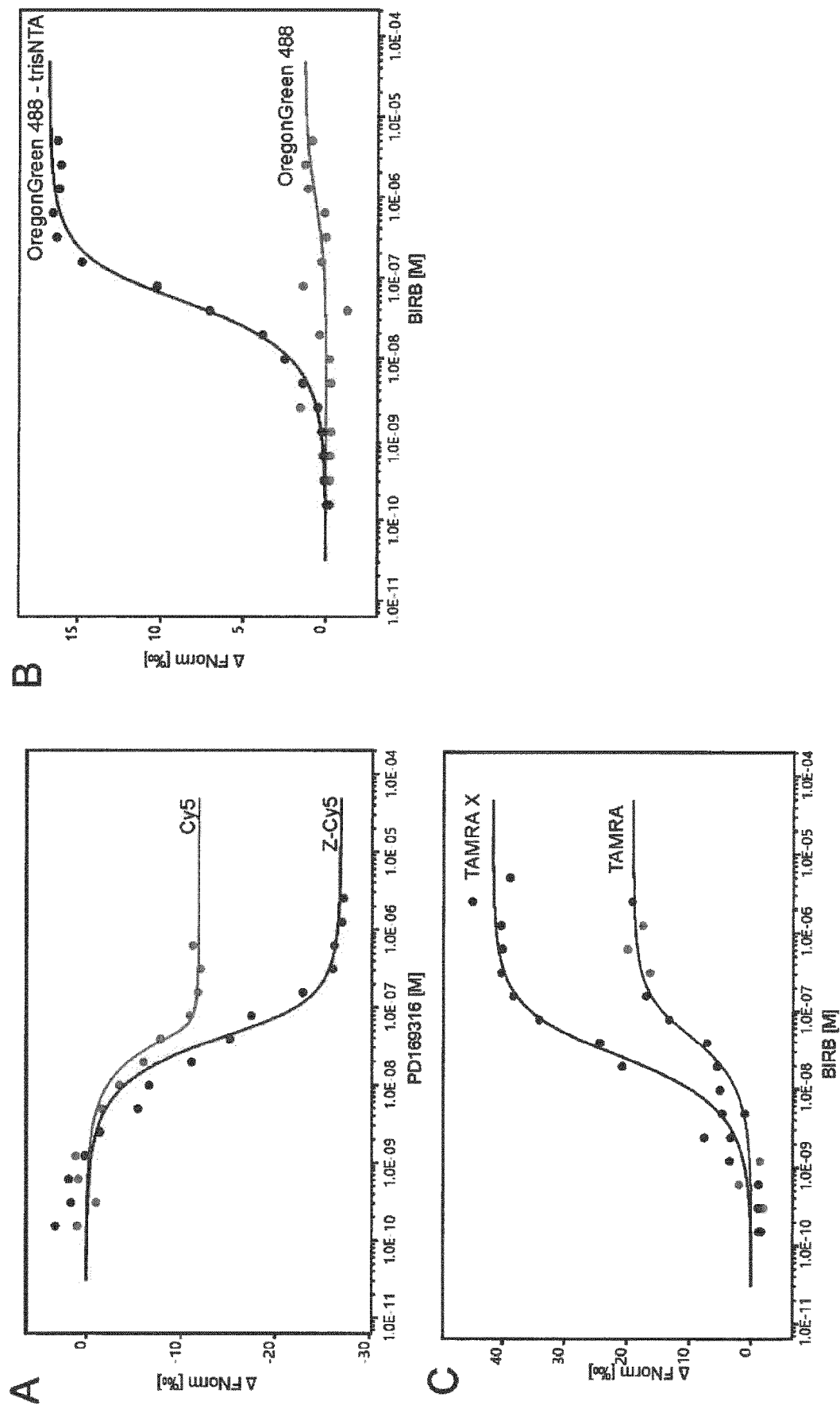
FIG. 10 shows a ligand induced fluorescence intensity change of labeled particles upon heating to determine the binding affinity of the ligand PD169316 and BIRB for p38α protein labeled with Cy5, Z-Cy5, Oregon Green 488, Oregon Green 488-trisNTA, TAMRA or TAMRA X.
Figure 14:
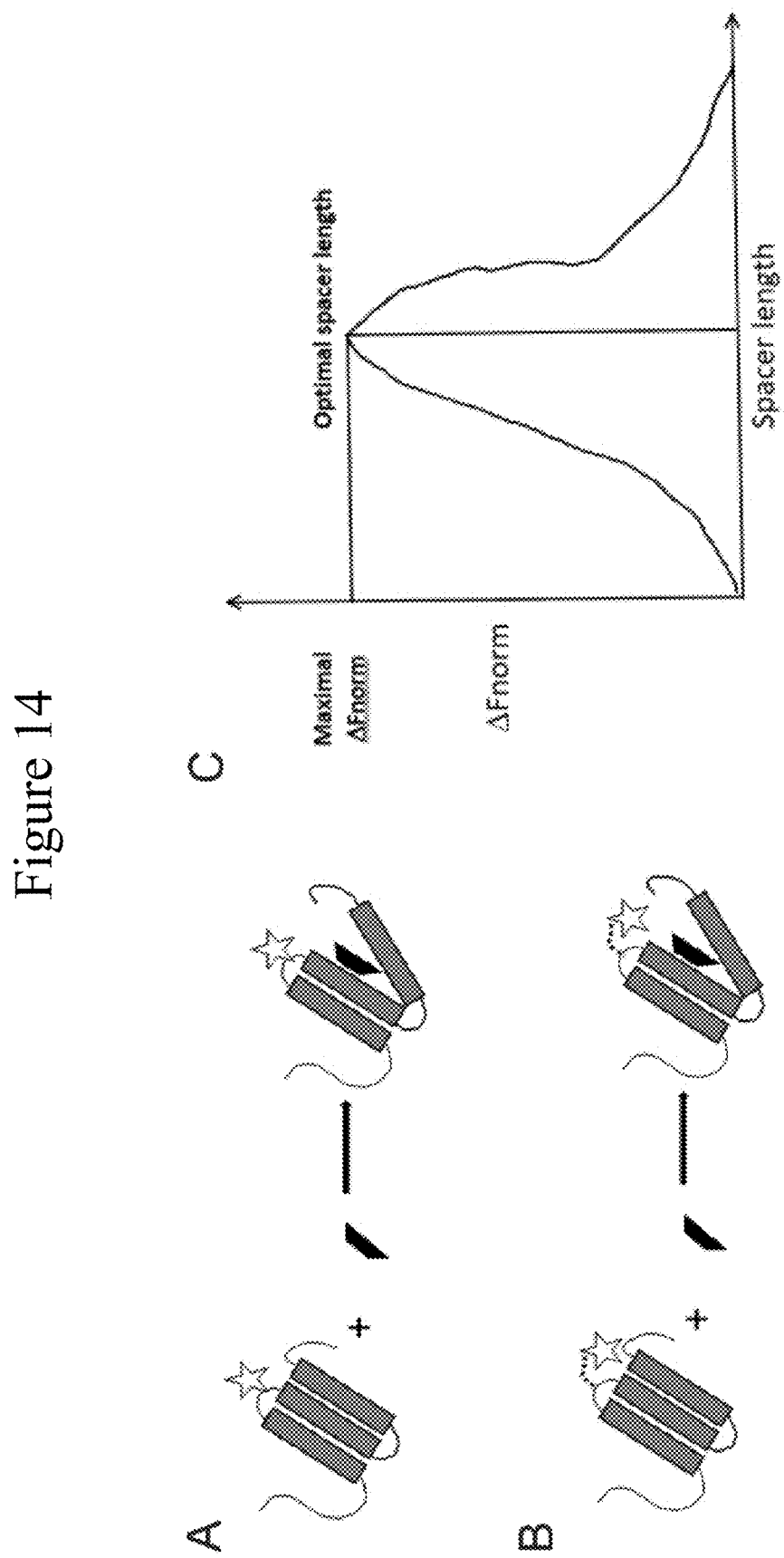
FIG. 14 shows schematically the influence of the spacer length between a dye and a particle on the ligand induced fluorescence intensity change of labeled particles.

The sensitivity of the thermo-optical readout can be manipulated by varying the length and the chemical properties of the spacer between the dye and the biomolecule (FIGS. 10 and 14). Longer linker groups with unique chemical properties such as zwitterionic character in Z-Cy5 contribute to extensive sensing of ligand-induced conformational changes compared to Cy5 with classical hexanoyl spacer (FIG. 10A). Too short spacers like in OregonGreen 488 or TAMRA may prevent efficient sensing of changes in microenvironment due to ligand-induced conformational changes in the biomolecule (FIG. 10B-C). The length and chemical properties of the spacer between the dye and the biomolecule thus determine the sensitivity of the thermo-optical profiling. The spacer length that governs the distance between the dye and the biomolecule upon conjugation should most preferably be longer than two $CH_2$ groups.

Figure 8:
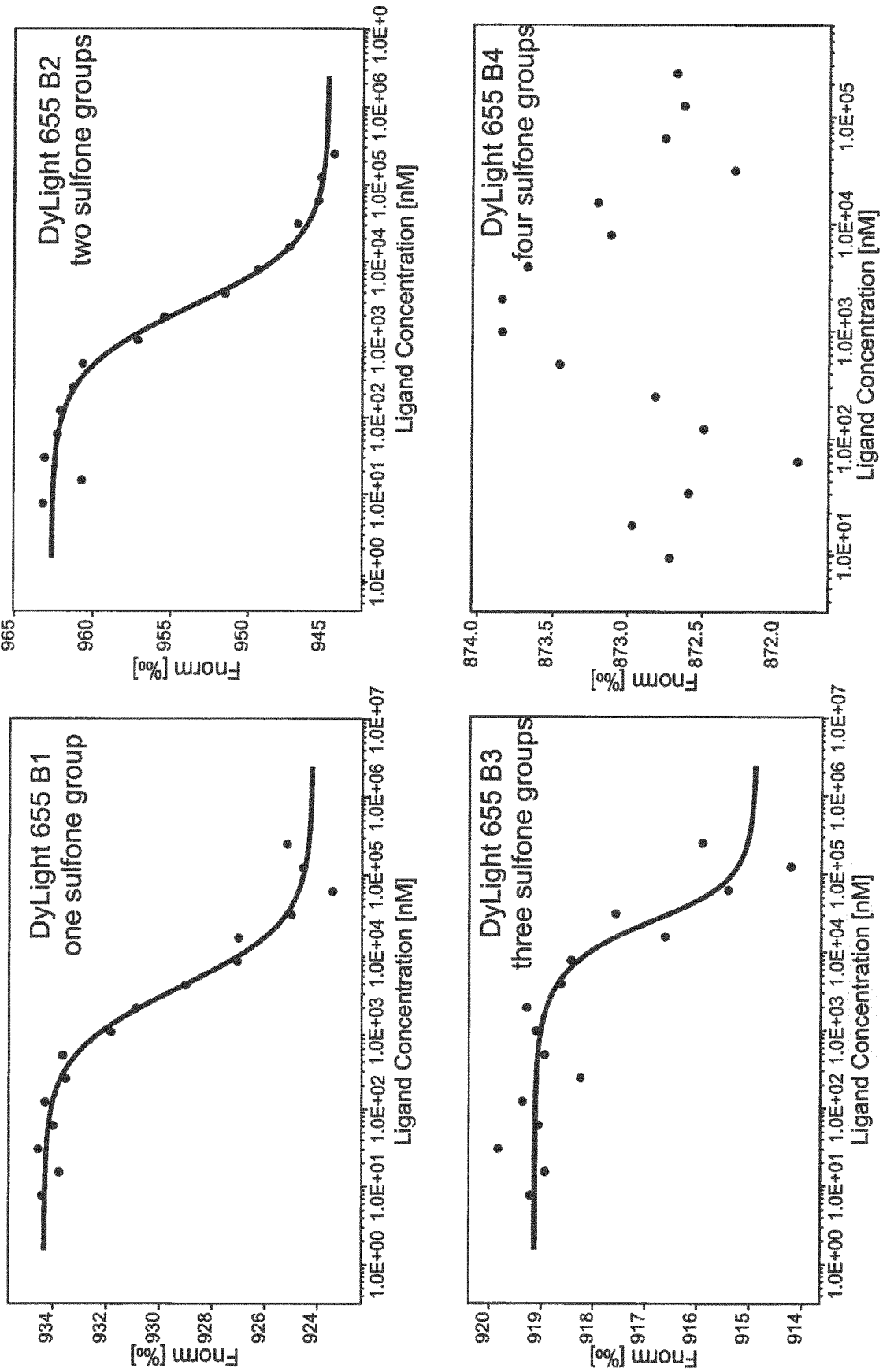
FIG. 8 shows a ligand induced fluorescence intensity change of labeled particles at 37° C. to determine the binding affinity of the ligand Anakinra for IL-R1 protein labeled with DyLight655 B1 to B4.
Figure 11:
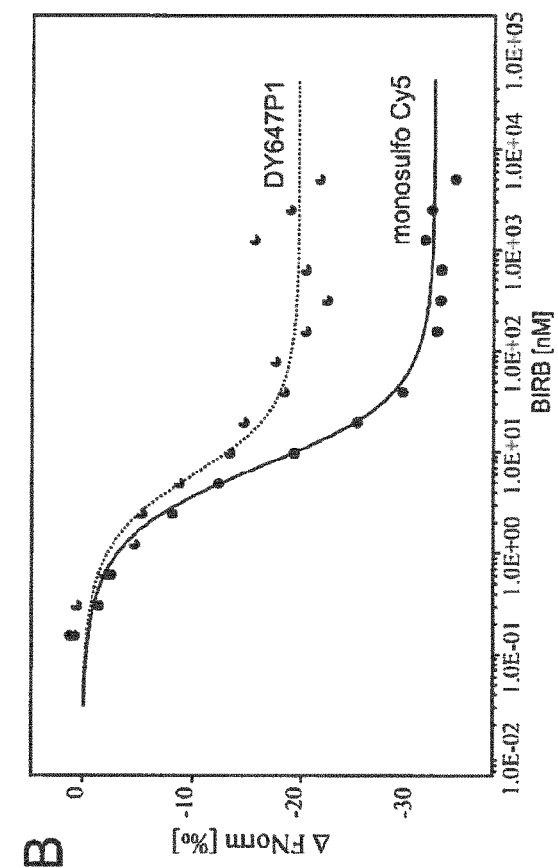
FIG. 11 shows a ligand induced fluorescence intensity change of labeled particles upon heating between 37° C. and 45° C. to determine the binding affinity of the ligand BLIP for TEM1 and of the ligand BIRB for p38α protein, being labeled with monosulfoCy5 or DY647P1.
Figure 11:
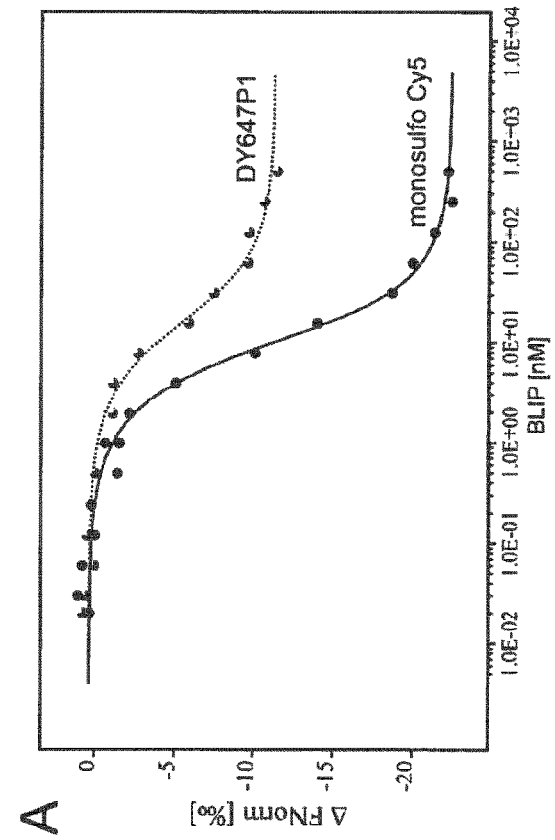

The modulation of the dye's temperature dependency by the biomolecule is dependent on the net charge the dye exhibits after the conjugation to the biomolecule. An increasing number of sulfonate groups negatively correlates with the quality of thermo-optical readout (FIG. 8) as demonstrated with the experiments, in which IL-R1 was labeled with polymethine dyes containing a benzopyrylium core and various number of sulfonate groups. The affinity of the ligand Anakinra for labeled IL-R1 was determined. Larger (>2) number of sulfonate groups reduced the applicability of the dye for thermo-optical profiling. A similar effect is shown by the comparison of the carbocyanine dyes monosulfoCy5 and DY647P1 that carry one and two sulfonate groups, respectively, which illustrates that the number of sulfonate group crucially determines the applicability of the dye for thermo-optical studies (FIG. 11).

Figure 12:
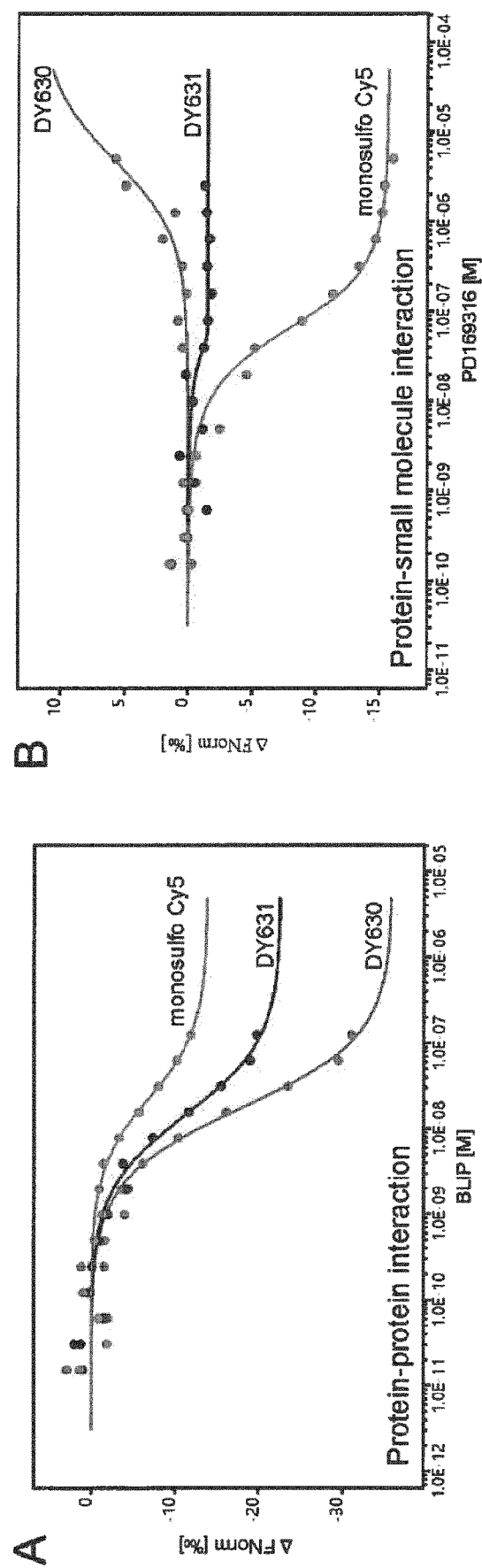
FIG. 12 shows a ligand induced fluorescence intensity change of labeled particles upon heating between 37° C. and 45° C. to determine the binding affinity of the ligand BLIP for TEM1 and of the ligand PD169316 for p38α protein, being labeled with monosulfoCy5, DY630 or DY631.

Specific dyes may be used for specific applications to achieve the best signal-to-noise ratio. The noise is defined as variations in the thermo-optical signal that are not caused by binding of a ligand. As shown in the FIG. 12, the asymmetric polymethine dyes DY630 and DY631 are superior in the assay that detects protein-protein interaction (FIG. 12A), but show poor thermo-optical profile in the assay that detects the binding of small molecule to the protein (FIG. 12B). On the other hand, the symmetric carbocyanine dye monosulfo Cy5 shows a superior profile in an assay that detects the binding of small molecule to the protein.

Temperature-sensitive dyes which can be used in the present invention are preferably selected from the group consisting of polymethine dyes and xanthene dyes. Polymethine dyes preferably include symmetric and asymmetric cyanine dyes or polymethine dyes having a benzopyrylium core. Xanthene dyes include rhodamine dyes and fluorescein dyes.

Preferred polymethine dyes having a benzopyrylium core include, but are not limited to, Chromeo P543, DY630, DY631, DY650, DyLight 655 B2, DyLight 655 B3. Preferred cyanine dyes include, but are not limited to, Cyanine 2, Cy3, Monosulfo Cy3, Cy5, Monosulfo Cy5 (version 1), Monosulfo Cy5 (version 2), Disulfo Cy5, Z-Cy2, Z-Cy5, Monosulfo Z-Cy5, Alexa647, DY547P1 and DY647P1. Preferred xanthene dyes include, but are not limited to, TAMRA, TAMRA X, DY495, and Oregon Green. More preferred xanthene dyes include, but are not limited to, TAMRA X, and DY495.

Especially preferred dyes are DY630, DY631, DyLight 655 B2, DyLight 655 B3, Cyanine 2, Z-Cy2, Z-Cy5, Monosulfo Cy5 (version 1), Monosulfo Cy5 (version 2), and TAMRA X. FIGS. 19a to 19e show structural formulae of the dyes mentioned above. In FIGS. 19a to 19e, the dyes are shown, sometimes as pure dyes without spacer group, sometimes as reactive dyes including spacer and reactive group.

According to the first aspect of the present, invention the labeled particles are preferably labeled with one or more dyes selected from the group consisting of dyes represented by general formulae (I), (IIa), (IIb) or (III):

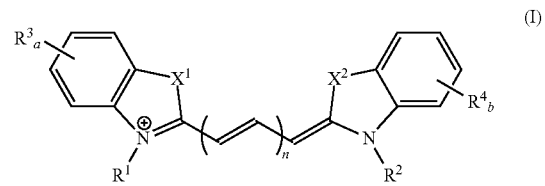
(I)

wherein $X^1$ is O, S or $CR^5R^6$;

$X^2$ is O, S or $CR^7R^8$;

$R^1$ and $R^2$ are each independently selected from the group consisting of hydrogen, and alkyl groups which may be substituted;

$R^3$, $R^4$, $R^5$, $R^6$, $R^7$ and $R^8$ are each independently selected from the group consisting of hydroxy, carboxy, sulfonic acid, thiol or a salt thereof, hydrogen, halogen, carboxylate ester groups which may be substituted, nitro group, amines, amides, alkyl groups which may be substituted (preferably $C_{1-4}$ alkyl), alkoxy groups which may be substituted, and alkenyl groups which may be substituted;

with the proviso that at least one of $R^1$, $R^2$, $R^3$, $R^4$, $R^5$, $R^6$, $R^7$ and $R^8$ is a spacer group by which the dye is conjugated to the particle, wherein the spacer group is longer than two $CH_2$-groups;

a is an integer from 0 to 4;
b is an integer from 0 to 4; and
n is an integer from 1 to 3, preferably 1 or 2;

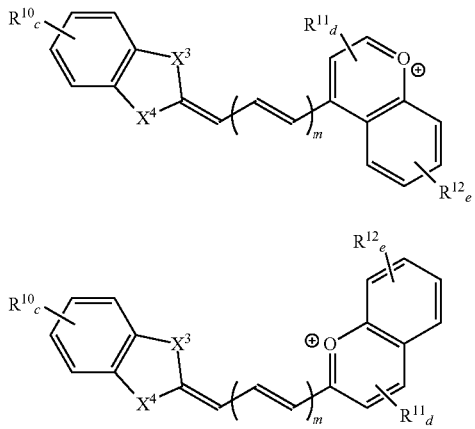

wherein
one of $X^3$ and $X^4$ is $NR^9$ and the other of $X^3$ and $X^4$ is O, S or $CR^{13}R^{14}$;
$R^9$ is selected from the group consisting of hydrogen, and alkyl groups which may be substituted;
$R^{10}$, $R^{11}$, $R^{12}$, $R^{13}$ and $R^{14}$ are each independently selected from the group consisting of hydroxy, carboxy, sulfonic acid, thiol or a salt thereof, hydrogen, halogen, carboxylate ester groups which may be substituted, nitro group, amines, amides, alkyl groups which may be substituted (preferably $C_{1-4}$ alkyl), alkoxy groups which may be substituted, and alkenyl groups which may be substituted;
with the proviso that at least one of $R^9$, $R^{10}$, $R^{11}$, $R^{12}$, $R^{13}$ and $R^{14}$ is a spacer group by which the dye is conjugated to the particle, wherein the spacer group is longer than two $CH_2$-groups;
c is an integer from 0 to 4;
d is an integer from 0 to 2;
e is an integer from 0 to 4; and
m is an integer from 1 to 3, preferably 1 or 2; and

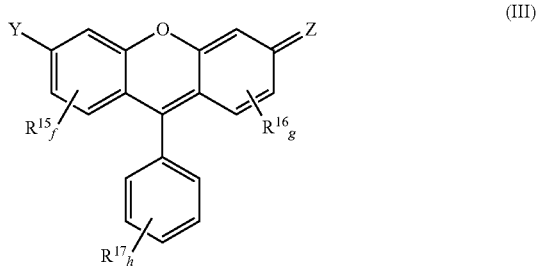

wherein
Y is $OR^{18}$ or $NR^{19}R^{20}$;
Z is O or $NR^{21}R^{22}$;
$R^{15}$, $R^{16}$ and $R^{17}$ are each independently selected from the group consisting of hydroxy, carboxy, sulfonic acid, thiol or a salt thereof, hydrogen, halogen, carboxylate ester groups which may be substituted, nitro group, amines, amides, alkyl groups which may be substituted (preferably $C_{1-4}$ alkyl), alkoxy groups which may be substituted, and alkenyl groups which may be substituted;
with the proviso that at least one of $R^{17}$ is a spacer group by which the dye is conjugated to the particle;
$R^{18}$ is H or an alkali metal ion,
$R^{19}$, $R^{20}$, $R^{21}$ and $R^{22}$ are each independently selected from the group consisting of hydrogen, and alkyl groups which may be substituted, preferably, $R^{19}$, $R^{20}$, $R^{21}$ and $R^{22}$ are each the same;
f is an integer from 0 to 3;
g is an integer from 0 to 3; and
h is an integer from 1 to 5.

The alkyl group of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{19}$, $R^{20}$, $R^{21}$ and $R^{22}$ is preferably a $C_{1-4}$ alkyl group which may be substituted, like, but not limited to, methyl, ethyl, propyl, n-butyl, tert-butyl, methoxyethyl.

The groups $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{19}$, $R^{20}$, $R^{21}$ and $R^{22}$ do preferably not contain large groups like aryl groups which introduce large steric hindrance which may disturb the fluorescence intensity change upon binding of the ligand to the labeled particle.

The alkenyl group of $R^3$, $R^4$, $R^5$, $R^6$, $R^7$, $R^8$, $R^{10}$, $R^{11}$, $R^{12}$, $R^{13}$, $R^{14}$, $R^{15}$, $R^{16}$, and $R^{17}$ is preferably a $C_{1-4}$ alkenyl group which may be substituted. The alkoxy group of $R^3$, $R^4$, $R^5$, $R^6$, $R^7$, $R^8$, $R^{10}$, $R^{11}$, $R^{12}$, $R^{13}$, $R^{14}$, $R^{15}$, $R^{16}$, and $R^{17}$ is preferably a $C_{1-4}$ alkoxy group which may be substituted.

The alkyl group of $R^1$ and $R^2$ may be substituted with one or more substituents selected from the group consisting of alkoxy and sulfonate, preferably methoxy and sulfonate.

The carboxylate ester group, alkyl group, alkenyl group or alkoxy group of $R^3$, $R^4$, $R^5$, $R^6$, $R^7$ and $R^8$ may be substituted with one or more substituents selected from the group consisting of oxo groups and sulfonates, preferably with no substituents.

The alkyl group of $R^9$ may be substituted with the same substituents as the alkyl group of $R^1$ and $R^2$ and may preferably be substituted with one or more sulfonate groups.

The carboxylate ester group, alkyl group, alkenyl group or alkoxy group of $R^{10}$, $R^{11}$, $R^{12}$, $R^{13}$ and $R^{14}$ may be substituted with the same substituents as the alkyl group, alkenyl group or alkoxy group of $R^3$, $R^4$, $R^5$, $R^6$, $R^7$ and $R^8$ and may preferably be substituted with one or more alkyl groups, preferably methyl groups.

The carboxylate ester group, alkyl group, alkenyl group or alkoxy group of $R^{15}$, $R^{16}$ and $R^{17}$ may be substituted with the same substituents as the alkyl group, alkenyl group or alkoxy group of $R^3$, $R^4$, $R^5$, $R^6$, $R^7$ and $R^8$ and may preferably have no substituents.

The alkyl group of $R^{19}$, $R^{20}$, $R^{21}$ and $R^{22}$ may be substituted with the same substituents as the alkyl group of $R^1$ and $R^2$ and may preferably have no substituents.

The spacer group is a group by which the dye is conjugated to the particle. Most preferably the spacer group is longer than two $CH_2$ groups, such as a hexanoyl spacer group.

In the context of the present invention, the terms "sulfonic acid" and "sulfonate group" are used interchangeably and refer to the group "—$SO_3^-$". As will be understood by a person skilled in the art, this group is negatively charged. This negative charge requires either a corresponding positive charge within the labeled particle (internal salt) or a corresponding positive ion must be present in the solution. The positive ion can be any ion which is soluble in the solution comprising the labeled particles and can preferably be selected from ammonium ions, alkali metal ions and alkaline earth metal ions, most preferably sodium or potassium ions. Likewise, a labeled particle having an overall positive charge requires a corresponding negative ion in the solution. The negative ion can be any ion which is soluble in the solution comprising the labeled particles and can preferably be selected from halogenide ions, sulfate ions, hexafluorophosphate and tetrafluoroborate ions.

The dyes of formula (I) are preferably dyes represented by general formula (I'):

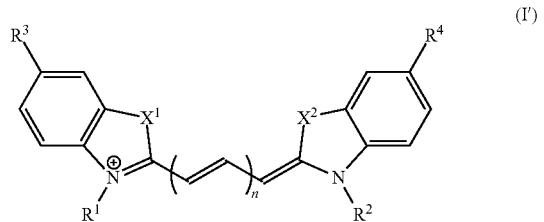

(I')

wherein
$X^1$ is O or $CR^5R^6$;
$X^2$ is O or $CR^7R^8$;
$R^1$, $R^2$, $R^5$, $R^6$, $R^7$ and $R^8$ are each independently a $C_{1-20}$ alkyl group which may be substituted;
$R^3$ and $R^4$ are each independently selected from the group consisting of hydrogen, and sulfonic acid or a salt thereof;
with the proviso that one of $R^1$, $R^2$, $R^5$, $R^6$, $R^7$ and $R^8$ is a spacer group by which the dye is conjugated to the particle, wherein the spacer group is longer than two $CH_2$-groups; and
n is an integer equal to 1 or 2.

The dyes of formula (IIa) or (IIb) are preferably dyes represented by general formula (IIa') or (IIb'):

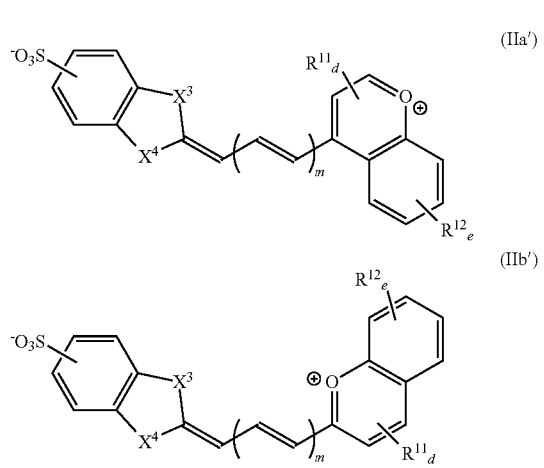

wherein
one of $X^3$ and $X^4$ is $NR^9$ and the other of $X^3$ and $X^4$ is $CR^{13}R^{14}$;
the sulfonate group is in 4-position with respect to $NR^9$;
$R^9$ is a $C_1$-$C_{20}$ alkyl group which may be substituted;
$R^{11}$, $R^{12}$, $R^{13}$ and $R^{14}$ are each independently selected from the group consisting of hydroxy, carboxy, sulfonic acid, thiol or a salt thereof, hydrogen, halogen, carboxylate ester groups which may be substituted, nitro group, amines, amides, alkyl groups which may be substituted (preferably $C_{1-4}$ alkyl), alkoxy groups which may be substituted, and alkenyl groups which may be substituted;
with the proviso that one of $R^9$, $R^{13}$ and $R^{14}$ is a spacer group by which the dye is conjugated to the particle, wherein the spacer group is longer than two $CH_2$-groups;
d is an integer from 0 to 2;
e is an integer from 0 to 3; and
m is an integer equal to 1 or 2.

Even more preferably, the dyes of formula (IIa') or (IIb') are dyes represented by general formula (IIa") or (IIb"):

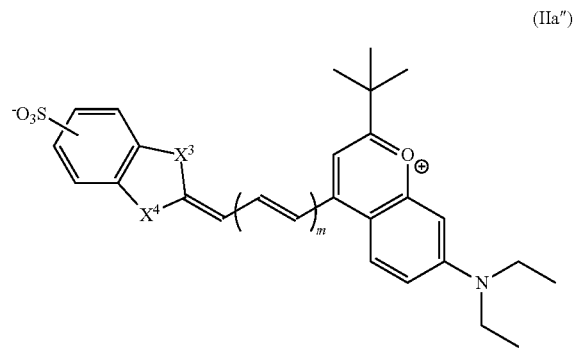

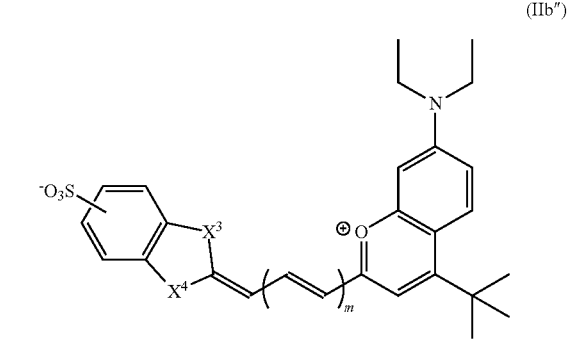

wherein
one of $X^3$ and $X^4$ is $NR^9$ and the other of $X^3$ and $X^4$ is $CR^{13}R^{14}$;
the sulfonate group is in 4-position with respect to $NR^9$;
$R^9$ is a $C_{3-6}$ alkyl group which may be substituted;
$R^{13}$ and $R^{14}$ are each independently a $C_{1-4}$ alkyl group which may be substituted; with the proviso that one of $R^9$, $R^{13}$ and $R^{14}$ is a spacer group by which the dye is conjugated to the particle, wherein the spacer group is longer than two $CH_2$-groups; and
m is an integer equal to 1 or 2.

The dyes of formula (III) are preferably dyes represented by general formula (III'):

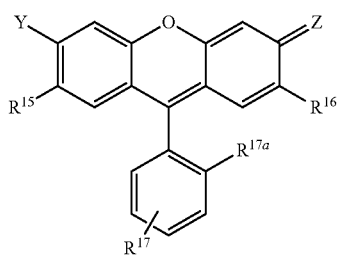

(III')

wherein
Y is OH or $N(CH_3)_2$;
Z is O or $^+N(CH_3)_2$;
$R^{15}$ and $R^{16}$ are each independently hydrogen, or a halogen;
$R^{17}$ is a spacer group by which the dye is conjugated to the particle; and
$R^{17a}$ is a carboxy group, or a salt thereof.

Preferably, the spacer group in said dyes of general formulae (I), (I'), (IIa), (IIb), (IIa'), (IIb'), (IIa") or (IIb") is a $C_4$ to $C_{20}$ alkylene chain, which may be substituted, wherein one or more carbon atoms of the alkylene chain may independently be replaced by alicyclic groups, aryl groups, heterocyclic groups, heteroaryl groups, or heteroatoms selected from the group consisting of O, N, and S. More preferably, the dyes of general formulae (I'), (IIa'), (IIb'), (IIa") or (IIb") comprise this preferred spacer group. Even more preferably the dyes of general formulae (I'), (IIa'), (IIb'), (IIa") or (IIb") comprise this preferred spacer group conjugated to a biomolecule, preferably conjugated to a protein.

Even more preferably, the spacer group of general formulae (I), (I'), (IIa), (IIb), (IIa'), (IIb'), (IIa") or (IIb") is a $C_4$ to $C_6$ alkylene chain, which may be substituted, wherein one carbon atom may be replaced by one aryl group. Even more preferably, the dyes of general formulae (I'), (IIa'), (IIb'), (IIa") or (IIb") comprise this even more preferred spacer group. Most preferably the dyes of general formulae (I'), (IIa'), (IIb'), (IIa") or (IIb") comprise this even more preferred spacer group conjugated to a biomolecule, preferably conjugated to a protein.

Preferably, the spacer group in said dyes of general formulae (III) or (III') is a $C_2$ to $C_{10}$ alkylene chain, which may be substituted, wherein one or more carbon atoms of the alkylene chain may independently be replaced by alicyclic groups, aryl groups, heteroaryl groups, heterocyclic groups, or heteroatoms selected from the group consisting of O, N, and S. More preferably, the dyes of general formula (III') comprise this preferred spacer group. Even more preferably, the dyes of general formula (III') comprise this preferred spacer group conjugated to a biomolecule, preferably conjugated to a protein.

Even more preferably, the spacer group in said dyes of general formulae (III) or (III') is a $C_3$ to $C_7$ alkylene chain, which may be substituted, wherein one or more carbon atoms of the alkylene chain may independently be replaced by heteroatoms selected from the group consisting of O, N, and S. Even more preferably, the dyes of general formula (III') comprise this even more preferred spacer group. Most preferably, the dyes of general formula (III') comprise this even more preferred spacer group conjugated to a biomolecule, preferably conjugated to a protein.

The dyes of general formulae (III) or (III') may also comprise a spacer group as defined with respect to the spacer group of the dyes of general formulae (I'), (IIa'), (IIb'), (IIa") or (IIb").

The spacer group of general formulae (I), (I'), (IIa), (IIb), (IIa'), (IIb'), (IIa"), (IIb"), (III) or (III') does usually not contain two consecutive heteroatoms. The spacer group of any of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{17}$ is usually a group, which is bound to the dye structure via a methylene group, i.e., the spacer group $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{17}$ starts at the end, which is proximate to the dye structure, with a methylene group. The far end of the spacer group, i.e., the end of the spacer group which is attached to the particle, is often a carbonyl group. Furthermore, the spacer group of general formulae (I), (I'), (IIa), (IIb), (IIa'), (IIb'), (IIa"), (IIb"), (III) or (III') is preferably a $C_4$ to $C_{20}$ alkylene chain, which may be substituted, wherein one or more carbon atoms of the alkylene chain may independently be replaced by heteroatoms selected from the group consisting of O, N, and S, wherein the far end of the spacer group is a TrisNTA-Ni complex, which comprises three Ni(II) ions. In other words, the spacer group is attached to the dye as exemplarily shown in FIG. 19e for TrisNTA647 and trisNTA Oregon Green 488. The TrisNTA conjugates to the particle via the Ni ions.

The substituents of the spacer group of general formulae (I), (I'), (IIa), (IIb), (IIa'), (IIb'), (IIa"), (IIb"), (III) or (III') may be selected from oxo groups, $C_{1-4}$ alkylenesulfonates, and $C_{1-4}$ alkyl.

The $C_4$ to $C_{20}$ alkylene chain of the spacer group of general formulae (I), (I'), (IIa), (IIb), (IIa'), (IIb'), (IIa") or (IIb") may be substituted with one or more substituents selected from the group consisting of oxo groups, $C_{1-4}$ alkylenesulfonates, and $C_{1-4}$ alkyl, preferably oxo groups, methylenesulfonates, and $C_{1-4}$ alkyl.

The $C_4$ to $C_6$ alkylene chain of the spacer group of general formulae (I), (I'), (IIa), (IIb), (IIa'), (IIb'), (IIa") or (IIb") may be substituted with the same substituents as the respective $C_4$ to $C_{20}$ alkylene chain and may preferably be substituted with one or more substituents selected from the group consisting of oxo groups.

The optional N-heteroatom in the above $C_4$ to $C_{20}$ alkylene chain of general formulae (I), (I'), (IIa), (IIb), (IIa'), (IIb'), (IIa") or (IIb") may be substituted with a substituent selected from the group consisting of hydrogen and $C_{1-4}$ alkyl.

The $C_2$ to $C_{10}$ alkylene chain of the spacer group of general formulae (III) or (III') may be substituted with one or more substituents selected from the group consisting of oxo groups and $C_{1-4}$ alkyl, preferably oxo groups.

The optional N-heteroatom in the above $C_2$ to $C_{10}$ alkylene chain of general formulae (III) or (III') may be substituted with one or more substituents selected from the group consisting of hydrogen and $C_{1-4}$ alkyl, preferably hydrogen.

The optional alicyclic groups, aryl groups, heteroaryl groups, heterocyclic groups in the alkylene chain of the spacer groups of general formulae (I), (I'), (IIa), (IIb), (IIa'), (IIb'), (IIa"), (IIb"), (III) or (III') may be substituted with one or more substituents selected from the group consisting of oxo groups, and $C_{1-4}$ alkyl, preferably oxo groups.

The dyes can be obtained from Dyomics, Thermo Fischer Scientific, Lumiprobe, Cyandye or Kerafast. Alternatively, the dyes employed in the present invention can be prepared by known methods. Specific methods of preparing benzopyrylium dyes such as DY631 are described in U.S. Pat. No.

6,924,372 B2; the preparation of DY647P1 and monosulfo DY647P1 is described in US 2013/0251637 A9; the synthesis of dyes such as Z-Cy5 is described in U.S. Pat. No. 8,197,758 B2; and a method of preparing monosulfoCy5 is provided in U.S. Pat. No. 5,268,486. These documents are hereby incorporated by reference in their entirety.

The labeled particles can be formed by reacting the particle (such as a biomolecule) with a reactive dye having a reactive group that enables the conjugation of the dye to the particle. A particularly preferred reactive group is an N-hydroxysuccinimide activated ester (NHS) group, which was used in the Examples. However, the reactive group is not limited to NHS, but other groups that enable the conjugation of the dye to the particle may be employed such as maleimide, amide, sulfonamide, urea, and thiourea formation with N-hydroxysuccinimide activated esters, sulfonyl chlorides, isocyanates, isothiocyanates, azides, alkynes, hydrazide, carboxylic acid and amine groups. In principle, any modification of the dye that enables its conjugation to the biomolecule can be employed. Methods of modifying biomolecules have been studied by E. M. Sletten and C. R. Bertozzi in Angew. Chem. Int. Ed. Engl. 2009; 48(38): 6974-6998, which is hereby incorporated by reference in its entirety.

An exemplary general protein labeling procedure comprises the following steps:
1. preparing the particle in a corresponding labeling buffer;
2. adding the dye and mixing it with the particle;
3. incubating for a given period of time in the dark at the given temperature (most of the time either on ice, RT or 37° C.); and
4. removing non-bound dye by purification methods like, but not limited to, gel chromatography, size-exclusion chromatography; as the elution buffer the assay buffer may be used.

For the labeling of protein-tags the removal of free dye is usually not needed due to stoichiometric labeling ratio, in which all dye is being bound to the tag.

Since the dye shall be attached to the particle via a spacer group, the above mentioned reactive group is usually attached to the other end of the spacer group in the reactive dye, i.e., a spacer group is attached at one end to the dye and at the other end to the reactive group. After reaction of the reactive dye having a reactive group with the particle, the dye is attached to the particle via the spacer group.

The reactive dyes can be provided in a protein labeling kit. Each kit may contain material sufficient for multiple protein labeling reactions, such as 2 to 8, preferably 3 to 5 protein labeling reactions. Depending on the amount of protein used, enough material for approximately 1000 microscale experiments can be provided.

The labeling kit includes as a main component the reactive dye. Preferably, the kit may include more than one dye as in the fifth aspect of the present invention, such as 2 or 3 different dyes, more preferably 2 different dyes separately. The protein labeling kit preferably further comprises an instruction manual explaining the use of the kit in at least one of the methods of the present invention.

Additionally, the kit often further includes at least one selected from the group consisting of buffer exchange columns, purification columns, labeling buffers, adapters, and combinations thereof.

Ligand binding to a target biomolecule like a protein can result in a wide range of conformational changes such as amino acid side chain, loop or domain movement. The ligand which can be used in the first aspect of the present invention can be (but not limited to) selected from the group consisting of ions, metals, compounds, drug fragments (small chemical fragments, which may bind only weakly to the biological target), carbohydrates, small molecules such as ATP (organic compounds having a low molecular weight (<900 Daltons); small molecules may help regulate a biological process and usually have a size on the order of 1 nm), drugs, prodrugs, lipids, biomolecules, proteins such as chemokine and cytokine, peptides, peptoids, enzymes, antigens, cofactors, nucleic acids, aptamers, inhibitors, Fc receptors, ssDNA, nanoparticles, liposomes, unilamellar vesicles (including small unilamellar vesicles (SUV) and giant unilamellar vesicles (GUV)), polymers, organic molecules, inorganic molecules, metal complexes, hormones, flavors, odorants, particles and (micro)beads. Preferably, the ligands are selected from the group consisting of ions, metals, compounds, drug fragments carbohydrates, small molecules, drugs, prodrugs, lipids, proteins, peptides, peptoids, enzymes, nucleic acids, aptamers, hormones, flavors, and odorants.

In the following, particle-ligand combinations are shown using the notation "particle→ligand", i.e., the particle is shown on the left hand side of the arrow and the corresponding ligand is shown on the right hand side of the arrow.

Preferred particle→ligand combinations are selected from the group consisting of enzyme→lipid, receptor→hormone, receptor→chemokine, enzyme→inhibitor, receptor→neurotransmitter, receptor→cytokine, enzyme→ion, receptor→ion, receptor→amino acid, enzyme→cofactor, receptor→lipid, receptor→sterol, enzyme→fragment, receptor→peptide, receptor→fragment, enzyme→metabolite, receptor→receptor, receptor→glycolipid, enzyme→DNA, receptor→odorant, receptor→prodrug, enzyme→RNA, receptor→drug, enzyme→mono-/di- or polysaccharide, enzyme→fatty acid, enzyme→vitamin, enzyme→prodrug, enzyme→drug, liposome→protein, transporter protein→substrate, antibody→antigen, viral particle→receptor, virus-structural protein, antibody→Fc receptor, chaperone→ATP, ssDNA→ssDNA, aptamer→ligand, chaperone→ions, RNA→small molecule, polysaccharide→small molecule, chaperon→protein, DNA→small molecule, structural protein→structural protein, signaling protein→signaling protein, signaling protein→small molecule, signaling protein→prodrug, signaling protein→drug, signaling protein→lipid, structural protein→ions, nanoparticle→protein, cellular organelle→protein, nanoparticle→DNA, cellular organelle→lipid, nanoparticle→RNA. More preferred particle→ligand combinations are selected from the group consisting of enzyme→lipid, receptor→hormone, receptor→chemokine, enzyme→inhibitor, receptor→neurotransmitter, receptor→cytokine, enzyme→ion, receptor→ion, receptor→amino acid, enzyme→cofactor, receptor→lipid, receptor→sterol, enzyme→fragment, receptor→peptide, receptor→fragment, enzyme→metabolite, receptor→receptor, receptor→glycolipid, enzyme→DNA, receptor→odorant, receptor→prodrug, enzyme→RNA, receptor→drug, enzyme→mono-/di- or polysaccharide, enzyme→fatty acid, enzyme→vitamin, enzyme→prodrug, enzyme→drug, liposome→protein, transporter protein→substrate, antibody→antigen, viral particle→receptor, virus→structural protein, antibody→Fc receptor, chaperone→ATP, ssDNA→ssDNA, aptamer→ligand, chaperone→ions, RNA→small molecule, chaperone→protein, DNA→small molecule, structural protein→structural protein, signaling protein→signaling protein, signaling protein→small molecule, signaling protein→prodrug, signaling protein→drug, signaling protein→lipid, structural protein→ions.

The most preferred particle→ligand combinations are selected from the group consisting of enzyme→lipid, receptor→hormone, receptor→chemokine, enzyme→inhibitor, receptor→neurotransmitter, receptor→cytokine, enzyme→ion, receptor→ion, receptor→amino acid, enzyme→cofactor, receptor→lipid, receptor→sterol, enzyme→fragment, receptor→peptide, receptor→fragment, enzyme→metabolite, receptor→receptor, receptor→eglycolipid, enzyme→DNA, receptor→odorant, receptor→prodrug, enzyme→RNA, receptor→drug, enzyme→mono-/di- or polysaccharide, enzyme→fatty acid, enzyme→vitamin, enzyme→prodrug, enzyme→drug, liposome→protein, transporter protein→substrate, antibody→antigen, antibody→Fc receptor, chaperone→ATP, ssDNA→ssDNA, aptamer→ligand, chaperone→ions, RNA→small molecule, chaperone→protein, DNA→small molecule, structural protein→structural protein, signaling protein→signaling protein, signaling protein→small molecule, signaling protein→prodrug, signaling protein→drug, signaling protein→lipid, structural protein→ions. In the above most preferred particle→ligand combinations, the particles and ligands preferably stem from eukaryotic cells, more preferably from human, mouse, rat, or primate cells; or pathogens like Plasmodium ssp., Trypanosoma ssp., Vibrio ssp., Salmonella ssp., Mycobacterium tubercolosis and viruses like Zika, Ebola, Marburg virus, Nipah, Severe Acute Respiratory Syndrome (SARS), Middle East respiratory syndrome coronavirus (MERS-CoV), Crimean-Congo hemorrhagic fever (CCHF), Rift Valley fever (RVF), HIV.

Figure 4:
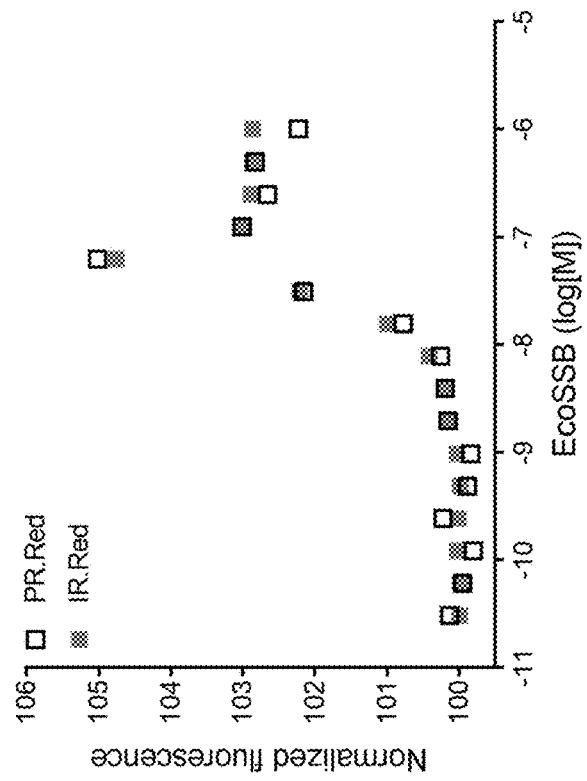
FIG. 4 shows a ligand induced fluorescence intensity change of labeled particles using Peltier device or IR laser as heating source to determine the binding affinity of the ligand EcoSSB for Cy5-ssDNA.
Figure 9:
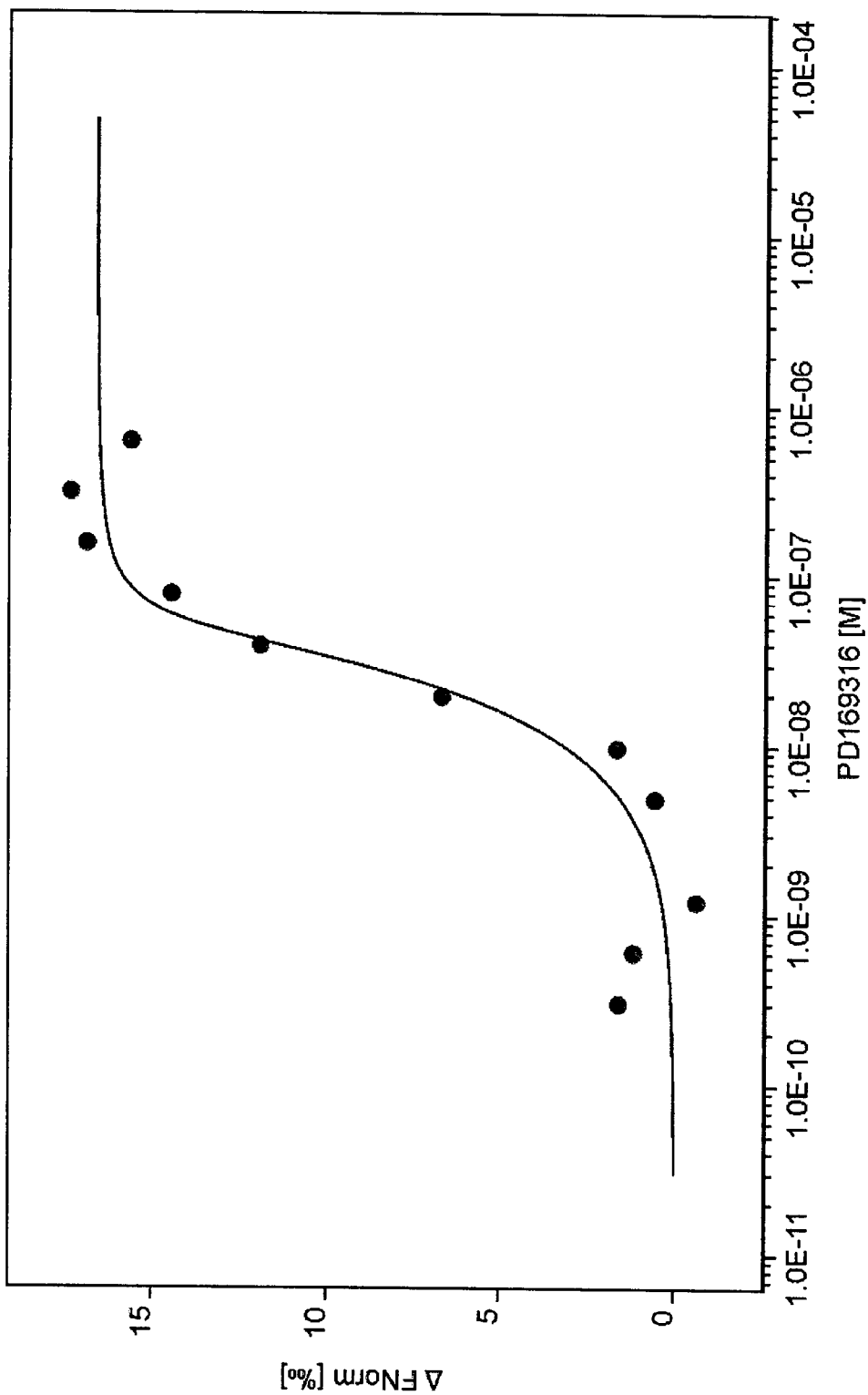
FIG. 9 shows a ligand induced fluorescence intensity change of labeled particles upon cooling between 35° C. and 23° C. to determine the binding affinity of the ligand PD169316 for p38α protein labeled with Cy5.

Because the temperature dependency of the dye is influenced by the local environment in which the dye resides, it is expected that the ligand-induced conformational changes will translate into a unique thermo-optical profile dependent on the concentration of the ligand present in the system (FIG. 13). As shown for the binding of Cy5-ssDNA to the protein EcoSSB (i.e. Escherichia coli single-stranded DNA-binding protein, FIG. 4), the modulation of the temperature dependency of the dye by the local environment in which the dye resides may be used for determination of binding affinity using the thenno-optical approach and either Peltier device or IR laser as a heating source (FIG. 4). The thenno-optical approach can be also by applied when the probe is cooled down. As shown in FIG. 9, the probe was preheated with the IR-laser and the temperature induced fluorescence change monitored upon cooling. As additional sources of cooling Peltier devices, cooling fluids or gases (including air) can be used.

Figure 16:
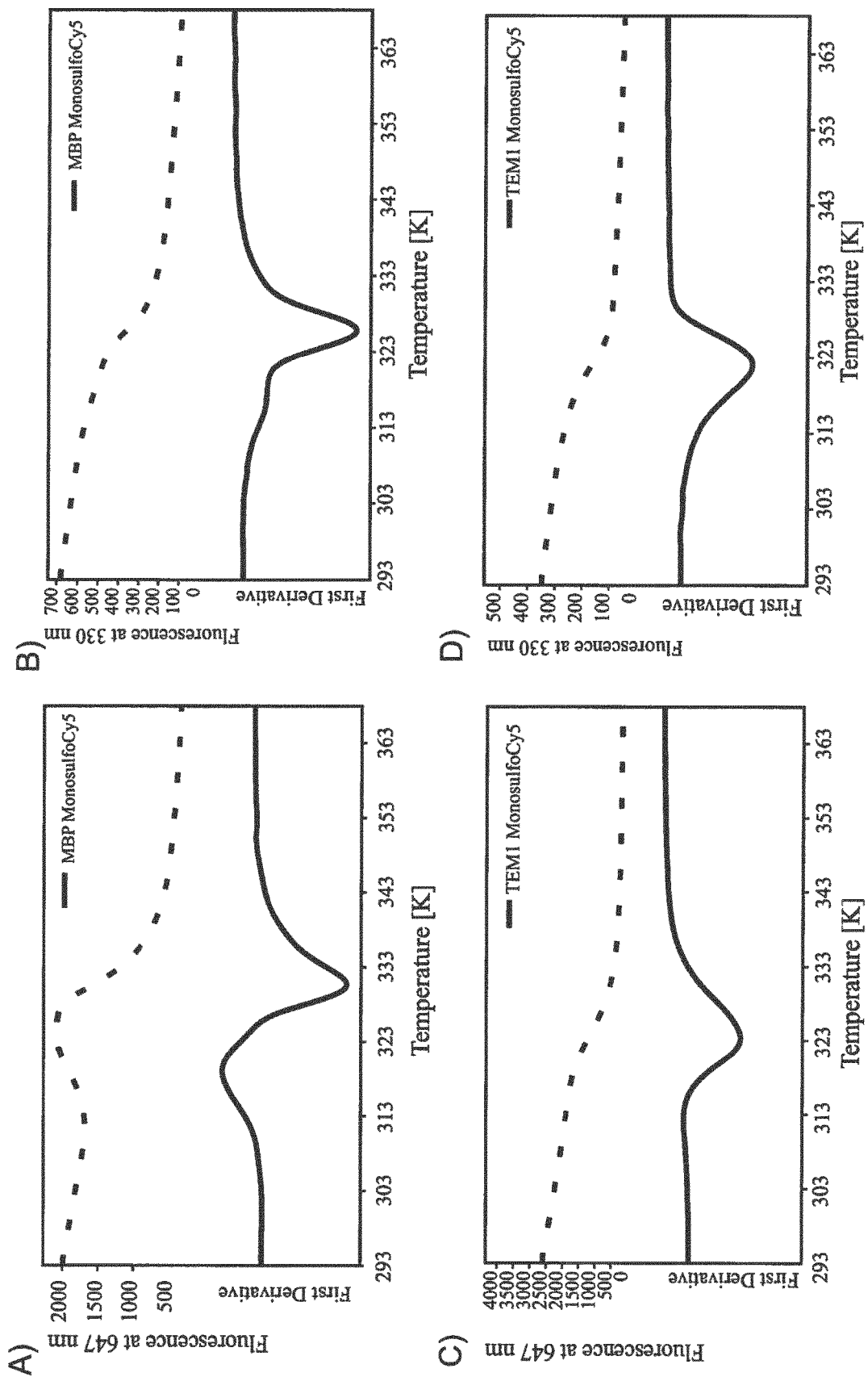
FIG. 16 shows the temperature induced fluorescence intensity change of onosulfoCy5 conjugated to MBK and TEM1 to determine thermal unfolding.

Thermal unfolding of biomolecules like proteins is characterized by large conformational changes. Because the temperature dependency of the dye is influenced by the local microenvironment and this environment changes upon unfolding, the thermo-optical approach may be used to determine the melting temperature of the biomolecule as shown for MBP and TEM1 (FIG. 16).

The sample to be used in the method of the first aspect of the present invention is a solution comprising the labeled particles and the ligands. Herein, the labeled particles can be dissolved or dispersed in the solution. Alternatively, the labeled particles can be immobilized on a solid support which is brought into contact with the solution containing the ligands. Preferably, the labeled particles are dissolved or dispersed in the solution. The aqueous solution is preferably adjusted to a pH value of 2 to 10, more preferably 4 to 10, even more preferably 5 to 9, most preferably 6 to 8.5, using a buffer.

In the first aspect of the present invention, the preferred concentration of the labeled particles in the solution is from 10 picomolar to 1 micromolar, more preferably 100 picomolar to 100 nanomolar. The concentration of the ligand is preferably from 0.01 picomolar to 1 molar, more preferably 1 picomolar to 100 millimolar, even more preferably 10 picomolar to 10 millimolar.

The sample is provided in a sample chamber preferably selected from the group consisting of a multi-well plates, a microfluidic chip, a capillary, a cuvette, a reaction tube, a pipette tip, microfluidics, droplets and a translucent container. The translucent container can be a glass container or a plastic container.

It is advantageous to provide the sample probe within a chamber which has a thickness in direction of the fluorescence excitation beam from 1 μm to 500 μm, in particular 1 μm to 250 μm, in particular 1 μm to 100 μm, in particular 3 μm to 50 μm, in particular 5 μm to 30 μm. A person skilled in the art will understand that the term chamber also relates to e.g. a capillary, microfluidic chip or multi-well plate.

It is understood by the person skilled in the art that the term "fluorescence" as employed herein is not limited to "fluorescence" per se but that the herein disclosed means, methods and devices may also be used and employed by usage of other means, in particular luminescence, such as phosphorescence. Accordingly, the term "exciting fluorescently said labeled particles and firstly detecting and/or measuring fluorescence of said excited particles" relates to the "excitation step" in the above identified method and may comprise the corresponding excitation of luminescence, i.e., excitation is carried out with a shorter wave length than detection of the following emission. Therefore, the term "detecting and/or measuring secondly a fluorescence of the particles" in context of this invention means a step of detection said emission after excitation. The person skilled in the art is aware that in the context of this invention the "excitation" wave length and the "emission" wave length have to be separated.

Means exciting fluorescently the labeled particles and detecting the fluorescence of the excited particles are not limited and any suitable means known to the skilled person may be employed.

According to the present invention, preferable means for exciting, preferably fluorescently exciting the labeled particles/molecules may be any suitable device selected from the group consisting of laser, fibre laser, diode-laser, LED, Halogen, LED-Array, HBO (HBO lamps are, e.g., short arc lamps in which the discharge arc fires in an atmosphere of mercury vapour under high pressure), HXP (HXP lamps are, e.g., short arc lamps in which the discharge arc burns in an atmosphere of mercury vapour at very high pressure. E.g., in contrast to HBO lamps they are operated at a substantially higher pressure and they employ halogen cycle. HXP lamps generate UV and visible light, including significant portion of red light).

According to the present invention, preferable means for detecting the excited particles, particularly for detecting the fluorescence, in the solution may be any suitable device selected from the group consisting of CCD camera (2D or line-scan CCD), Line-Camera, Photomultiplier Tube (PMT), Avalanche Photodiode (APD), CMOS-Camera.

The methods of the present invention may be carried out in any suitable device. Preferably, the method may be carried out using one of the following devices: Monolith NT.115 G/R MO-G009, Monolith NT.115 R/B MO-G008, Monolith NT.115 B/G MO-007, or Monolith NT.115 Pico MO-006, but is not limited thereto.

In a second aspect, the present invention relates to a method for measuring inter- and/or intra-molecular interactions. The method of the second aspect comprises the following steps:
  a) providing a sample comprising labeled particles;
  b) exciting fluorescently the labeled particles and detecting a first fluorescence of the excited particles at a first temperature;
  c) heating or cooling the sample to a second temperature;
  d) exciting fluorescently the labeled particles and detecting a second fluorescence of the excited particles at the second temperature;
  e) characterizing inter- and/or intra-molecular interactions and/or modifications/alterations of the particles based on the first and second fluorescence.

The method of the second aspect of the present invention encompasses, but is not limited to, ligand-to-labeled-particle binding interactions as in the first aspect of the present invention. Further, the method of the second aspect of the present invention includes methods of measuring chemical reactions (like inorganic or organic reactions, including glycosylation, phosphorylation, lipidation, carbonylation, oxidation of particles) as well as complex formations and/or their dissociation.

In a third aspect, the present invention relates to a method for measuring time dependent changes. The method of the third aspect comprises the following steps:
  a) providing a sample comprising labeled particles;
  b) exciting fluorescently the labeled particles and detecting a first fluorescence of the excited particles;
  c) waiting for a predetermined time;
  d) exciting fluorescently the labeled particles and detecting a second fluorescence of the excited particles;
  e) characterizing the time dependent change of the particles based on the first and second fluorescence.

The method of the third aspect of the present invention is useful for measuring time dependent changes of the labeled particles, e.g., for kinetic measurements of conformational changes, binding kinetics, or stability measurements or for quality control measurements.

In a fourth aspect, the present invention relates to a method for measuring environmental dependent changes. The method of the fourth aspect comprises the following steps:
  a) providing a first sample comprising labeled particles;
  b) exciting fluorescently the labeled particles and detecting a first fluorescence of the excited particles in the first sample;
  c) providing a second sample comprising the labeled particles at substantially the same concentration, wherein the second sample differs from the first sample;
  d) exciting fluorescently the labeled particles and detecting a second fluorescence of the excited particles in the second sample;
  e) characterizing the environmental dependent change of the particles based on the first and second fluorescence.

The method of the fourth aspect of the present invention can be used to determine influences of environmental changes on the labeled particles. Such environmental changes include, but are not limited to, pH changes, temperature changes, pressure changes, changes of the solvent, changes in the concentration of other solutes such as salts, and the like.

In the methods of the second, third and fourth aspects of the present invention, the same labeled particles labeled with the same dyes are employed as in the first aspect of the present invention. The term interaction is used in the same way as in the first aspect of the present invention. The temperatures at which the methods of the second, third and fourth aspects of the present invention are carried out preferably correspond to the predetermined temperatures of the first aspect of the present invention. The temperature difference in the second aspect of the present invention is preferably the same as in the first aspect of the present invention. The same applies to the heating and cooling methods. The concentration of the labeled particles in the sample solution in the second, third and fourth aspects of the present invention is preferably the same as in the first aspect of the present invention. The preferred particle-ligand combinations in the second, third and fourth aspects of the present invention is preferably the same as in the first aspect of the present invention. Also the same sample chambers may be employed. The means for fluorescently exciting the labeled particles and for detecting the excited particles in the second, third and fourth aspects of the present invention are preferably also the same as in the first aspect of the present invention.

The U.S. Pat. No. 9,676,787 B2 discloses certain benzopyrylium compounds and their use in labeling of biomolecules. In this document, ligands were only detected. A dilution series was solely made to show an improved detection range of the disclosed benzopyrylium dyes compared to pre-existing dyes. In principle a single ligand concentration would have been sufficient to demonstrate this effect. Thus, it was solely demonstrated that the dyes in question are suitable for standard applications such as immunoblots. There, the fluorescence intensity depends on the number of fluorophores remaining in the measured sample. In detail, this document describes the following procedure:
  (a) Antigens (ligands) in a solution with a defined concentration are bound to a surface.
  (b) The antigen solution is removed and the surface is washed.
  (c) Subsequently, antibodies labeled with the fluorescent dyes were added to the surface and incubated.
  (d) The solution containing the labeled antibodies is removed and the surface is washed.
  (e) The fluorescence of antibodies bound to the surface via antigens is detected.
  (f) The temperature at which the experiments are carried out is not described. However, a careful control of the temperature was not needed as the fluorescence changes are big.

A skilled person reading U.S. Pat. No. 9,676,787 B2 would assume that the fluorescence intensity change stems from the fact that more or less antibody is bound to the surface at the time of fluorescence detection as there was more or less antigen to bind to. It is implied that each antibody shows the same fluorescence intensity, no matter whether a ligand is bound or not. Additionally, for detection of an antigen, a single concentration of antigen is sufficient.

This is fundamentally different form the present invention.

In the method of the present invention, binding constants between ligands and particles can be detected and not simply the presence of ligands. Thus, already at the beginning of the assay, the concentration of ligand and particle are predefined. The main difference is, that the change in fluorescence intensity that is measured does not stem from a change of the amount of fluorescently labeled particle but from a change of brightness of the fluorescent dye which senses the environment and thus the brightness changes depending on the binding status of the particle. In detail, the present invention differs from the above document as follows (a) The amount of particle and ligand in each fluorescent measurement is predefined and not changed, e.g. by washing steps.
(b) Each labels (fluorophores) brightness depends on whether or not the labeled particle is bound to a ligand.
(c) The temperature is carefully controlled, as the expected fluorescence changes can be very small and can be masked by small temperature-dependent fluorescence changes.

In the present invention, the fluorescence change does not stem from a different amount of fluorescent particle, but from a change in fluorescence intensity of the individual particles based on whether or not a ligand is bound. In particular, the fluorescence can increase or decrease when a ligand is bound to the labeled (fluorescent) particle. Determining a binding constant (termed $K_d$ or $K_a$) requires a dilution series. Furthermore, both ligand and particle are present during the fluorescence measurement in the same concentration as predefined. There are no washing steps.

The present invention is summarized in the following items:

1. A method for measuring interactions between labeled particles and ligands comprising the steps:
   a) providing a sample comprising labeled particles and ligands in a solution, wherein the labeled particles are dissolved or dispersed in the solution or are immobilized on a solid support;
   b) exciting fluorescently the labeled particles and detecting the fluorescence of the excited particles at a predetermined temperature;
   c) repeating steps (a) and (b) multiple times at different concentrations of the ligands in the solution; and
   d) determining the interaction between the labeled particles and the ligands based on the ligand concentration dependent change of the fluorescence of the labeled particles,
   wherein the labeled particles are labeled with one or more dyes selected from the group consisting of dyes represented by general formulae (I), (IIa), (IIb) or (III):

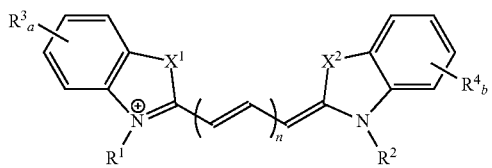

wherein
$X^1$ is O, S or $CR^5R^6$;
$X^2$ is O, S or $CR^7R^8$;
$R^1$ and $R^2$ are each independently selected from the group consisting of hydrogen, and alkyl groups which may be substituted;
$R^3$, $R^4$, $R^5$, $R^6$, $R^7$ and $R^8$ are each independently selected from the group consisting of hydroxy, carboxy, sulfonic acid, thiol or a salt thereof, hydrogen, halogen, carboxylate ester groups which may be substituted, nitro group, amines, amides, alkyl groups which may be substituted (preferably $C_{1-4}$ alkyl), alkoxy groups which may be substituted, and alkenyl groups which may be substituted;

with the proviso that at least one of $R^1$, $R^2$, $R^3$, $R^4$, $R^5$, $R^6$, $R^7$ and $R^8$ is a spacer group by which the dye is conjugated to the particle, wherein the spacer group is longer than two $CH_2$-groups;
a is an integer from 0 to 4;
b is an integer from 0 to 4; and
n is an integer from 1 to 3, preferably 1 or 2;

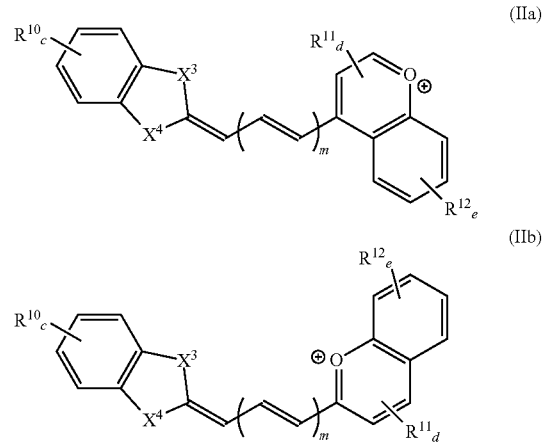

wherein
one of $X^3$ and $X^4$ is $NR^9$ and the other of $X^3$ and $X^4$ is O, S or $CR^{13}R^{14}$;
$R^9$ is selected from the group consisting of hydrogen, and alkyl groups which may be substituted;
$R^{10}$, $R^{11}$, $R^{12}$, $R^{13}$ and $R^{14}$ are each independently selected from the group consisting of hydroxy, carboxy, sulfonic acid, thiol or a salt thereof, hydrogen, halogen, carboxylate ester groups which may be substituted, nitro group, amines, amides, alkyl groups which may be substituted (preferably $C_{1-4}$ alkyl), alkoxy groups which may be substituted, and alkenyl groups which may be substituted;
with the proviso that at least one of $R^9$, $R^{10}$, $R^{11}$, $R^{12}$, $R^{13}$ and $R^{14}$ is a spacer group by which the dye is conjugated to the particle, wherein the spacer group is longer than two $CH_2$-groups;
c is an integer from 0 to 4;
d is an integer from 0 to 2;
e is an integer from 0 to 4; and
m is an integer from 1 to 3, preferably 1 or 2; and

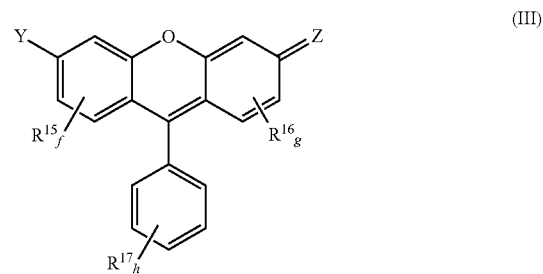

wherein
Y is $OR^{18}$ or $NR^{19}R^{20}$;
Z is O or $^+NR^{21}R^{22}$;
$R^{15}$, $R^{16}$ and $R^{17}$ are each independently selected from the group consisting of hydroxy, carboxy, sulfonic acid, thiol or a salt thereof, hydrogen, halogen, carboxylate ester groups which may be substituted, nitro group, amines, amides, alkyl groups which may be substituted (preferably $C_{1-4}$ alkyl), alkoxy groups which may be substituted, and alkenyl groups which may be substituted;

with the proviso that at least one of $R^{17}$ is a spacer group by which the dye is conjugated to the particle;

$R^{18}$ is H or an alkali metal ion, $R^{19}$, $R^{20}$, $R^{21}$ and $R^{22}$ are each independently selected from the group consisting of hydrogen, and alkyl groups which may be substituted, preferably, $R^{19}$, $R^{20}$, $R^{21}$ and $R^{22}$ are each the same;

f is an integer from 0 to 3;

g is an integer from 0 to 3; and h is an integer from 1 to 5.

2. The method of item 1, wherein the labeled particles and the ligands are provided in step a) in predetermined concentrations in the solution or the labeled particles are provided in a predetermined amount immobilized on the solid support and the ligands are provided in a predetermined concentration; and the solution provided in step a) is used in step b) for exciting fluorescently the labeled particles and detecting the fluorescence of the excited particles at a predetermined temperature.

3. The method according to item 1 or 2, wherein step (b) comprises the following steps:
ba) heating or cooling the solution to the predetermined temperature;
bb) exciting fluorescently the labeled particles and detecting the fluorescence of the excited particles at the predetermined temperature.

4. The method according to item 1 or 2 comprising the following steps:
a) providing a sample comprising labeled particles and ligands in a solution, wherein the labeled particles are dissolved or dispersed in the solution or are immobilized on a solid support;
ba) heating or cooling the solution to a predetermined temperature;
bb) exciting fluorescently the labeled particles and detecting the fluorescence of the excited particles at the predetermined temperature;
c) repeating steps (a) and (b) multiple times at different concentrations of the ligands in the solution; and
d) determining the interaction between the labeled particles and the ligands based on the ligand concentration dependent change of the fluorescence of the labeled particles.

5. The method according to item 1 or 2, wherein step (b) comprises the following steps:
b1) exciting fluorescently the labeled particles and detecting the fluorescence of the excited particles at a first predetermined temperature;
b2) heating or cooling the solution to a second predetermined temperature;
b3) exciting fluorescently the labeled particles and detecting the fluorescence of the excited particles at the second predetermined temperature.

6. The method according to any of item 1 to 5, wherein said dyes of formula (I) are dyes represented by general formula (I'):

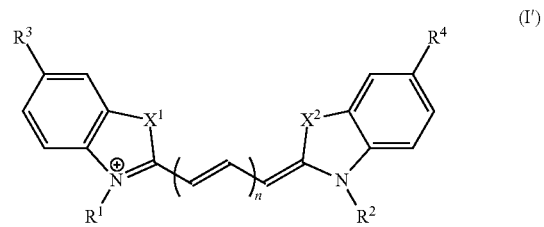

wherein
$X^1$ is O or $CR^5R^6$;
$X^2$ is O or $CR^7R^8$;
$R^1$, $R^2$, $R^5$, $R^6$, $R^7$ and $R^8$ are each independently a $C_{1-20}$ alkyl group which may be substituted;
$R^3$ and $R^4$ are each independently selected from the group consisting of hydrogen, and sulfonic acid or a salt thereof;
with the proviso that one of $R^1$, $R^2$, $R^5$, $R^6$, $R^7$ and $R^8$ is a spacer group by which the dye is conjugated to the particle, wherein the spacer group is longer than two $CH_2$-groups;
and
n is an integer equal to 1 or 2.

7. The method according to any of items 1 to 5, wherein said dyes of formula (IIa) or (IIb) are dyes represented by general formula (IIa') or (IIb'):

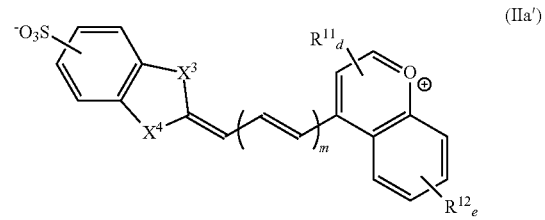

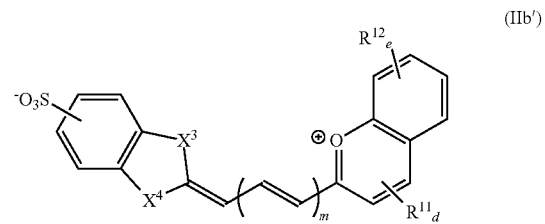

wherein
one of $X^3$ and $X^4$ is $NR^9$ and the other of $X^3$ and $X^4$ is $CR^{13}R^{14}$;
the sulfonate group is in 4-position with respect to $NR^9$;
$R^9$ is a $C_1$-$C_{20}$ alkyl group which may be substituted;
$R^{11}$, $R^{12}$, $R^{13}$ and $R^{14}$ are each independently selected from the group consisting of hydroxy, carboxy, sulfonic acid, thiol or a salt thereof, hydrogen, halogen, carboxylate ester groups which may be substituted, nitro group, amines, amides, alkyl groups which may be substituted (preferably $C_{1-4}$ alkyl), alkoxy groups which may be substituted, and alkenyl groups which may be substituted;
with the proviso that one of $R^9$, $R^{13}$ and $R^{14}$ is a spacer group by which the dye is conjugated to the particle, wherein the spacer group is longer than two $CH_2$-groups;
d is an integer from 0 to 2;
e is an integer from 0 to 3; and
m is an integer equal to 1 or 2.

8. The method according to item 7, wherein said dyes of formula (IIa') or (IIb') are dyes represented by general formula (IIa") or (IIb"):

(IIa")

(IIb")

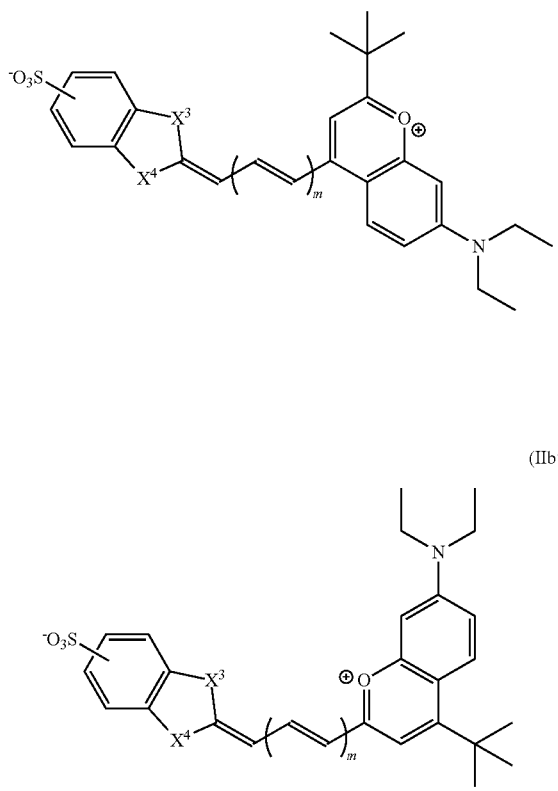

wherein one of $X^3$ and $X^4$ is $NR^9$ and the other of $X^3$ and $X^4$ is $CR^{13}R^{14}$;

the sulfonate group is in 4-position with respect to $NR^9$;

$R^9$ is a $C_{3-6}$ alkyl group which may be substituted;

$R^{13}$ and $R^{14}$ are each independently a $C_{1-4}$ alkyl group which may be substituted;

with the proviso that one of $R^9$, $R^{13}$ and $R^{14}$ is a spacer group by which the dye is conjugated to the particle, wherein the spacer group is longer than two $CH_2$- groups; and m is an integer equal to 1 or 2.

9. The method according to any of items 1 to 8, wherein the spacer group in said dyes of general formulae (I), (I'), (IIa), (IIb), (IIa'), (IIb'), (IIa") or (IIb") is a $C_4$ to $C_{20}$ alkylene chain, which may be substituted, wherein one or more carbon atoms of the alkylene chain may independently be replaced by alicyclic groups, aryl groups, heterocyclic groups, heteroaryl groups, or heteroatoms selected from the group consisting of O, N. and S.

10. The method according to item 9, wherein the spacer group is a $C_4$ to $C_6$ alkylene chain, which may be substituted, wherein one carbon atom may be replaced by one aryl group.

11. The method according to any of items 1 to 5, wherein said dyes of formula (III) are dyes represented by general formula (III'):

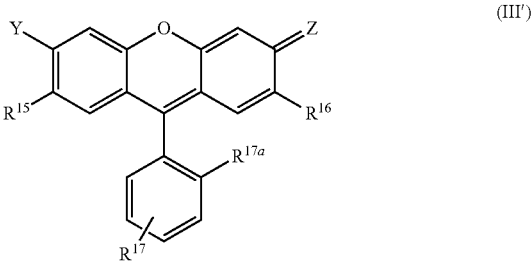

wherein

Y is OH or $N(CH_3)_2$;

Z is O or $^+N(CH_3)_2$;

$R^{15}$ and $R^{16}$ are each independently hydrogen, or a halogen;

$R^{17}$ is a spacer group by which the dye is conjugated to the particle; and $R^{17a}$ is a carboxy group, or a salt thereof.

12. The method according to any of items 1 to 5 or 11, wherein the spacer group in said dyes of general formulae (III) or (III') is a $C_2$ to $C_{10}$ alkylene chain, which may be substituted, wherein one or more carbon atoms of the alkylene chain may independently be replaced by alicyclic groups, aryl groups, heteroaryl groups, heterocyclic groups, or heteroatoms selected from the group consisting of O, N, and S.

13. The method according to item 12, wherein the spacer group is a $C_3$ to $C_7$ alkylene chain, which may be substituted, wherein one or more carbon atoms of the alkylene chain may independently be replaced by heteroatoms selected from the group consisting of O, N, and S.

14. The method according to any of items 1 to 13, wherein the predetermined temperature is in the range of −20° C. to 115° C., preferably 0.1° C. to 100° C., more preferably in the range of 5° C. to 60° C., even more preferably in the range of 10° C. to 60° C., most preferably in the range of 10° C. to 40° C.

15. The method according to item 14, wherein the predetermined temperature is different from room temperature.

16. The method according to item 14 or 15, wherein the predetermined temperature is a temperature at which the ligand binds to the labeled particle.

17. The method according to item 14 or 15, wherein the predetermined temperature is a temperature at which a fraction of the dye which undergoes a conformational change in the fluorescence excitation changes due to binding of the ligand to the labeled particle.

18. The method according to item 14 or 15, wherein the predetermined temperature is a temperature at which a photoisomerization rate or internal conversion rate of the dye changes due to binding of the ligand to the labeled particle.

19. The method according to any of items 1 to 18, wherein the predetermined temperature is controlled within +/−1 K, preferably within +/−0.5 K.

20. The method according to any of items 3 to 19, wherein the heating or cooling is carried out using a heating or cooling source selected from the group consisting of a heating or cooling fluid, a heating or cooling gas, a heating element, a peltier element, electromagnetic radiation, and combinations thereof.

21. The method according to any of items 5 to 20, wherein the first predetermined temperature is in the range of −20° C. to 115° C., preferably 0.1° C. to 100° C., more preferably in the range of 5° C. to 60° C., even more preferably in the range of 10° C. to 60° C., most preferably in the range of 10° C. to 40° C.

22. The method according to any of items 5 to 21, wherein the second predetermined temperature is in the range of −20° C. to 115° C., preferably 0.1° C. to 100° C., more preferably in the range of 5° C. to 60° C., even more preferably in the range of 10° C. to 60° C., most preferably in the range of 10° C. to 40° C.

23. The method according to any of items 5 to 20, wherein the first and second predetermined temperatures are in the range of −20° C. to 115° C., preferably 0.1° C. to 100° C., more preferably in the range of 5° C. to 60° C., even more preferably in the range of 10° C. to 60° C., most preferably in the range of 10° C. to 40° C.

24. The method according to any of items 5 to 23, wherein the first and second predetermined temperatures are controlled within +/−1 K, preferably within +/−0.5 K.

25. The method according to any of items 5 to 24, wherein the difference between the second temperature and the first temperature is in the range from +/−0.1 K to +/−90 K, preferably in the range from +/−1 K and +/−40 K, more preferably in the range from +/−1 K to +/−20 K.

26. The method according to any of items 1 to 25, wherein the sample is provided in a chamber selected from the group consisting of a multi-well plate, a capillary, a cuvette, a reaction tube, a pipette tip, microfluidics, droplets and a translucent container.

27. The method according to any of items 1 to 26, wherein the particles are selected from the group consisting of organic molecules, biomolecules, nanoparticles, microparticles, vesicles, biological cells or sub-cellular fragments, biological tissues, viral particles, viruses and cellular organelles.

28. The method according to item 27, wherein said biomolecules are selected from the group consisting of amino acids, proteins, peptides, mono- and disaccharides, polysaccharides, lipids, glycolipids, fatty acids, sterols, vitamins, neurotransmitter, enzymes, nucleotides, metabolites, nucleic acids, and combinations thereof.

29. The method according to item 28, wherein said biomolecules are selected from the group consisting of proteins, peptides, enzymes, nucleic acids, and combinations thereof.

30. The method according to item 29, wherein said proteins are selected from the group consisting of enzymes, transporter proteins, inhibitory proteins, structural proteins, signaling proteins, ligand-binding proteins, chaperones, antibodies, and receptors.

31. The method according to item 30, wherein said proteins are selected from the group consisting of enzymes, transporter protein, inhibitory proteins, chaperones, antibodies, and receptors.

32. The method according to item 29, wherein said nucleic acid is selected from DNA RNA, LNA and PNA.

33. The method according to any of items 1 to 32, wherein the concentration of the labeled particles in the solution is from 10 picomolar to 1 micromolar, preferably 100 picomolar to 100 nanomolar.

34. The method according to any of items 1 to 34, wherein the concentration of the ligand is from 0.01 picomolar to 1 molar, preferably 1 picomolar to 100 millimolar, more preferably 10 picomolar to 10 millimolar.

35. The method according to any of items 1 to 34, wherein said ligands are selected from the group consisting of ions, metals, compounds, drug fragments, carbohydrates, small molecules, drugs, prodrugs, lipids, proteins, peptides, peptoids, enzymes, nucleic acids, nanoparticles, liposomes, SUVs, GUVs, polymers, organic molecules, inorganic molecules, metal complexes, hormones, flavors, odorants, particles and (micro)beads.

36. The method of any of items 1 to 35, wherein the particle and ligand are selected from the group consisting of the following combinations denoted as particle→ligand: enzyme→lipid, receptor→hormone, receptor→chemokine, enzyme→inhibitor, receptor→neurotransmitter, receptor→cytokine, enzyme→ion, receptor→ion, receptor→amino acid, enzyme→cofactor, receptor→lipid, receptor→sterol, enzyme→fragment, receptor→peptide, receptor→fragment, enzyme→metabolite, receptor→receptor, receptor→eglycolipid, enzyme→DNA, receptor→odorant, receptor→prodrug, enzyme→RNA, receptor→drug, enzyme→mono-→/di- or polysaccharide, enzyme→fatty acid, enzyme→vitamin, enzyme→prodrug, enzyme→drug, liposome→protein, transporter protein→substrate, antibody→antigen, viral particle→receptor, virus-structural protein, antibody→Fc receptor, chaperone→ATP, ssDNA→ssDNA, aptamer→ligand, chaperone→ions, RNA→small molecule, polysaccharide→small molecule, chaperon→protein, DNA→small molecule, structural protein→structural protein, signaling protein→signaling protein, signaling protein→small molecule, signaling protein→prodrug, signaling protein→drug, signaling protein→lipid, structural protein→ions, nanoparticle→protein, cellular organelle→protein, nanoparticle→DNA, cellular organelle→lipid, nanoparticle→RNA.

37. The method of any of items 1 to 36, wherein the method of measuring interactions between labeled particles and ligands is a method of measuring the dissociation constant of the particles and the ligands.

38. A method for measuring inter- and/or intra-molecular interactions comprising the steps:
  a) providing a sample comprising labeled particles;
  b) exciting fluorescently the labeled particles and detecting a first fluorescence of the excited particles at a first temperature;
  c) heating or cooling the sample to a second temperature;
  d) exciting fluorescently the labeled particles and detecting a second fluorescence of the excited particles at the second temperature;
  e) characterizing inter- and/or intra-molecular interactions and/or modifications/alterations of the particles based on the first and second fluorescence,
  wherein the labeled particles are labeled with one or more dyes selected from the group consisting of dyes represented by general formulae (I), (IIa), (IIb) or (III) as defined in any of items 1 or 6 to 13.

39. A method for measuring time dependent changes comprising the steps:
  a) providing a sample comprising labeled particles;
  b) exciting fluorescently the labeled particles and detecting a first fluorescence of the excited particles;
  c) waiting for a predetermined time;
  d) exciting fluorescently the labeled particles and detecting a second fluorescence of the excited particles;
  e) characterizing the time dependent change of the particles based on the first and second fluorescence,
  wherein the labeled particles are labeled with one or more dyes selected from the group consisting of dyes represented by general formulae (I), (IIa), (IIb) or (III) as defined in any of items 1 or 6 to 13.

40. A method for measuring environmental dependent changes comprising the steps:
   a) providing a first sample comprising labeled particles;
   b) exciting fluorescently the labeled particles and detecting a first fluorescence of the excited particles in the first sample;
   c) providing a second sample comprising the labeled particles at substantially the same concentration, wherein the second sample differs from the first sample;
   d) exciting fluorescently the labeled particles and detecting a second fluorescence of the excited particles in the second sample;
   e) characterizing the environmental dependent change of the particles based on the first and second fluorescence, wherein the labeled particles are labeled with one or more dyes selected from the group consisting of dyes represented by general formulae (I), (IIa), (IIb) or (III) as defined in any of items 1 or 6 to 13.

41. A protein labeling kit comprising two or more reactive dyes, wherein each dye independently comprises a structural unit represented by general formulae (I), (IIa), (IIb) or (III) as defined in any of items 1 or 6 to 13, the dyes having a spacer group, the spacer group having a reactive group that enables the conjugation of the dye to a protein.

42. The protein labeling kit of item 41, further comprising an instruction manual explaining the use of the kit in at least one of the methods of any one of items 1 to 31.

43. The protein labeling kit of item 41 or 42 further comprising at least one selected from the group consisting of buffer exchange columns, purification columns, labeling buffers, adapters, and combinations thereof.

EXAMPLES

Reagents:

N-Hydroxysuccinimide (NHS) derivatized dyes were obtained from Thermo Fischer Scientific (fluorescein, Oregon Green 488, TAMRA), Lumiprobe (Cy3, Cy5, disulfoCy5, Cy5.5), Dyomics (DY495, DY567P1, DY630, DY631, DY647P1, DY650), Seta Biochemicals (SeTau-647), Cyandye (monosulfoCy3, monosulfoCy5) and ATTO TECH (ATTO488, ATTO647N, ATTO 655). The structures of all dyes used are shown in FIGS. 19a to 19e. Proteins were obtained from Crelux (Hsp90, p38α (p38 alpha), TEM1, BLIP, maltose binding protein (MBP)), carbonic anhydrase II (CAII) were purchased from Sigma-Aldrich. The NHS labeling buffer and dye separation columns were obtained from NanoTemper Technologies GmbH. As assay buffer Tris-MgCl$_2$ buffer supplemented with 0.05% Tween 20 was used [50 mM Tris-HCl, 150 mM NaCl, 10 mM MgCl$_2$).

Protein Labeling:

Target proteins (p38α, carbonic anhydrase, TEM1, Hsp90) were labeled in carbonate buffer at pH 8.2. The dye-to-protein ratio varied between 3:1 and 5:1. The labeling reaction took place at room temperature for 30 min. A free dye was separated from the labeled protein using dye separation columns provided by NanoTemper Technologies.

Devices Used:

A) IR.Red, IR.Green or IR.Blue: NanoTemper Technologies prototypes incorporating a red, green or blue fluorescence detection channel and an IR laser (wavelength 1480 nm) were used as a heating source. Optical filters used were (extinction/emission (in nm)): IR.Red 500-580/655-720 nm, IR.Green 515-555/618-652 nm, and IR.Blue 450-490/600-650 nm. The LED used were: IR.Red 20 mA, 2.1 V, 630 nm; IR.Green 20 mA, 3.4 V, 540 nm; and IR.Blue 20 mA, 3.4 V, 480 nm. These devices were used for thermo-optical characterization of different fluorophores and their sensitivity to report binding events.

B) Prometheus NT.48: A standard NT.48 device from NanoTemper Technologies that has a UV range excitation and detection optics. Sample heating was achieved with a Peltier device. The main application is the detection of melting curves of proteins.

C) PR.Red: NanoTemper Technologies prototype that uses Peltier device based sample heating in combination with red fluorescence detection channel (500-580/655-720 nm). This device was used for thermo-optical characterization of different fluorophores and their sensitivity for binding events and for thermal unfolding of the proteins.

Fluorescence Measurements:

The changes in fluorescence intensity upon the heating were measured using IR.Red, IR.Green or IR.Blue to heat the probes using IR laser, or PR.Red to heat the probes using the Peltier device. For the experiments the probes were either loaded into 384-well plates or customized glass containment. The probes contained either free dye, solely fluorescently labeled target at given concentration or a dilution series of a specific ligand mixed with fluorescently labeled target at given concentration.

Data Acquisition and Analysis:

During the data acquisition, the raw data from an analog-digital converter were displayed as fluorescence intensity (in arbitrary units). Each individual trace was then normalized to start at 1. For the depiction of a binding curve, the intervals before and after the heating were set and the data within the interval averaged and $F_{norm}$ calculated. Each data point in the binding curve represents mean $F_{norm}$ at a certain ligand concentration.

Dissociation constants ($K_d$) were determined either with MO Affinity analysis software (NanoTemper Technologies GmbH) or Origin (Origin Lab). The temperature induced changes in fluorescence intensity were normalized as: the initial fluorescence ($F_i$) intensity was defined as 1 and the data normalized as $F_T/F_i$, where $F_T$ is the fluorescence intensity at a given increased temperature. Resulting $F_{norm}$ was plotted against the increasing concentration of the given ligand. The dissociation constants ($K_d$) was determined according to the fit that describes a molecular interaction with a 1:1 stoichiometry according to the law of mass action. The $K_d$ is estimated by fitting the equation:

$$f(c) = \text{Unbound} + (\text{Bound} - \text{Unbound}) \times \frac{c + c_{target} + K_d - \sqrt{(c + c_{target} + K_d)^2 - 4c \times c_{target}}}{2c_{target}}$$

where f(c) is the fraction bound at a given ligand concentration c, Unbound is the $F_{norm}$ signal of the target, Bound is the $F_{norm}$ signal of the complex, $K_d$ is the dissociation constant or binding affinity, and $c_{target}$ is the final concentration of target in the assay.

Reference Example 1

100 nM of NHS-ester fluorophores (IR dye 650 (LI-COR Biotechnology), CF647 (Biotium), Dylight 655 B1, B2 and B3 (Thermo Scientific) and CF640R (Biotium)) in the assay buffer were loaded into Prometheus NT.48 standard treated capillaries (NanoTemper Technologies) in duplicate and subjected to thermo-optical experiments in a IR-device with a Monolith NT.115 Blue/Red optic using 4, 8, 16, 24, 32 and 40 mW IR laser power. The IR-laser induced change in fluorescence was monitored for 20 seconds. The same samples were also subjected to a linear temperature ramp by heating via a Peltier element at 1 K/min. Sample fluorescence was collected using a Monolith NT.115 Blue/Red optic (NanoTemper Technologies). For analysis, the relative fluorescence loss in the thermo-optical experiments was correlated with the temperature and the relative fluorescence loss from the experiments using linear heating in the Peltier device. The results are provided in FIG. 1.

The temperature induced changes in fluorescence intensity observed with PR.Red strictly correlates with the temperature induced changes in fluorescence intensity observed with IR.Red at the same temperature (FIGS. 1A and 1B).

Reference Example 2

Dyes were pre-diluted in DMSO and diluted further in the assay buffer to a final concentration of 100 nM. Dyes were then filled into high sensitivity Prometheus glass capillaries and loaded in triplicates into the PR.Red. Heating ramp was set to 1 K/min and data were recorded from 293-368 K. The results are provided in FIG. 2.

Reference Example 3

Dyes were pre-diluted in DMSO and diluted further in the given buffers to a final concentration of 100 nM. Dyes were then filled into high sensitivity Prometheus glass capillaries and loaded in triplicates into the PR.Red. Heating ramp was set to 1 K/min and data were recorded from 293-368 K.

Figure 3:
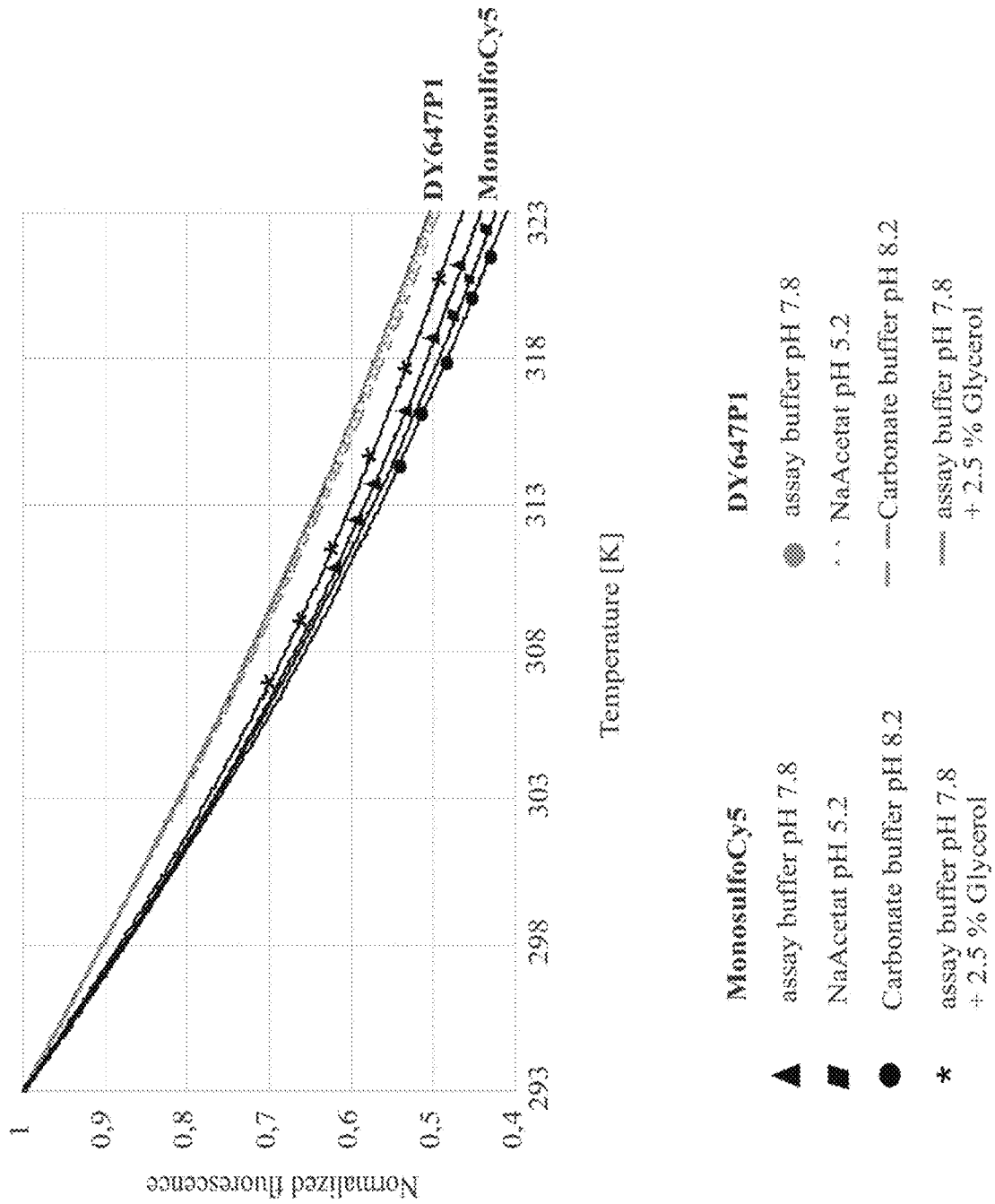
FIG. 3 shows a temperature induced fluorescence intensity change of the dyes MonosulfoCy5 and DY647P1 being modulated by the environment (e.g. pH).

It has been found that the temperature induced fluorescence intensity change is additionally modulated also by the environment in which the dye resides as shown in FIG. 3. The extent of this sensitivity is dependent from the structure of the dye. DY647P1 and monosulfoCy5 are polymethine dyes, which differ in the number of sulfonate groups. DY647P1 possesses two, monosulfoCy5 possesses only one sulfonate group.

Example 1

Recombinant EcoSSB protein was purified as described by Curth U. et al. in Biochemistry, 1993, 32 (10), pp 2585-2591, which is hereby incorporated by reference in its entirety. The protein was diluted from 1 µM down to 0.4 nM in a serial dilution in 50 mM Hepes pH 7.4, 150 mM NaCl and 2 mM EDTA in a final volume of 10 µl per concentration. Subsequently, 10 µl of a solution containing 20 nM Cy5-OligodT35 (Metabion) in the same buffer were added to each EcoSSB concentration. 10 ml of each solution were filled into Monolith NT.LabelFree Premium Coated Capillaries (for experiments using the PR.Red Peltier device) and in Monolith NT.115 Premium Coated Capillaries (for experiments in the laser device IR.Red). Heating was performed in a linear gradient from 293 K to 368 K at 7 K/min on the PR.Red, and with a laser power of 16 mW on the IR.Red. Normalized fluorescence change at the temperature of 302 K was plotted versus the concentration of EcoSSB. The results are provided in FIG. 4.

Example 2

Protein labeling: The protein TEM1 was labeled with monosulfo-Cy5 using NHS labeling buffer and a 1:3 protein to dye labeling ratio. Therefore, 100 µl of 24 µM dye solution was mixed with 100 µl of 8 µM protein solution and reaction was carried out for 30 min at RT in the dark. Free dye was removed using size-exclusion chromatography. For this, B column was equilibrated using 9 ml of the assay buffer, before the labeling reaction was loaded to enter the resin. After addition of 300 µl assay buffer, labeled proteins were eluted using 600 µl assay buffer. Here, the first 100 µl does not contain any protein and were discarded.

Preparation of serial dilution: After protein labeling, a serial dilution of the ligands was prepared. BLIP was diluted in assay buffer to 1 µM. Starting with this solution, a 16-step serial dilution was prepared using a sample volume of 10 µl. After preparation of the serial dilution, 10 µl of 132 nM labeled TEM1 was added to the dilution series. Samples were mixed by pipetting up and down. Before loading premium coated glass capillaries, samples were centrifuged for 10 min at 4° C. and 15,000 g.

Measurements with PR.Red and data analysis: The experiments were performed using PR.Red. The measurements of TEM1 affinity for BLIP was carried out using 20% LED. The data were analyzed using MO Affinity Analysis software (NanoTemper Technologies). The results are provided in FIG. 5.

Example 3

Protein labeling: The protein CAII was labeled with monosulfoCy5 or DY647P1 using NHS labeling buffer and a 1:3 protein to dye labeling ratio. Therefore, 100 µl of 24 µM dye solution was mixed with 100 µl of 8 µM protein solution and reaction was carried out for 30 min at RT in the dark. Free dye was removed using size-exclusion chromatography as described in Example 2.

Preparation of serial dilution: After protein labeling, a serial dilution of the ligands was prepared. Furosemide was diluted in assay buffer to 50 µM. Starting with this solution, a 16-step serial dilution was prepared using a sample volume of 10 µl. After preparation of the serial dilution, 10 µl of 100 nM labeled CAII was added to the dilution series. Samples were mixed by pipetting up and down. Before loading premium coated glass capillaries, samples were centrifuged for 10 min at 4° C. and 15,000 g.

Figure 6:
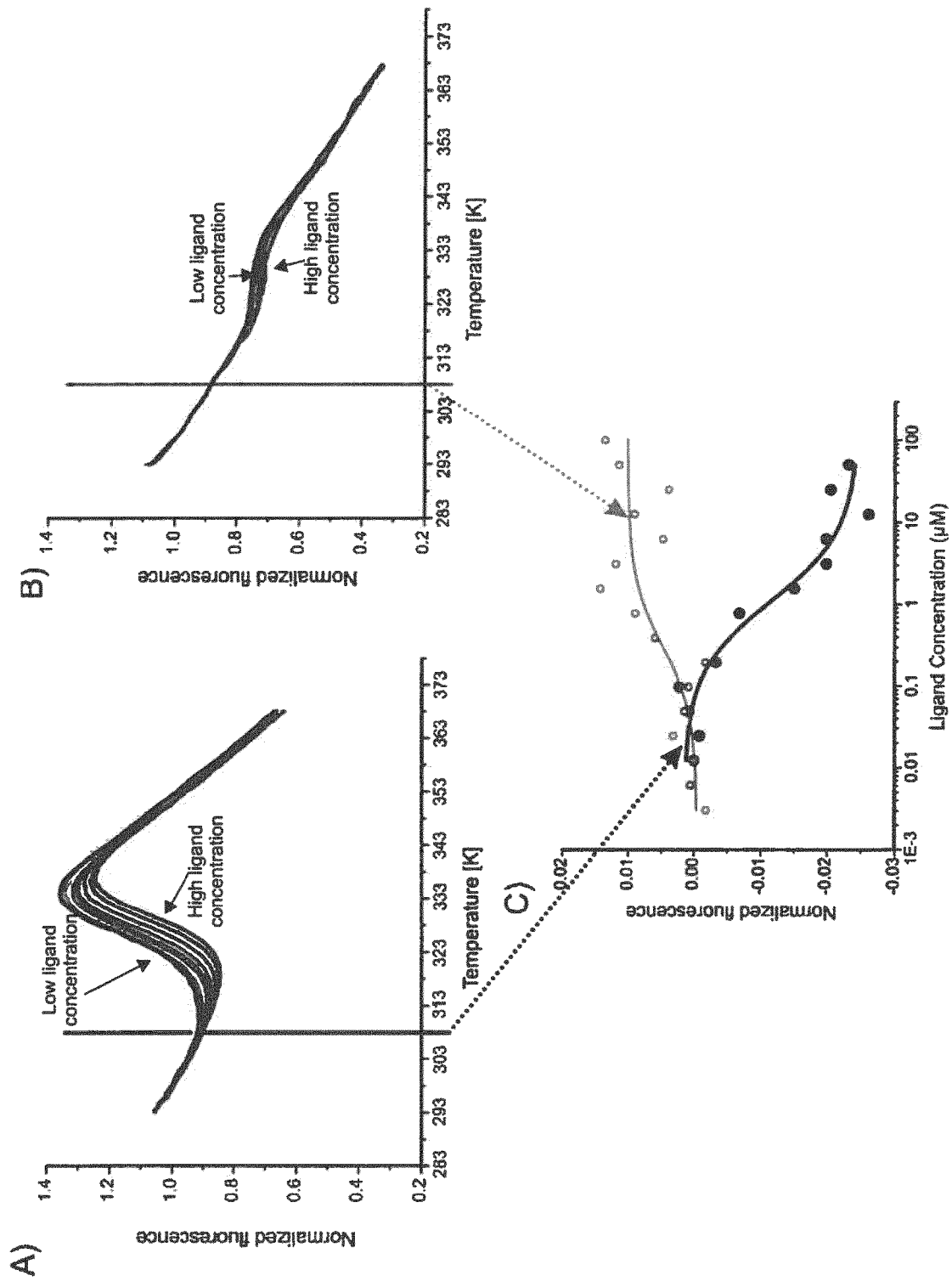
FIG. 6 shows a temperature induced fluorescence intensity change and a ligand induced fluorescence intensity change of labeled particles at 35° C. to determine the binding affinity of the ligand furosemide for carbonic anhydrase (CAII) labeled with monosulfoCy5 (A) or D647P1 (B).

Measurements with PR.Red and data analysis: The experiments were performed using PR.Red. The measurements of CAII affinity for furosemide was carried out using 20% LED. The data were analyzed using the Origin software (Origin Lab Corporation). The results are provided in FIG. 6.

Example 4

Protein labeling: The protein A was labeled with monosulfoCy5 using NHS labeling buffer and a 1:3 protein to dye labeling ratio. Therefore, 100 µl of 24 µM dye solution was mixed with 100 µl of 8 µM protein solution and reaction was carried out for 30 min at RT in the dark. Free dye was removed using size-exclusion chromatography as described in Example 2.

Preparation of serial dilution: After protein labeling, a serial dilution of the ligands was prepared. Trastuzumab was diluted in PBS-0.05% Tween 20 buffer to 2.5 µM. Starting with this solution, a 16-step serial dilution was prepared using a sample volume of 10 µl. After preparation of the serial dilution, 10 µl of 10 nM labeled protein A was added to the dilution series. Samples were mixed by pipetting up and down. Before loading premium coated glass capillaries, samples were centrifuged for 10 min at 4° C. and 15,000 g.

Figure 7:
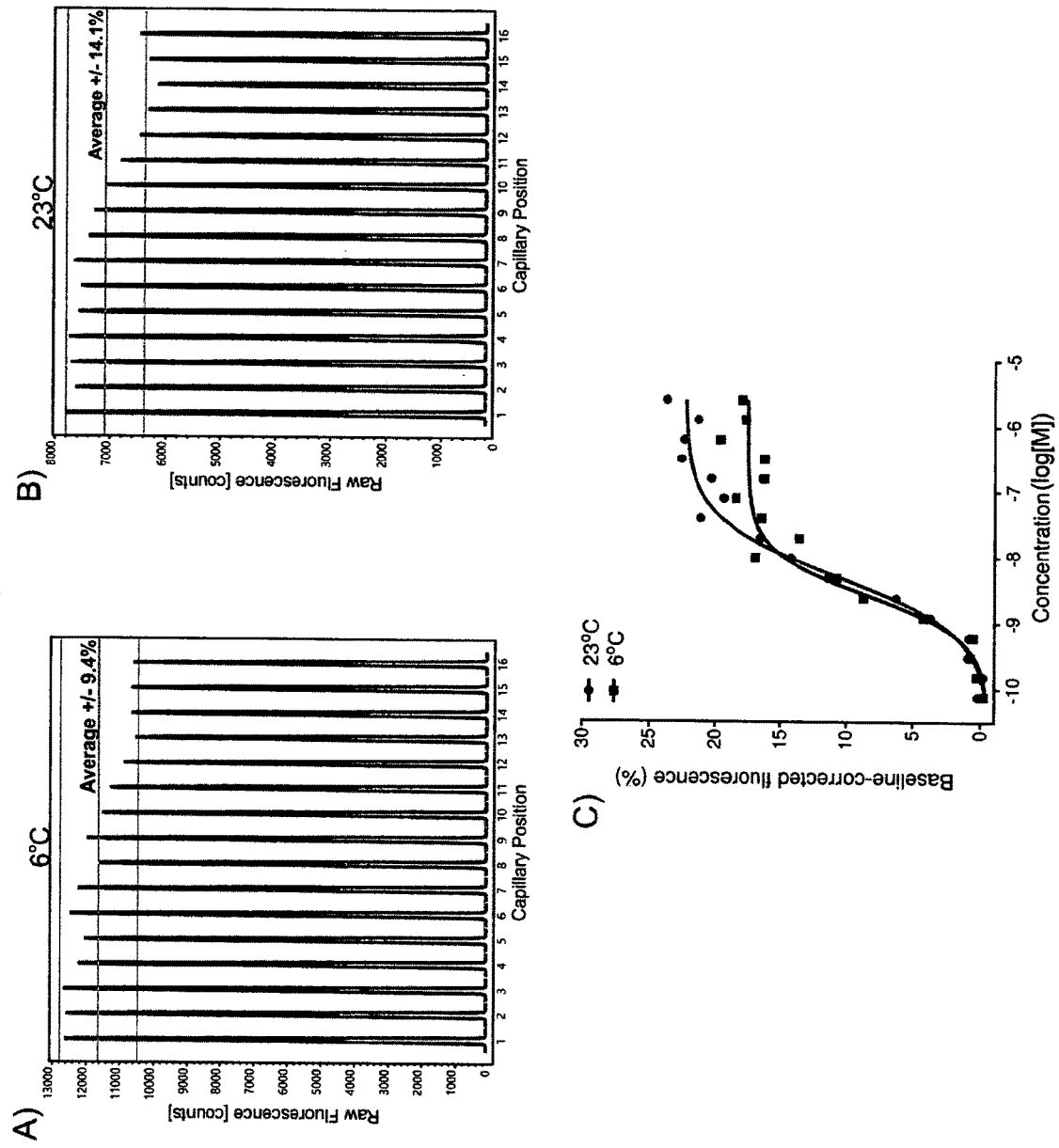
FIG. 7 shows a ligand induced fluorescence intensity change of labeled particles at 6° C. and at 23° C. to determine the binding affinity of the ligand Trastuzumab for monosulfoCy5-protein A.

Measurements with IR.Red and data analysis: The experiments were performed using IR.Red. The measurements of the protein A affinity for Trastuzumab was carried out using 20% LED and the IR-laser switched off. The data were analyzed using MO Affinity Analysis software (NanoTemper Technologies) and GraphPad Prism 7.0 (GraphPad Software Inc.). The results are provided in FIG. 7.

Example 5

Protein labeling: The IL-R1 protein was labeled with DyLight655 derivatives according to standard NHS labeling protocol. For this, the dye was pre-diluted in DMSO and further diluted in NHS labeling buffer to a final concentration of 6 μM. The protein was diluted to a final concentration of 2 μM in the same labeling reaction optimized buffer. For the labeling reaction 100 μl of dye solution was mixed with 100 μl of protein solution and reaction was carried out for 30 min at RT in the dark. Afterwards free dye was removed using size-exclusion chromatography. For this, B column was equilibrated using 9 ml of the assay buffer, before the labeling reaction was loaded to enter the resin. After addition of 300 μl assay buffer, labeled proteins were eluted using 600 μl assay buffer. Here, the first 100 μl does not contain any protein and were discarded.

Preparation of serial dilution: After protein labeling, a serial dilution of the ligand Anakinra was prepared a sample volume of 10 μl. After preparation of the serial dilution, 10 μl of 1 nM labeled protein was added to all ligand dilutions. Samples were mixed by pipetting up and down. Before loading premium coated glass capillaries, samples were centrifuged for 1 min at 4° C. and 15,000 g.

Measurements with IR.Red and data analysis: The experiments were performed using IR.Red at IR-laser power of 12 mW to heat the probes to 310 K at LED power of 60%. The data were analyzed using MO Affinity Analysis software (NanoTemper Technologies). The results are provided in FIG. 8.

Example 6

Protein labeling: The p38 alpha protein was labeled with Cy5 using NHS labeling chemistry. For this, the dye was pre-diluted in DMSO and further diluted in NHS labeling buffer to a final concentration of 24 μM. The protein was diluted to a final concentration of 8 μM using the same labeling reaction optimized buffer. For the labeling reaction 100 μl of dye solution was mixed with 100 μl of protein solution and reaction was carried out for 30 min at RT in the dark. Afterwards free dye was removed using size-exclusion chromatography. For this, B column was equilibrated using 9 ml of the assay buffer, before the labeling reaction was loaded to enter the resin. After addition of 300 μl assay buffer, labeled proteins were eluted using 600 μl assay buffer. Here, the first 100 μl does not contain any protein and were discarded.

Preparation of serial dilution: After protein labeling, a serial dilution of the ligands was prepared. The assay buffer with 4% DMSO served as the assay buffer. PD169316 was diluted in assay buffer to 10 μM and 4% DMSO. Starting with this solution, a 16-step serial dilution was prepared using a sample volume of 10 μl. After preparation of the serial dilution, 10 μl of 100 nM labeled protein was added to all ligand dilutions. Samples were mixed by pipetting up and down. Before loading premium coated glass capillaries, samples were centrifuged for 10 min at 4° C. and 15,000 g.

Measurements with IR.Red and data analysis: The experiments were performed using IR.Red at IR-laser power of 24 mW and the LED power of 20%. The probe was prewarmed with the IR-laser the temperature of 308 K. Upon cooling of the probe to 296 K, the fluorescence change was monitored. The data were analyzed using MO Affinity Analysis software (NanoTemper Technologies). The results are provided in FIG. 9.

Example 7

Protein labeling: Histagged p38α was labeled with Oregon Green 488 tris-NTA derivative. For this, the dye was diluted in PBST to a final concentration of 100 nM, while the protein concentration was adjusted to 200 nM using PBST buffer. Both samples were mixed 1:1 with a final volume of 200 μl and the labeling reaction was carried out for 30 min at RT in the dark. Afterwards the reaction mixture was centrifuged for 10 min at 4° C. and 15,000 g.

Histagged p38 alpha was labeled with Oregon Green 488, Cy5, Z Cy5, TAMRA and TAMRAX using NHS labeling chemistry. For this, the dye was pre-diluted in DMSO and further diluted in NHS labeling buffer to a final concentration of 6 μM for Z-Cy5 and 24 μM for the other dyes. The protein was diluted to a final concentration of 2 μM for Z-Cy5 and 8 μM for the other dyes using the same labeling reaction optimized buffer. For the labeling reaction 100 μl of dye solution was mixed with 100 μl of protein solution and reaction was carried out for 30 min at RT in the dark. Afterwards free dye was removed using size-exclusion chromatography. For this, B column was equilibrated using 9 ml of the assay buffer, before the labeling reaction was loaded to enter the resin. After addition of 300 μl assay buffer, labeled proteins were eluted using 600 μl assay buffer. Here, the first 100 μl does not contain any protein and were discarded.

Preparation of serial dilution: After protein labeling, a serial dilution of the ligands was prepared. The assay buffer with 4% DMSO served as the assay buffer. PD169316 for Z-Cy5 labeled p38 and BIRB for the other labeling products were diluted in assay buffer to 10 μM and 4% DMSO. Starting with this solution, a 16-step serial dilution was prepared using a sample volume of 10 μl. After preparation of the serial dilution, 10 μl of 100 nM labeled protein was added to all ligand dilutions. Samples were mixed by pipetting up and down. Before loading premium coated glass capillaries, samples were centrifuged for 10 min at 4° C. and 15,000 g.

Measurements with IR.Red and data analysis: The experiments were performed using IR.Red at IR-laser power of 24 mW. For the dyes Cy5, Z-Cy5, Oregon Green 488 and Oregon Green 488-tris NTA the probes were heated from 296 K to 310 K and for TAMRA and TAMRA X to 318 K. Due to intrinsic differences in the fluorescence intensity of dyes, the LED power had to be optimized for each dye. For the p38α-Cy5 was measured using 20%, while p38 alpha Z-Cy5 was analyzed using 60% LED power. TAMRA and TAMRAX labeled p38 alpha was tested using 100% and 40% LED power. Oregon Green 488 and Oregon Green 488-tris-NTA labeled p38 alpha was detected using 100% and 40% LED power, respectively. The data were analyzed using MO Affinity Analysis software (NanoTemper Technologies). The results are provided in FIG. 10.

Example 8

Protein labeling: The proteins TEM1 and p38 alpha were both labeled with DY647P1 and monosulfo-Cy5 using NHS labeling buffer and a 1:3 protein to dye labeling ratio. Therefore, 100 µl of 24 µM dye solution was mixed with 100 µl 8 µM protein solution and reaction was carried out for 30 min at RT in the dark. Free dye was removed using size-exclusion chromatography as described in Example 2.

Preparation of serial dilution: After protein labeling, a serial dilution of the ligands was prepared. The assay buffer with 4% DMSO served as the assay buffer for p38 alpha against BIRB, while the assay buffer was used for TEM1 against BLIP. BIRB and BLIP were both diluted in assay buffer to 10 µM and 4% DMSO and 1 µM, respectively. Starting with these solutions, a 16-step serial dilution was prepared using a sample volume of 10 µl. After preparation of the serial dilution, 10 µl of 100 nM labeled p38 alpha or 132 nM labeled TEM1 was added to the dilution series. Samples were mixed by pipetting up and down. Before loading premium coated glass capillaries, samples were centrifuged for 10 min at 4° C. and 15,000 g.

Measurements with IR.Red and data analysis: The experiments were performed using IR.Red at IR-laser power of 24 mW at the temperature between 310 K and 318 K. Due to intrinsic differences in the fluorescence intensity of dyes, the LED power had to be optimized for each dye. The measurements of TEM1 affinity for BLIP was carried out using 30% LED power for DY647P1 labeled TEM1 and 80% LED power for Monosulfo-Cy5 labeled TEM1. The affinity of p38 alpha-DY647P1 for BIRB was measured using 30% LED power, while p38 Monosulfo-Cy5 was analyzed using 80% LED power. The data were analyzed using MO Affinity Analysis software (NanoTemper Technologies). The results are provided in FIG. 11.

Example 9

Protein labeling: The proteins TEM1 and p38 alpha were labeled with Monosulfo-Cy5, DY630 and DY631 using NHS labeling chemistry and a 1:3, 1:3 and 1:5 dye to protein labeling ratio, respectively. Therefore, 100 µl of 24 µM dye solution was mixed with 100 µl 8 µM protein solution and reaction was carried out for 30 min at RT in the dark. Free dye was removed using size-exclusion chromatography as described in Example 2.

Preparation of serial dilution: After protein labeling, a serial dilution of the ligands BLIP and PD169316 was prepared. The assay buffer with 4% DMSO served as the assay buffer for p38 alpha against PD169316, while the assay buffer was used for TEM1 against BLIP. PD169316 and BLIP were both diluted in assay buffer to 10 µM and 4% DMSO and 1 µM, respectively. Starting with these solutions, a 16-step serial dilution was prepared using a sample volume of 10 µl. After preparation of the serial dilution, 10 µl of 100 nM labeled p38 alpha or 132 nM labeled TEM1 was added to the dilution series. Samples were mixed by pipetting up and down. Before loading premium coated glass capillaries, samples were centrifuged for 10 min at 4° C. and 15,000 g.

Measurements with IR.Red and data analysis: The experiments were performed using IR.Red at IR-laser power of 24 mW to heat the probes to the temperature between 310 K and 318 K. Due to intrinsic differences in the fluorescence intensity of dyes, the LED power had to be optimized for each dye: 100% LED power for DY630 labeled TEM1, 80% LED power for DY631 labeled TEM1 and 60% LED power for Monosulfo-Cy5 labeled TEM1. The data were analyzed using MO Affinity Analysis software (NanoTemper Technologies). The results are provided in FIG. 12.

Example 10

The proteins p38α and TEM1 were both labeled with Monosulfo-Cy5. Further p38 alpha was labeled using SeTau647. For this, dyes were dissolved in DMSO and diluted further to a final concentration of 24 µM using NHS labeling buffer. For a protein to dye ratio of 1:3, proteins were diluted to a final concentration of 8 µM using NHS labeling buffer. For the labeling reaction 100 µl of dye solution was mixed with 100 µl of protein solution and reaction was carried out for 30 min at RT in the dark. Afterwards free dye was removed using size-exclusion chromatography. For this, B column was equilibrated using 9 ml of the assay buffer, before the labeling reaction was loaded to enter the resin. After addition of 300 µl assay buffer, labeled proteins were eluted using 600 µl assay buffer. Here, the first 100 µl does not contain any protein and were discarded. After B column purification, proteins were directly loaded into high sensitivity Prometheus glass capillaries (1.6 µM) and were measured in duplicates using the PR.Red with the following device settings: 1 K/min; from 293-368 K.

Free dyes were pre-diluted in DMSO and further diluted in assay buffer to a final concentration of 100 nM. Dyes were then filled into high sensitivity Prometheus glass capillaries and loaded in triplicates into the PR.Red device. Heating ramp was set to 1 K/min and data were recorded from 293-368 K. Data was analyzed using Microsoft Excel. The results are provided in FIG. 15.

Example 11

The proteins TEM1 and MBP were both labeled with Monosulfo-Cy5 using NHS labeling buffer and a 1:3 protein to dye labeling ratio. For this, the dye was dissolved in DMSO and further diluted in NHS labeling buffer to a final concentration of 24 µM. Proteins were diluted to a final concentration of 8 µM using the same labeling reaction optimized buffer. For the labeling reaction 100 µl of dye solution was mixed with 100 µl of protein solution and reaction was carried out for 30 min at RT in the dark. Afterwards free dye was removed using size-exclusion chromatography. For this, B column was equilibrated using 9 ml of the assay buffer, before the labeling reaction was loaded to enter the resin. After addition of 300 µl assay buffer, labeled proteins were eluted using 600 µl assay buffer. Here, the first 100 µl does not contain any protein and were discarded. After B column purification, proteins were directly loaded into high sensitivity Prometheus glass capillaries (1.6 µM) and were measured in duplicates using two devices: PR.Red using 1 K/min from 293-368 K and Prometheus NT.48 using 5 K/min from 293-368 K. Data were directly exported from the device software. The results are provided in FIG. 16.

The invention claimed is:
1. A method for measuring interactions between labeled particles and ligands comprising the steps:
  a) providing a sample comprising labeled particles and ligands in a solution, wherein the labeled particles are dissolved or dispersed in the solution or are immobilized on a solid support, wherein the labeled particles are present in the solution in a concentration from 10 picomolar to 1 micromolar;
  b) exciting fluorescently the labeled particles and detecting the fluorescence of the excited particles at a first predetermined temperature;
  c) heating or cooling the solution to a second predetermined temperature, wherein the heating or cooling is carried out using a heating or cooling source selected from the group consisting of a heating or cooling fluid, a heating or cooling gas, a heating element, a peltier element, electromagnetic radiation, and combinations thereof, wherein the second predetermined temperature is different from the first predetermined temperature, and wherein the difference between the second temperature and the first temperature is in the range from +/−0.1 Kelvin (K) to +/−90 K;

d) exciting fluorescently the labeled particles and detecting the fluorescence of the excited particles at the second predetermined temperature;

e) repeating (a) through (d) multiple times at different concentrations of the ligands in the solution thereby obtaining a first and second binding curve showing the ligand concentration dependent change of the fluorescence of the excited particles at the first and second predetermined temperature respectively; and f) determining the interaction between the labeled particles and the ligands based on the ligand concentration dependent change of the fluorescence of the labeled particles, wherein the labeled particles are labeled with a dye selected from the group consisting of Chromeo P543, DY630, DY631, DY650, DyLight 655 B2, DyLight 655 B3, Cyanine 2, Cy3, Monosulfo Cy3, Cy5, Monosulfo Cy5 (version 1), Monosulfo Cy5 (version 2), Disulfo Cy5, Cy5.5, Z-Cy2, Z-Cy5, Monosulfo Z-Cy5, Alexa 647, DY547P1, DY647P1, TAMRA, TAMRA X, DY495, and Oregon Green 488; and wherein the particle is a protein.

2. The method according to claim 1, wherein the predetermined temperature is in the range of ~20° C. to 115° C.

3. The method according to claim 2, wherein the predetermined temperature is different from room temperature.

4. The method according to claim 1, wherein the predetermined temperature is controlled within +/−1 K, preferably within +/−0.5 K.

5. The method according to claim 1, wherein the first and second predetermined temperatures are in the range of ~20° C. to 115° C.

6. The method according to claim 1, wherein the first and second predetermined temperatures are controlled within +/−1 K, preferably within +/−0.5 K.

7. The method according to claim 1, wherein the concentration of the labeled particles in the solution is from 100 picomolar to 100 nanomolar.

8. The method according to claim 1, wherein the concentration of the ligand is from 0.01 picomolar to 1 molar.

9. The method according to claim 1, wherein said ligands are selected from the group consisting of ions, metals, compounds, drug fragments, carbohydrates, small molecules, drugs, prodrugs, lipids, proteins, peptides, peptoids, enzymes, nucleic acids, nanoparticles, liposomes, SUVs, GUVs, polymers, organic molecules, inorganic molecules, metal complexes, hormones, flavors, odorants, particles and (micro)beads.

10. The method according to claim 1, wherein the particle and ligand are selected from the group consisting of the following combinations denoted as particle—ligand:

enzyme—lipid, receptor—hormone, receptor—chemokine, enzyme—inhibitor, receptor— neurotransmitter, receptor—cytokine, enzyme—ion, receptor—ion, receptor—amino acid, enzyme—cofactor, receptor—lipid, receptor—sterol, enzyme—fragment, receptor—peptide, receptor—fragment, enzyme—metabolite, receptor—receptor, receptor— glycolipid, enzyme—DNA, receptor—odorant, receptor—prodrug, enzyme—RNA, receptor—drug, enzyme—mono-/di- or polysaccharide, enzyme—fatty acid, enzyme vitamin, enzyme—prodrug, enzyme—drug, liposome—protein, transporter protein substrate, antibody—antigen, antibody—Fc receptor, chaperone—ATP, aptamer—ligand, chaperon—protein, structural protein—structural protein, signaling protein—signaling protein, signaling protein—small molecule, signaling protein—prodrug, signaling protein—drug, signaling protein—lipid, and structural protein-ions.

11. The method according to claim 1, wherein the method of measuring interactions between labeled particles and ligands is a method of measuring the dissociation constant of the particles and the ligands.

* * * * *